(12) United States Patent
Beaton et al.

(10) Patent No.: US 9,422,310 B2
(45) Date of Patent: *Aug. 23, 2016

(54) GONADOTROPIN-RELEASING HORMONE RECEPTOR ANTAGONISTS AND METHODS RELATING THERETO

(71) Applicant: Neurocrine Biosciences, Inc., San Diego, CA (US)

(72) Inventors: Graham Beaton, Poway, CA (US); Mi Chen, San Diego, CA (US); Timothy Richard Coon, Carlsbad, CA (US); Todd Ewing, San Diego, CA (US); Wanlong Jiang, San Diego, CA (US); Willy Moree, San Diego, CA (US); Martin Rowbottom, San Diego, CA (US); Warren Wade, San Diego, CA (US); Liren Zhao, San Diego, CA (US); Richard Lowe, Oakland, CA (US); Nicole Smith, San Diego, CA (US); Neil Ashweek, San Diego, CA (US); Yun-Fei Zhu, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/592,690

(22) Filed: Jan. 8, 2015

(65) Prior Publication Data

US 2015/0183800 A1 Jul. 2, 2015

Related U.S. Application Data

(60) Continuation of application No. 13/910,961, filed on Jun. 5, 2013, now Pat. No. 8,952,161, which is a continuation of application No. 13/293,943, filed on Nov. 10, 2011, now Pat. No. 8,481,738, which is a division of application No. 12/594,809, filed as application No. PCT/US2008/059438 on Apr. 4, 2008, now Pat. No. 8,084,614.

(60) Provisional application No. 60/910,621, filed on Apr. 6, 2007.

(51) Int. Cl.
| | |
|---|---|
| *C07D 513/02* | (2006.01) |
| *C07D 495/04* | (2006.01) |
| *C07C 233/88* | (2006.01) |
| *C07C 235/42* | (2006.01) |
| *C07C 255/57* | (2006.01) |
| *C07D 213/56* | (2006.01) |

(Continued)

(52) U.S. Cl.
CPC ............ *C07D 495/04* (2013.01); *C07C 233/88* (2013.01); *C07C 235/42* (2013.01); *C07C 255/57* (2013.01); *C07D 213/56* (2013.01); *C07D 213/58* (2013.01); *C07D 213/61* (2013.01); *C07D 213/64* (2013.01); *C07D 213/70* (2013.01); *C07D 213/81* (2013.01); *C07D 213/84* (2013.01); *C07D 213/89* (2013.01); *C07D 215/14* (2013.01); *C07D 215/54* (2013.01); *C07D 239/36* (2013.01); *C07D 401/04* (2013.01); *C07D 401/12* (2013.01); *C07D 413/12* (2013.01); *C07D 417/12* (2013.01)

(58) Field of Classification Search
CPC .................................................... C07D 495/04
USPC ......................................................... 546/114
See application file for complete search history.

(56) References Cited

U.S. PATENT DOCUMENTS

| | | | |
|---|---|---|---|
| 4,826,833 | A | 5/1989 | Chen |
| 5,017,211 | A | 5/1991 | Wenger et al. |

(Continued)

FOREIGN PATENT DOCUMENTS

| | | |
|---|---|---|
| EP | 3-173865 A | 7/1991 |
| EP | 0 708 756 B1 | 6/2005 |

(Continued)

OTHER PUBLICATIONS

West (Solid-State Chemistry and Its Applications, 1984, John Wiley & Sons).*

(Continued)

*Primary Examiner* — Nizal Chandrakumar
(74) *Attorney, Agent, or Firm* — Seed IP Law Group PLLC

(57) ABSTRACT

GnRH receptor antagonists are disclosed which have utility in the treatment of a variety of sex-hormone related conditions in both men and women. The compounds of this invention have the structure:

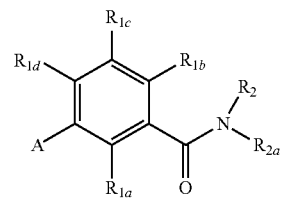

wherein $R_{1a}$, $R_{1b}$, $R_{1c}$, $R_{1d}$, $R_2$, $R_{2a}$, and A are as defined herein, including stereoisomers, esters, solvates and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

19 Claims, No Drawings

(51) Int. Cl.

| | |
|---|---|
| *C07D 213/61* | (2006.01) |
| *C07D 213/64* | (2006.01) |
| *C07D 213/70* | (2006.01) |
| *C07D 213/81* | (2006.01) |
| *C07D 213/84* | (2006.01) |
| *C07D 213/89* | (2006.01) |
| *C07D 215/14* | (2006.01) |
| *C07D 215/54* | (2006.01) |
| *C07D 239/36* | (2006.01) |
| *C07D 401/04* | (2006.01) |
| *C07D 401/12* | (2006.01) |
| *C07D 413/12* | (2006.01) |
| *C07D 417/12* | (2006.01) |
| *C07D 213/58* | (2006.01) |

(56) References Cited

U.S. PATENT DOCUMENTS

| | | | |
|---|---|---|---|
| 5,082,849 | A | 1/1992 | Huang et al. |
| 5,612,356 | A | 3/1997 | Yoshimura et al. |
| 5,614,532 | A | 3/1997 | Carling et al. |
| 5,783,522 | A | 7/1998 | Schaefer et al. |
| 5,872,116 | A | 2/1999 | Dorn et al. |
| 6,074,989 | A | 6/2000 | Andree et al. |
| 6,258,822 | B1 | 7/2001 | Geyer et al. |
| 6,310,107 | B1 | 10/2001 | Kato et al. |
| 6,319,931 | B1 | 11/2001 | Kroemer et al. |
| 6,635,657 | B1 | 10/2003 | Beight et al. |
| 6,699,994 | B1 | 3/2004 | Babu et al. |
| 7,683,097 | B2 | 3/2010 | Murphy et al. |
| 8,084,614 | B2 * | 12/2011 | Beaton ............ C07C 233/88 546/308 |
| 8,481,738 | B2 | 7/2013 | Beaton et al. |
| 2003/0013719 | A1 | 1/2003 | Peukert et al. |
| 2004/0043903 | A1 | 3/2004 | Puhl et al. |
| 2004/0186148 | A1 | 9/2004 | Shankar et al. |
| 2004/0260080 | A1 | 12/2004 | Hovinen et al. |
| 2005/0182053 | A1 | 8/2005 | Chen et al. |
| 2005/0215548 | A1 | 9/2005 | Wang et al. |
| 2006/0270686 | A1 | 11/2006 | Kelly et al. |
| 2007/0010537 | A1 | 1/2007 | Hamamura et al. |
| 2007/0117797 | A1 | 5/2007 | Goble et al. |
| 2007/0135497 | A1 | 6/2007 | Mitani et al. |
| 2007/0259919 | A1 | 11/2007 | Rheinheimer et al. |
| 2009/0069301 | A1 | 3/2009 | Milburn et al. |
| 2009/0325900 | A1 | 12/2009 | Ohno et al. |
| 2010/0184741 | A1 | 7/2010 | Ashweek et al. |

FOREIGN PATENT DOCUMENTS

| | | |
|---|---|---|
| EP | 1657238 A1 | 5/2006 |
| EP | 1847541 A | 10/2007 |
| EP | 1939204 A | 7/2008 |
| WO | 92/00290 A1 | 1/1992 |
| WO | 95/02580 A2 | 1/1995 |
| WO | 96/07667 A1 | 3/1996 |
| WO | 96/14315 A1 | 3/1996 |
| WO | 98/50343 A2 | 11/1998 |
| WO | 99/02502 A2 | 1/1999 |
| WO | 99/55663 A1 | 11/1999 |
| WO | 00/39118 A1 | 7/2000 |
| WO | 00/69859 A1 | 11/2000 |
| WO | 01/29044 A1 | 4/2001 |
| WO | 01/55119 A2 | 8/2001 |
| WO | 01/81316 A2 | 11/2001 |
| WO | 02/20501 A2 | 3/2002 |
| WO | 02/32411 A2 | 4/2002 |
| WO | 02/34711 A1 | 5/2002 |
| WO | 03/011293 A2 | 2/2003 |
| WO | 03/011839 A1 | 2/2003 |
| WO | 03/011870 A1 | 2/2003 |
| WO | 03/013528 A1 | 2/2003 |
| WO | 2004/002948 A1 | 1/2004 |
| WO | 2004/006858 A2 | 1/2004 |
| WO | 2004/041789 A1 | 5/2004 |
| WO | 2004/052371 A2 | 6/2004 |
| WO | 2004/091480 A2 | 10/2004 |
| WO | 2004/096795 A2 | 11/2004 |
| WO | 2005/007164 A1 | 1/2005 |
| WO | 2005/007165 A1 | 1/2005 |
| WO | 2005/007633 A1 | 1/2005 |
| WO | 2005/012241 A2 | 2/2005 |
| WO | 2005/020921 A2 | 3/2005 |
| WO | 2005/044007 A1 | 5/2005 |
| WO | 2005/073232 A1 | 8/2005 |
| WO | 2006/000358 A1 | 1/2006 |
| WO | 2006/017214 A2 | 2/2006 |
| WO | 2006/022955 A2 | 3/2006 |
| WO | 2006/028958 A2 | 3/2006 |
| WO | 2006/040568 A1 | 4/2006 |
| WO | 2006/044975 A2 | 4/2006 |
| WO | 2006/078287 A2 | 7/2006 |
| WO | 2006/083005 A | 8/2006 |
| WO | 2006/118155 A1 | 9/2006 |
| WO | 2006/133559 A1 | 12/2006 |
| WO | 2007/046392 A1 | 4/2007 |
| WO | 2008/124610 A1 | 10/2008 |

OTHER PUBLICATIONS

European Patent Application 08745136 Examination Report mailed Apr. 14, 2010.

Felberbaum et al., "Clinical application of GnRH-antagonists," *Molecular and Cellular Endocrinology* 166:9-14, 2000.

Fu et al., "The directed *ortho* metalation—palladium catalyzed cross coupling connection. A general regiospecific route to 9-phenanthrols and phenanthrenes. Exploratory further metalation," *Can. J. Chem.* 78:905-919, 2000.

Huirne et al., "Gonadotropin-releasing-hormone-receptor antagonists," *The Lancet* 358:1793-1803, Nov. 24, 2001.

International Preliminary Report on Patentability and Written Opinion dated Oct. 15, 2009 for PCT/US2008/059438, International Filing Date: Apr. 4, 2009, 9 pages.

PCT/US08/059438 International Search Report mailed Sep. 25, 2008.

Távora et al., "Advances in Prodrug Design," *Mini-Reviews in Medicinal Chemistry* 5:893-914, 2005.

Vippagunta et al., "Crystalline Solids," *Advanced Drug Delivery Reviews* 48:3-26, 2001.

West, Anthony R., "Solid State Chemistry and its Applications," John Wiley & Sons, 1984, 3 pages.

* cited by examiner

GONADOTROPIN-RELEASING HORMONE RECEPTOR ANTAGONISTS AND METHODS RELATING THERETO

CROSS-REFERENCE TO RELATED APPLICATIONS

This application is a continuation of U.S. patent application Ser. No. 13/910,961 filed Jun. 5, 2013, which issued as U.S. Pat. No. 8,952,161 on Feb. 10, 2015, which is a continuation of U.S. patent application Ser. No. 13/293,943 filed Nov. 10, 2011, now issued as U.S. Pat. No. 8,481,738 on Jul. 9, 2013, which is a divisional of U.S. patent application Ser. No. 12/594,809, filed Feb. 22, 2010, now issued as U.S. Pat. No. 8,084,614 on Dec. 27, 2011, which application is a U.S. national stage application filed under 35 U.S.C. §371 of International Patent Application No. PCT/US2008/059438, accorded an international filing date of Apr. 4, 2008, which claims the benefit of U.S. Provisional Application No. 60/910,621, filed Apr. 6, 2007, all of which applications are incorporated herein by reference in their entirety.

BACKGROUND OF THE INVENTION

1. Technical Field

This invention relates generally to gonadotropin-releasing hormone (GnRH) receptor antagonists, and to methods of treating disorders by administration of such antagonists to a warm-blooded animal in need thereof.

2. Description of the Related Art

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH$_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine leiomyoma (fibroids), ovarian cancer, prostatic hyperplasia, assisted reproductive therapy, and precocious puberty (The Lancet 358:1793-1803, 2001; *Mol. Cell. Endo.* 166:9-14, 2000). For example, peptidic GnRH agonists, such as leuprorelin (pGlu-His-Trp-Ser-Tyr-d-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2-3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. Recently published PCT applications which disclose compounds and their use as GnRH antagonists include WO 00/69859, WO 01/29044, WO 01/55119, WO 03/013528, WO 03/011870, WO 03/011841, WO 03/011839, WO 03/011293, WO 05/007164, WO 05/007165 and WO 05/007633.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

BRIEF SUMMARY

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

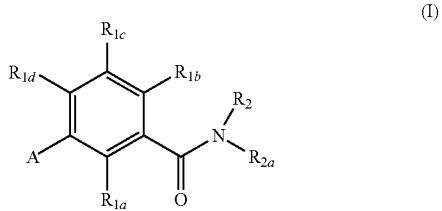

including stereoisomers, esters, solvates and pharmaceutically acceptable salts thereof, wherein $R_{1a}$, $R_{1b}$, $R_{1c}$, $R_{1d}$, $R_2$, $R_{2a}$, and A are as defined below.

The GnRH receptor antagonists of this invention may have utility over a wide range of therapeutic applications, and may be used to treat a variety of sex-hormone related conditions in both men and women, as well as a mammal in general (also referred to herein as a "subject"). For example, such therapeutic applications include endometriosis, uterine fibroids, polycystic ovarian disease, dysmenorrhea, dyspareunia, menorrhagia, nonmenstrual pelvic pain, pelvic tenderness, induration, general disorders of the menstrual cycle, premature ovarian failure due to chemotherapy or early menopause, hirsutism, precocious puberty, gonadal steroid-dependent neoplasia such as cancers of the prostate, breast and ovary, gonadotroph pituitary adenomas, adenomyosis, sleep apnea, irritable bowel syndrome, premenstrual syndrome, benign prostatic hypertrophy, lower urinary tract symptoms (LUTS), contraception and infertility (e.g., assisted reproductive therapy such as in vitro fertilization). The compounds of this invention may also be useful as an adjunct to treatment of growth hormone deficiency and short stature, and for the treatment of systemic lupus erythematosis. The compounds also may be useful in combination with androgens, estrogens, progesterones, antiestrogens, antiprogestogens, angiotensin-converting enzyme inhibitors, angiotensin II-receptor antagonists, renin inhibitors, bisphosphonates and other agents for the treatment and/or prevention of disturbances of calcium, phosphate and bone metabolism, aromatase inhibitors, analgesics such as non-steroidal anti-inflamatory drugs (NSAIDS), other COX inhibitors, and anti-NGF agents.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

As mentioned above, the present invention is directed generally to compounds useful as gonadotropin-releasing hormone (GnRH) receptor antagonists. The compounds of this invention have the following structure (I):

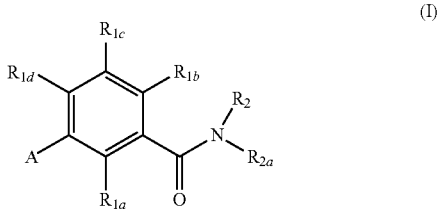

(I)

and stereoisomers, esters, solvates, and pharmaceutically acceptable salts thereof,
wherein:
A is pyridyl, phenyl, quinolinyl, naphthyridinyl, thienopyrimidinyl, or 2-oxo-pyrimidinyl wherein the pyridyl, phenyl, quinolinyl, thienopyrimidinyl or 2-oxo-pyrimidinyl are substituted with 0-5 $R_4$;

$R_{1a}$ is H, halogen, $C_{1-4}$alkyl, alkoxy or trifluoromethyl;

$R_{1b}$ and $R_{1c}$ are the same or different and are independently H, halogen, hydroxy, halo$C_{1-4}$alkyl, —$C_{1-6}$alkyl-$(R_5)_p$, —O—$C_{1-6}$alkyl-$(R)_p$, —$C_{1-6}$alkyl-O—$C_{1-6}$alkyl-$(R_5)_p$, —$NR_7$—$C_{1-6}$alkyl-$(R_5)_p$, or —$S(O)_m$—$C_{1-6}$alkyl-$(R_5)_p$;

$R_{1d}$ is Cl, F, methyl, $CF_3$ or cyano;

$R_2$ is —$C_{1-4}$alkyl-$(R_5)_p$;

$R_{2a}$ is phenyl substituted with 0-4 $R_3$, heteroaryl substituted with 0-4 $R_3$, $C_{1-6}$alkyl substituted with 0-4 $R_3$, aryl-$C_{1-4}$alkyl substituted with 0-4 $R_3$, or heteroaryl-$C_{1-4}$alkyl substituted with 0-4 $R_3$;

$R_3$ at each occurrence is independently halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-5}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$;

$R_4$ at each occurrence is independently halogen, $C_{1-6}$alkyl, halo$C_{1-4}$alkyl, $C_{1-6}$alkoxy, hydroxy, cyano, thio$C_{1-6}$alkyl, —$C(O)NR_7R_8$ or 5 member heteroaryl;

$R_5$ at each occurrence is independently H, hydroxy, —OC(O)—$C_{1-5}$alkyl, —OC(O)O—$C_{1-6}$alkyl, —OC(O)—$C_{1-6}$alkyl-$NR_7R_8$, —$COOR_6$, —$C(O)NR_7R_8$, —$NR_7C(O)$ $NR_7R_8$, —$S(O)_2NR_9R_9$, —$S(O)_m$—$C_{1-4}$alkyl, —$NR_7R_8$, $C_{1-6}$alkoxy, —O-heterocycle, or heterocycle wherein said heterocycle and said —O-heterocycle are substituted with 0-4 groups selected from halogen, $C_{1-6}$alkyl, $C_{1-4}$haloalkyl, hydroxy, oxo, thio, —$NH_2$, —$S(O)_2C_{1-4}$alkyl and —COOH;

$R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ at each occurrence is independently H, $C_{1-4}$alkyl, hydroxy, or heterocycle where said heterocycle is substituted with 0-4 groups selected from halogen, $C_{1-6}$alkyl, hydroxy, keto, —$NH_2$ and —COOH;

$R_8$ at each occurrence is independently H, $C_{1-4}$alkyl, halo$C_{1-4}$alkyl, —C(O)—$C_{1-4}$alkyl, —C(O)-halo$C_{1-4}$alkyl, —$S(O)_m$-halo$C_{1-4}$alkyl or —$S(O)_m$—$C_{1-4}$alkyl;

$R_9$ at each occurrence is independently H, $C_{1-4}$alkyl, or —$C(O)C_{1-4}$alkyl;

m is 0-2; and p at each occurrence is independently 1-3.

As used herein, the above terms have the following meaning:

"Alkyl" means a straight chain or branched, noncyclic or cyclic, unsaturated or saturated aliphatic hydrocarbon containing from 1 to 10 carbon atoms. The term "$C_{1-4}$alkyl" has the same meaning as alkyl but contains from 1 to 4 carbon atoms while the term "$C_{1-6}$alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atom replaced with an aryl moiety, such as —$CH_2$-phenyl, and the like.

"Heteroaryl" means an aromatic heterocycle ring of 5- to 10-members and having at least one heteroatom selected from nitrogen, oxygen and sulfur, and wherein the nitrogen and sulfur heteroatoms may be optionally oxidized, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, oxadiazolyl, thiadiazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

"Haloalkyl" means an alkyl group having at least one hydrogen atom replaced with a halogen, such as trifluoromethyl and the like.

"Halogen" means fluoro, chloro, bromo or iodo, typically fluoro or chloro.

"Hydroxy" means —OH.

"Oxo" means an oxygen double bonded to a carbon (means C=O).

"Thio" means a sulfur double bonded to a carbon (means C=S).

"Alkoxy" means an alkyl moiety attached through an oxygen bridge (i.e., —O-alkyl) and includes groups such as methoxy and ethoxy.

"Alkylthio" means an alkyl moiety attached through a sulfur bridge (i.e., —S-alkyl) and includes groups such as methylthio and ethylthio.

In an embodiment of the present invention, $R_{2a}$ is phenyl substituted with n $R_3$ groups as shown in structure (Ia):

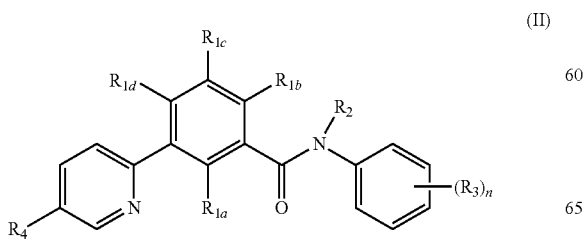

In embodiments of the present invention, A of structure (I) may be 2-pyridyl substituted with an $R_4$ group and $R_{2a}$ is phenyl substituted with n $R_3$ groups as shown in structure (II) and 3-pyridyl substituted in the 4 and 6 positions with $R_4$ and $R_{2a}$ is phenyl substituted with n $R_3$ groups as shown in structure (III).

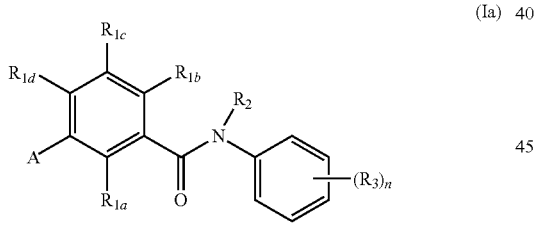

In an embodiment, A of structure (I) is quinolin-2-yl which may be substituted with two $R_4$ as shown in structure (IV), thienopyrimidinyl such as thieno[2,3-d]pyrimidin-4-yl as shown in structure (V), or 2-oxo-pyrimidinyl as shown in structure (VI).

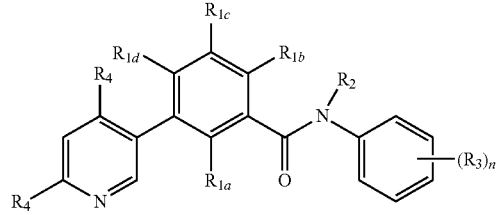

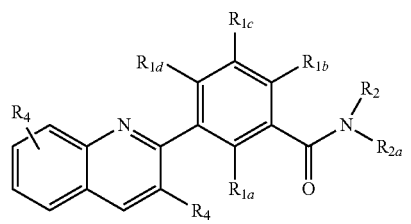

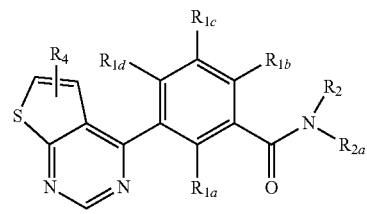

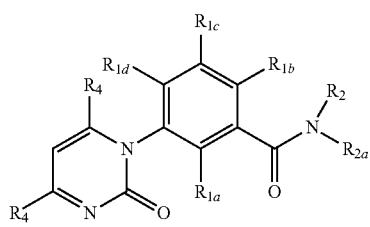

In an embodiment, $R_{2a}$ of structure (I) is substituted with $R_3$, where $R_3$ is —O—$C_{1-4}$alkyl-$(R_5)_p$ as shown in structure (VII). Structure (VII) shows $R_{2a}$ of structure (I) is phenyl, n is 1, and $R_3$ is —O-alkyl-$(R_5)_p$ where alkyl is 3 carbons and p is 2. The two $R_5$ may be the same or different. Structure (IX) shows and embodiment of structure (I) where $R_{1a}$ and $R_{1c}$ are H, $R_{1d}$ is Cl, and $R_{1b}$ is —O-alkyl-$(R_5)_p$.

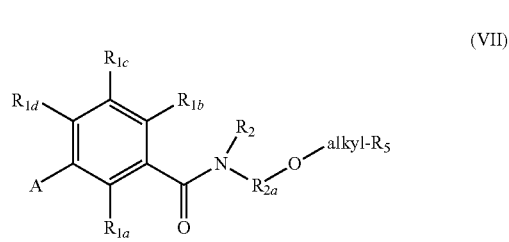

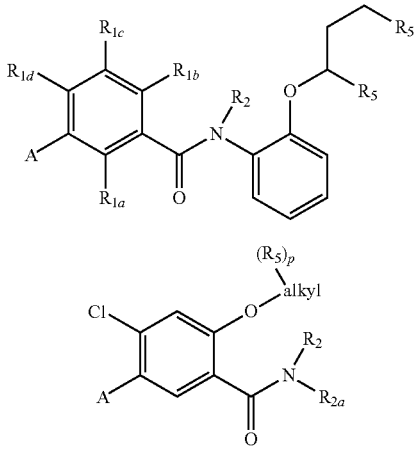

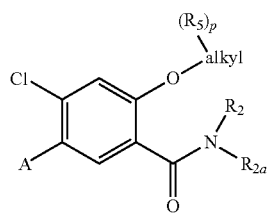

In an embodiment, A of structure (I) is 2-pyridyl substituted with 0-4 $R_4$.

In an embodiment, A of structure (I) is 2-pyridyl substituted with 2 $R_4$ groups at the 3 and 5 position.

In an embodiment, A of structure (I) is 3-pyridyl substituted with 0-4 $R_4$.

In an embodiment, A of structure (I) is 3-pyridyl substituted with 2 $R_4$ groups at the 4 and 6 position.

In a further embodiment, A of structure (I) is 4-cyano-6-trifluoromethylpyridin-3-yl.

In an embodiment, A of structure (I) is 3-cyano-5-fluoro-quinoline-2-yl.

In an embodiment, A of structure (I) is 3-cyano-5-trifluoromethyl-quinoline-2-yl.

In an embodiment, A of structure (I) is 3-cyano-[1,5]naphthyridin-2-yl.

In an embodiment, A of structure (I) is phenyl substituted with 0-4 $R_4$.

In an embodiment, $R_4$ is selected from halogen, haloalkyl, alkyl and cyano.

In an embodiment, A is substituted with 2 $R_4$ groups wherein each $R_4$ is independently selected from halogen cyano and trifluoromethyl.

$R_{1a}$ and $R_{1c}$, in an embodiment, are both H.

In an embodiment, $R_{1d}$ is Cl, F, $CF_3$ or methyl.

In an embodiment, $R_{1d}$ is Cl.

In an embodiment, $R_{1b}$ is H, hydroxy, —$C_{1-6}$alkyl-$(R)_p$, or —O—$C_{1-6}$alkyl-$(R_5)_p$.

In an embodiment, $R_{1b}$ is H, hydroxy, or —O—$C_{1-6}$alkyl-$(R_5)_p$ where $R_5$ at each occurrence is H.

In an embodiment, $R_{1b}$ is —O—$C_{1-6}$alkyl-$(R_5)_p$.

In an embodiment, $R_{1b}$ is —O—$C_{1-16}$alkyl-$(R_5)_p$ where —$C_{1-6}$alkyl- is —$C_{2-4}$alkyl-.

In an embodiment, $R_{1b}$ is —O—$C_{1-6}$alkyl-$(R_5)_p$ where —$C_{1-6}$alkyl- is —$CH_2CH_2CH_2$—.

In an embodiment, $R_{1b}$ is —O—$C_{1-6}$alkyl-$(R_5)_p$ where $R_5$ is hydroxy or —COOH.

In an embodiment, $R_{1b}$ is —O—$C_{1-6}$alkyl-$(R_5)_p$ where $R_5$ is H and p is 1.

In an embodiment, $R_2$ is —$C_{1-4}$alkyl-$(R_5)_p$ where $R_5$ at each occurrence is H.

In an embodiment, $R_{2a}$ is phenyl substituted with 0-4 $R_3$, heteroaryl substituted with 0-4 $R_3$, aryl-$C_{1-4}$alkyl substituted with 0-4 $R_3$, or heteroaryl-$C_{1-4}$alkyl substituted with 0-4 $R_3$.

In an embodiment, $R_{2a}$ is phenyl substituted with 0-4 $R_3$ or heteroaryl substituted with 0-4 $R_3$.

In an embodiment, $R_{2a}$ is phenyl substituted with 0-4 $R_3$ where $R_3$ is selected from halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$.

In an embodiment, $R_{2a}$ is a heteroaryl substituted with 0-4 $R_3$, where $R_3$ is selected from halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R)_p$.

In an embodiment, $R_{2a}$ is pyridyl substituted with 0-4 $R_3$ where $R_3$ is selected from halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$.

In an embodiment, $R_{2a}$ is a benzooxazole, or benzimidazole, or benzothiazole substituted with 0-4 $R_3$, where $R_3$ is selected from halogen, cyano, halo-$C_{1-4}$alkyl, $R_5$, —$C_{1-6}$alkyl-$(R)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m C_{1-6}$alkyl-$(R_5)_p$, —O—$C_{1-6}$alkyl-$NR_7$—$C_{1-6}$alkyl-$(R_5)_p$, heterocycle-$(R_5)$.

In an embodiment, $R_3$ is halogen, cyano, halo-$C_{1-4}$alkyl, —O—$C_{1-6}$alkyl-$(R_5)_p$, or heterocycle-$(R_5)_p$.

In an embodiment, $R_3$ is halogen, cyano, —O—$C_{1-6}$alkyl-$(R_5)_p$, or heterocycle-$(R_5)_p$.

In an embodiment, $R_3$, at one occurrence, is —O—$C_{1-6}$alkyl-$(R_5)_p$, where $R_5$ is H, hydroxy, —COOH or heterocycle where said heterocycle is substituted with 0-4 groups selected from halogen, $C_{1-4}$alkyl, $C_{1-4}$haloalkyl, hydroxy, oxo, thio, —$NH_2$, —$S(O)_2C_{1-4}$alkyl and —COOH.

In an embodiment, $R_3$, at one occurrence, is —O—$C_{1-6}$alkyl-$(R_5)_p$, where $R_5$ is OH or —COOH.

In an embodiment, $R_3$, at one occurrence is —O—$C_{1-6}$alkyl-$(R_5)_p$ where —$C_{1-6}$alkyl- is —$C_{2-3}$alkyl-.

In an embodiment, $R_3$, at one occurrence is —O—$C_{1-6}$alkyl-$(R_5)_p$ where —$C_{1-6}$alkyl- is —$CH_2CH_2$—.

In an embodiment, one of $R_{1b}$ and $R_3$ is —O—$C_{1-6}$alkyl-$(R_5)_p$, where $R_5$ is OH, —$COOR_6$ or heterocycle wherein said heterocycle is substituted with 0-4 groups selected from halogen, $C_{1-4}$alkyl, $C_{1-4}$haloalkyl, hydroxy, oxo, thio, —$NH_2$, —$S(O)_2C_{1-4}$alkyl and —COOH.

In an embodiment, one of $R_{1b}$ and $R_3$ is —O—$C_{1-6}$alkyl-$(R_5)_p$, where $R_5$ is OH or —COOH.

In an embodiment, $R_{1b}$ is —O—$C_{1-6}$alkyl-$(R_5)_p$, where $R_5$ is OH or —COOH; and $R_{2a}$ is phenyl substituted with 1-4 $R_3$, where $R_3$ is selected from halogen, cyano, $CF_3$, methoxy, methyl, or $CO_2R_6$.

In an embodiment, $R_{1b}$ is hydrogen and $R_{2a}$ is phenyl substituted with 1-2 $R_3$, where one $R_3$ is selected from O—$C_{1-6}$alkyl-$(R_5)_p$ and another $R_3$ is selected from hydrogen, halogen, cyano, $CF_3$, methoxy, or methyl.

In an embodiment, $R_{1b}$ is —O—$CH_3$ and $R_{2a}$ is phenyl substituted with 1-2 $R_3$, where one $R_3$ is selected from O—$C_{1-6}$alkyl-$(R_5)_p$ and another $R_3$ is selected from hydrogen, halogen, cyano, $CF_3$, methoxy, or methyl.

In an embodiment, $R_5$ is heterocycle and may be:

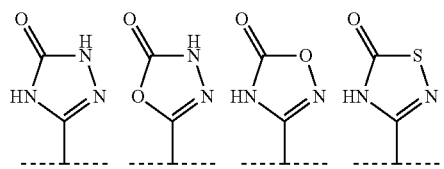

-continued

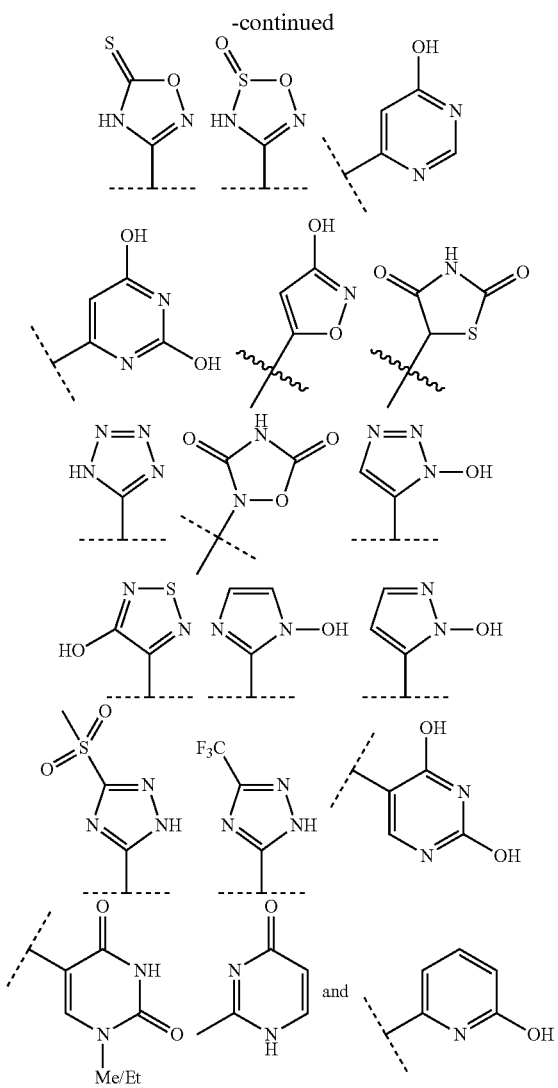

Representative compounds of the present invention include:
4-Chloro-3-(4-cyano-6-trifluoromethyl-pyridin-3-yl)-N-(2-methanesulfonyl-phenyl)-N-methyl-benzamide;
4-Chloro-3-(4-cyano-6-trifluoromethyl-pyridin-3-yl)-N-(2-hydroxy-6-methyl-phenyl)-N-methyl-benzamide;
4-Chloro-3-(4-cyano-6-trifluoromethyl-pyridin-3-yl)-N-[2-(2-hydroxy-ethoxy)-6-methyl-phenyl]-N-methyl-benzamide;
4-Chloro-(4-cyano-trifluoromethyl-pyridin-1-yl)-N-[2-(2-methoxy-ethoxy)-6-methyl-phenyl]-N-methyl-benzamide;
4-(2-{[4-Chloro-3-(3-cyano-6-fluoro-quinolin-2-yl)-benzoyl]-methyl-amino}-phenoxy)-butyric acid;
Acetic acid 2-(2-[4-chloro-3-(cyano-trifluoromethyl-pyridin-3-yl)-benzoyl]-methyl-amino)-3-methyl-phenoxy)-ethyl ester;
3-(5-Chloro-2-{[chloro-3-(4-cyano-trifluoromethyl-pyridin-3-yl)-benzoyl]-methyl-amino}-3-methyl-phenoxy)-propionic acid;
4-(2-{[4-Chloro-3-(4-cyano-6-fluoromethyl-pyridin-3-yl)-benzoyl]-methyl-amino}-3-methoxy-phenyl)-butyric acid methyl ester;
4-(2-{[4-Chloro-3-(4-cyano-6-trifluoromethyl-pyridin-3-yl)-benzoyl]-methyl-amino}-3-methoxy-phenyl)-butyric acid;
4-(2-{[4-Chloro-3-(4 methyl-6-trifluoromethyl-pyridin-3-yl)-benzoyl]-methyl-amino}-3-methoxy-phenyl)-butyric acid;
4-Chloro-2-(3-dimethylamino-propoxy)-N-(2-methoxy-6-methyl-phenyl)-N-methyl-5-(4-methyl-8-trifluoromethyl-pyridin-3-yl)-benzamide;
4-[5-Chloro-2-[(2-methoxy-6-methyl-phenyl)-methyl-carbamoyl]-4-(4-methyl-6-trifluoromethyl-pyridin-3-yl)-phenoxy]-butyric acid ethyl ester;
4-{5-chloro-4-(4-cyano-6-trifluoromethyl-pyridin-3-yl)-2-[(2-methoxy-phenyl)-methyl-carbamoyl]-phenoxy}-butyric acid;
3-{5-chloro-4-(4-cyano-6-trifluoromethyl-pyridin-3-yl)-2-[(2-methoxy-phenyl)-methyl-carbamoyl]-phenoxy}-propionic acid;
{5-chloro-4-(4-cyano-6-trifluoromethyl-pyridin-3-yl)-2-[(2-methoxy-phenyl)-methyl-carbamoyl]-phenoxy}-acetic acid;
4-chloro-5-(4-cyano-6-trifluoromethyl-pyridin-3-yl)-2-(4-hydroxy-butoxy)-N-(2-methoxy-phenyl)-N-methyl-benzamide;
4-chloro-5-(4-cyano-6-trifluoromethyl-pyridin-3-yl)-2-(3-hydroxy-propoxy)-N-(2-methoxy-phenyl)-N-methyl-benzamide;
4-chloro-5-(4-cyano-6-trifluoromethyl-pyridin-3-yl)-2-(2-hydroxy-ethoxy)-N-(2-methoxy-phenyl)-N-methyl-benzamide;
4-chloro-5-(4-cyano-6-trifluoromethyl-pyridin-3-yl)-2-(3-hydroxy-propyl)-N-(2-methoxy-phenyl)-N-methyl-benzamide;
4-chloro-5-(4-cyano-6-trifluoromethyl-pyridin-3-yl)-2-(3-hydroxy-propyl)-N-(2-methoxy-6-methyl-phenyl)-N-methyl-benzamide;
3-{5-chloro-4-(4-cyano-6-trifluoromethyl-pyridin-3-yl)-2-[(2-methoxy-phenyl)-methyl-carbamoyl]-phenyl}-propionic acid;
3-{5-Chloro-4-(4-cyano-6-trifluoromethyl-pyridin-3-yl)-2-[(2-methoxy-6-methyl-phenyl)-methyl-carbamoyl]-phenyl}-propionic acid;
4-chloro-5-(4-cyano-6-trifluoromethyl-pyridin-3-yl)-2-(2-hydroxy-ethylsulfanyl-N-(2-methoxy-phenyl)-N-methyl-benzamide;
4-chloro-5-(4-cyano-6-trifluoromethyl-pyridin-3-yl)-2-(2-hydroxy-ethylsulfanyl)(2-methoxy-6-methylphenyl)-N-methyl-benzamide;
{5-chloro-4-(4-cyano-6-trifluoromethyl-pyridin-3-yl)-2-[(2-methoxy-phenyl)-methyl-carbamoyl]-phenylsulfanyl}-acetic acid;
{5-chloro-4-(4-cyano-6-trifluoromethyl-pyridin-3-yl)-2-[(2-methoxy-1-methyl-phenyl)-methyl-carbamoyl]-phenylsulfanyl}-acetic acid;
4-chloro(4,6-dicyano-pyridin-3-yl)-2-(2-hydroxy-ethoxy)-N-(2-methoxy-phenyl)-N-methyl-benzamide
4-chloro-(4,6-dicyano-pyridin-3-yl)-2-(2-hydroxy-ethoxy)-N-(2-methoxy-6-methyl-phenyl)-N-methyl-benzamide;
4-chloro-5-(4,6-dicyano-pyridin-3-yl)-2-(3-hydroxy-propoxy)-N-(2-methoxy-phenyl)-N-methyl-benzamide;
4-chloro-5-(4,6-dicyano-pyridin-3-yl)-2-(3-hydroxy-propoxy)-N-(2-methoxy-6-methyl-phenyl)-N-methyl-benzamide;
4-{5-chloro-4-(4,6-dicyano-pyridin-3-yl)-2-[(2-methoxy-phenyl)-methyl-carbamoyl]-phenoxy}-butyric acid;
4-{5-chloro-4-(4,6-dicyano-pyridin-3-yl)-2-[(2-methoxy-6-methyl-phenyl)-methyl-carbamoyl]-phenoxy}-butyric acid;

[5-chloro-2-[(2-methoxy-phenyl)-methyl-carbamoyl]-4-(4-prop-1-ynyl-6-trifluoromethyl-pyridin-3-yl)-phenoxy]-acetic acid;

3-[5-chloro-2-[(2-methoxy-phenyl)-methyl-carbamoyl]-4-(4-prop-1-ynyl-8-trifluoromethyl-pyridin-3-yl)-phenoxy]-propionic acid;

4-[5-chloro-2[(2-methoxy-phenyl-methyl-carbamoyl]-4-(4-prop-1-ynyl-6-trifluoromethyl-pyridin-3-yl)-phenoxy]-butyric acid;

3-(2-{[4-chloro-3-(4-prop-1-ynyl-8-trifluoromethyl-pyridin-3-yl)-benzoyl]-methyl-amino)-phenoxy}-propionic acid;

4-(2-{[4-chloro-3-(4-ethynyl-6-trifluoromethyl-pyridin-3-yl)-benzoyl]-methyl-amino}-phenoxy)-butyric acid;

4-(2-{[4-chloro-3-(4-prop-1-ynyl-6-trifluoromethyl-pyridin-3-yl)-benzoyl]-methyl-amino}-phenoxy)-butyric acid;

4-(2-{[4-chloro-3-(4-ethynyl-6-trifluoromethyl-pyridin-3-yl)-benzoyl]-methyl-amino}-phenoxy)-butyric acid;

3-(2-{[4-Chloro-3-(4,6-dicyano-pyridin-3-yl)-benzoyl]-methyl-amino}-phenoxy)-propionic acid;

3-(2-{[4-Chloro-3-(4-ethynyl-6-trifluoromethyl-pyridin-3-yl)-benzoyl]-methyl-amino}-phenoxy)-propionic acid;

3-(2-{[4-Chloro-3-(4-cyano-6-trifluoromethyl-pyridin-3-yl)-benzoyl]-methyl-amino}-phenylamino)-propionic acid;

4-(2-{[4-Chloro-3-(4-cyano-6-trifluoromethyl-pyridin-3-yl)-benzoyl]-methyl-amino}-phenylamino)-butyric acid;

3-(2-{[4-Chloro-3-(4-cyano-6-trifluoromethyl-pyridin-3-yl)-benzoyl]-methyl-amino}-phenoxy)-propionic acid 1-isopropoxycarbonyloxy-ethyl ester;

3-(2-{[4-Chloro-(4-cyano-6-trifluoromethyl-pyridin-3-yl)-2-methoxy-benzoyl]-methyl-amino}-phenoxy)-propionic acid;

3-(2-{[4-Chloro-3-(4-cyano-6-trifluoroethyl-pyridin-3-yl)-benzoyl]-methyl-amino}-3-fluoro-phenoxy)-propionic acid;

3-(2-{[4-Chloro-5-(4-cyano-6-trifluoromethyl-pyridin-3-yl)-2-methoxy-benzoyl]-methyl-amino}-3-fluoro-phenoxy)-propionic acid;

3-(3-Chloro-2-{[4-chloro-(4-cyano-6-trifluoromethyl-pyridin-3-yl)-benzoyl]-methyl-amino}-phenoxy)-propionic acid;

3-(3Chloro-2-{[4-chloro-4-cyano-6-trifluoromethyl-pyridin-3-yl)-2-methoxy-benzoyl]-methyl-amino}-phenoxy)-propionic acid;

3-(2-{[4-Chloro-3-(4-cyano-trifluoromethyl-pyridin-3-yl)-benzoyl]-methyl-amino}-3-cyano-phenoxy)-propionic acid;

3-(2-{[4-Chloro-5-(4-cyano-6-trifluoromethyl-pyridin-3-yl)-2-methoxy-benzoyl]-methyl-amino}-3-cyano-phenoxy)-propionic acid;

4-Chloro-3-(4-cyano-6-trifluoromethyl-pyridin-3-yl)-N-{2-fluoro-6-[2-(5-oxo-4,5-dihydro-[1,3,4]oxadiazol-2-yl)-ethoxy]-phenyl}-N-methyl-benzamide;

4-Chloro-(4-cyano-6-trifluoromethyl-pyridin-3-yl)-N-{2-fluoro-2-(5-oxo-4,5-dihydro-[1,3,4]oxadiazol-2-yl)-ethoxy)-phenyl}-2-methoxy-N-methyl-benzamide;

4-Chloro-N-{2-chloro-6-[2-(5-oxo-4,5-dihydro-[1,3,4]oxadiazol-2-yl)-ethoxy]-phenyl}-3-(4-cyano-6-trifluoromethyl-pyridin-3-yl)-N-methyl-benzamide;

4-Chloro-N-{2-chloro-6-[2-(5-oxo-4,5-dihydro-[1,3,4]oxadiazol-2-yl)-ethoxy]-phenyl}-5-cyano-6-trifluoromethyl-pyridin-3-yl)-2-methoxy-N-methyl-benzamide;

4-Chloro-N-{2-cyano-6-[2-(5-oxo-4,5-dihydro-[1,3,4]oxadiazol-2-yl)-ethoxy]-phenyl}-3-(4-cyano-6-trifluoromethyl-pyridin-3-yl)-N-methyl-benzamide;

4-Chloro-N-{2-cyano-6-[2-(5-oxo-4,5-dihydro-[1,3,4]oxadiazol-2-yl)-ethoxy]-phenyl}-5-(4-cyano-6-trifluoromethyl-pyridin-3-yl)-2-methoxy-N-methyl-benzamide;

4-Chloro-N-{2-chloro-6-[2-(1H-tetrazol-5-yl)-ethoxy]-phenyl}-3-(4-cyano-6-trifluoromethyl-pyridin-3-yl)-N-methyl-benzamide;

4-Chloro-N-{2-chloro-6-[2-(1H-tetrazol-5-ethoxy]-phenyl}-5-(4-cyano-6-trifluoromethyl-pyridin-3-yl)-2-methoxy-N-methyl-benzamide;

4-Chloro-N-{2-cyano-6-[2-(1H-tetrazol-5-yl)-ethoxy]-phenyl}-3-(4-cyano-6-trifluoromethyl-pyridin-3-yl)-N-methyl-benzamide;

4-Chloro-N-{[2-cyano-6-(2-(1H-tetrazol-5-yl)-ethoxy]-phenyl}-5-(4-cyano-6-trifluoromethyl-pyridin-3-yl)-2-methoxy-N-methyl-benzamide;

4-Chloro-3-(4-cyano-6-trifluoromethyl-pyridin-3-yl)-N-{2-fluoro-6-[2-(5-oxo-4,5-dihydro-1H-[1,2,4]thiazol-3-yl)-ethoxy]-phenyl}-N-methyl-benzamide;

4-Chloro-5-(4-cyano-6-trifluoromethyl-pyridin-3-yl)-N-{2-fluoro-6-[2-(5-oxo-4,5-dihydro-1H-[1,2,4]triazol-3-yl)-ethoxy]-phenyl}-2-methoxy-N-methyl-benzamide;

4-Chloro-N-{2-chloro-6-[2-(5-oxo-4,5-dihydro-1H-[1,2,4]-triazol-3-yl)-ethoxy]-phenyl}3-(4-cyano-6-trifluoromethyl-pyridin-3-yl)-N-methyl-benzamide;

4-Chloro-N-{2-chloro-6-[2-(5-oxo-4,5-dihydro-1H-[1,2,4]triazol-3-yl)-ethoxy]-phenyl}-5-(4-cyano-6-trifluoromethyl-pyridin-3-yl)-2-methoxy-N-methyl-benzamide;

4-Chloro-N-{2-cyano-6-[2-(5-oxo-4,5-dihydro-1-H-[1,2,4]-triazol-3-yl)-ethoxy]-phenyl}-3-(4-cyano-6-trifluoromethyl-pyridin-3-yl)-N-methyl-benzamide;

4-Chloro-N-{2-cyano-6-[2-(5-oxo-4,5-dihydro-1H-[1,2,4]triazol-3-yl)-ethoxy]-phenyl}-5-(4-cyano-6-trifluoromethyl-pyridin-3-yl)-2-methoxy-N-methyl-benzamide;

4-[5-Chloro-2-[(2-chloro-6-methoxy-phenyl)-methyl-carbamoyl]-4-(4-cyano-6-trifluoromethyl-pyridin-3-yl)-phenoxy]-butyric acid;

4-[5-Chloro-2-[(2-cyano-6-methoxy-phenyl)-methyl-carbamoyl]-4-(4-cyano-6-trifluoromethyl-pyridin-3-yl)-phenoxy]-butyric acid;

4-Chloro-5-(4-cyano-6-trifluoromethyl-pyridin-3-yl)-N-(2-fluoro-6-methoxy-phenyl)-N-methyl-2-[3-(1H-tetrazol-5-yl)-propoxy]-benzamide;

4-Chloro-N-(2-chloro-6-methoxy-phenyl)-5-(4-cyano-6-trifluoromethyl-pyridin-3-yl)-N-methyl-2-[3-(1H-tetrazol-5-yl)-propoxy]-benzamide;

4-{5-Chloro-4-(3-cyano-5-trifluoromethyl-quinolin-2-yl)-2-[(2-methoxy-phenyl)-methyl-carbamoyl]-phenoxy}-butyric acid;

4-{5-Chloro-4-(3-cyano-5-trifluoromethyl-quinolin-2-yl)-2-[(2-fluoro-6-methoxy-phenyl)-methyl-carbamoyl]-phenoxy}-butyric acid;

4-[5-Chloro-2-[(2-chloro-6-methoxy-phenyl)-meth-carbamoyl]-4-(3-cyano-5-trifluoromethyl-quinolin-2-yl)-phenoxy]-butyric acid;

3-(2-{[4-Chloro-5-(3-cyano-5-trifluoromethyl-quinolin-2-yl)-2-methoxy-benzoyl]-methyl-amino}-3-fluoro-phenoxy)-propionic acid;

3-(3-Chloro-2-{[4-chloro-5-(3-cyano-5-trifluoromethyl-quinolin-2-yl)-2-methoxy-benzoyl]-methyl-amino}-phenoxy)-propionic acid;

3-(2-{[4-Chloro-5-(3-cyano-5-trifluoromethyl-quinolin-2-yl)-2-methoxy-benzoyl]-methyl-amino}-phenoxy)-propionic acid;

3-(2-{[4-Chloro-3-(3-cyano-5-trifluoromethyl-quinolin-2-yl)-benzoyl]-methyl-amino}-phenoxy)propionic acid;

2-{[4-Chloro-3-(4-cyano-6-trifluoromethyl-pyridin-3-yl)-benzoyl]-methyl-amino}-3-fluoro-benzoic acid methyl ester;

2-{[4-Chloro-3-(4-cyano-6-trifluoromethyl-pyridin-3-yl)-benzoyl]-methyl-amino}-3-fluoro-benzoic acid ethyl ester;

3-Chloro-2-{[4-chloro-3-(4-cyano-6-trifluoromethyl-pyridin-3-yl)-benzoyl]-methyl-amino}-benzoic acid methyl ester;

3-Chloro-2-{[4-chloro-(4-cyano-6-trifluoromethyl-pyridin-3-yl)-benzoyl]-methyl-amino}-benzoic acid ethyl ester;

3-(2-{[4-Chloro-3-(4-cyano-6-trifluoromethyl-pyridin-3-yl)-benzoyl]-methyl-amino}-phenoxy)-2-hydroxy-propionic acid;

2-Amino-3-(2-{[4-chloro-3-(4-cyano-6-trifluoromethyl-pyridin-3-yl)-benzoyl]-methyl-amino}-phenoxy)-propionic acid;

(7-{[4-Chloro-3-(4-cyano-6-trifluoromethyl-pyridin-3-yl)-benzoyl]-methyl-amino}-benzooxazol-2-yl)-acetic acid;

(7-{[4-Chloro-5-(4-cyano-trifluoromethyl-pyridin-3-yl)-2-methoxy-benzoyl]-methyl-amino}-benzooxazol-2-yl)-acetic acid;

3-(7-{[4-Chloro-3-(4-cyano-6-trifluoromethyl-pyridin-3-yl)-benzoyl]-methyl-amino}-benzooxazol-2-yl)-propionic acid;

3-(7-{[4-Chloro-5-(4-cyano-6-trifluoromethyl-pyridin-3-yl)-2-methoxy-benzoyl]-methyl-amino}-benzooxazol-2-yl)-propionic acid;

3-{5-Chloro-4-(4-cyano-6-trifluoromethyl-pyridin-3-yl)-2-[(2-methoxy-phenyl)-methyl-carbamoyl]-phenoxy}-2-hydroxy-propionic acid;

2-Amino-3-{5-chloro-4-(4-cyano-6-trifluoromethyl-pyridin-3-yl)-2-[(2-methoxy-phenyl)-methyl-carbamoyl]-phenoxy}-propionic acid; and 4-{5-Chloro-4-(4-cyano-6-trifluoromethyl-pyridin-3-yl)-2-[(2-methoxy-phenyl)-methyl-carbamoyl]-phenoxy}-3-hydroxy-butyric acid.

The representative compound list above also is meant to include pharmaceutically acceptable salts of the compounds listed.

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

Scheme 1

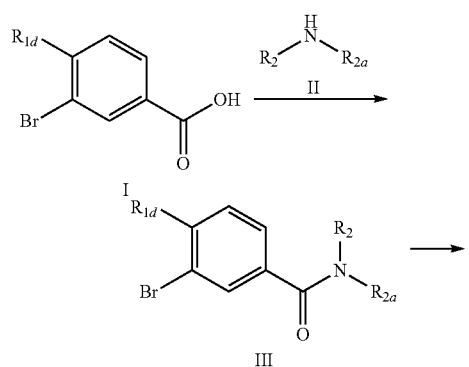

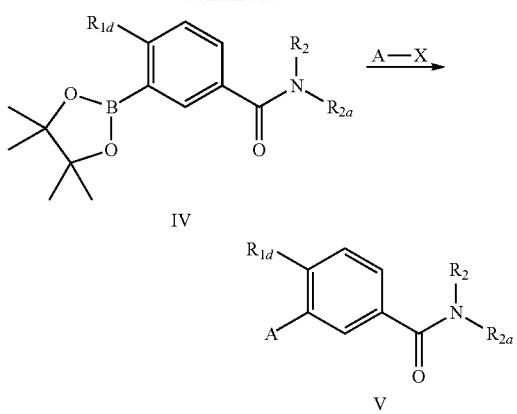

A 3-bromobenzoic acid (I) is converted into the corresponding acyl chloride, then is coupled with HN(R$_2$)R$_{2a}$ (II) to form the amide (III). Alternatively, (III) can be prepared by a coupling reaction of (I) with (II) in presence of an activating reagent such as HBTU. Where R$_2$ of (II) is a hydrogen, the additional N-alkylation step may be carried out in DMF with strong base such as sodium hydride and R$_2$X (X=Br, I). (III) was then transformed into the boronic ester (IV) through a palladium (0) catalyzed reaction. Suzuki reaction of (IV) with a suitable aryl or heteroaryl halide (A-X) produces the desired product (V). Examples of suitable aryl or heteroaryl groups are described for A in Scheme 1.

Scheme 2

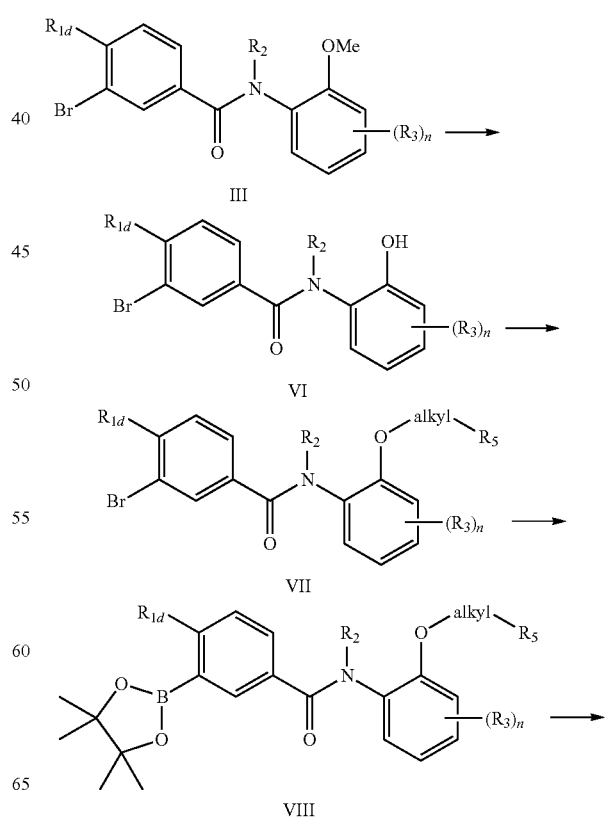

15

-continued

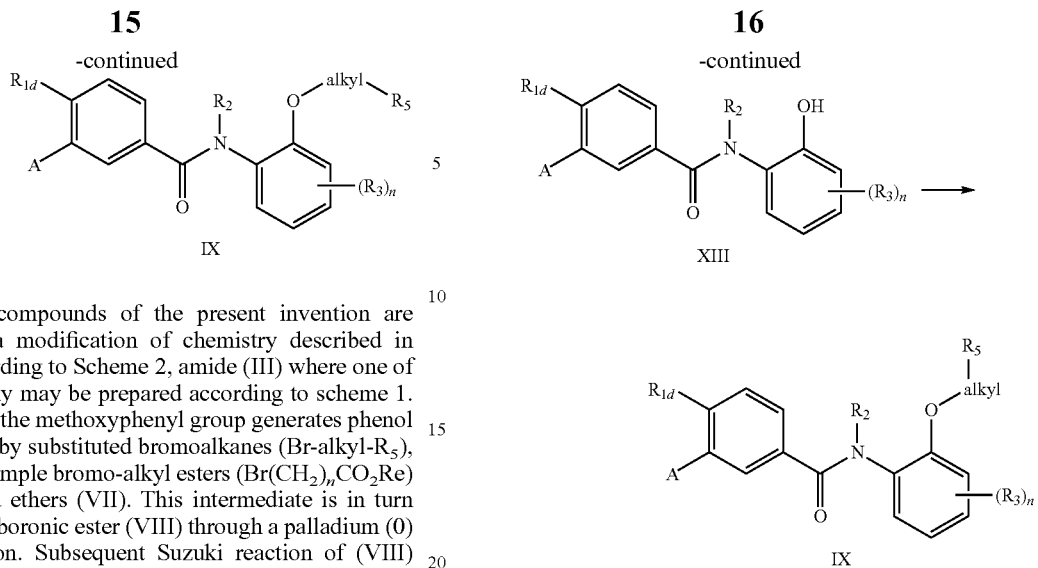

IX

Additionally compounds of the present invention are prepared from a modification of chemistry described in Scheme 1. According to Scheme 2, amide (III) where one of the $R_3$ is methoxy may be prepared according to scheme 1. De-alkylation of the methoxyphenyl group generates phenol (VI). Alkylation by substituted bromoalkanes (Br-alkyl-$R_5$), including for example bromo-alkyl esters (Br(CH$_2$)$_n$CO$_2$Re) gives substituted ethers (VII). This intermediate is in turn converted to the boronic ester (VIII) through a palladium (0) catalyzed reaction. Subsequent Suzuki reaction of (VIII) with a suitable aryl or heteroaryl halide produces (IX). Alternatively, an appropriate aryl or hetaryl boronic acid may be coupled with (VII) under Suzuki conditions to yield (IX).

16

-continued

XIII

IX

Alternatively, compounds of the general formula (IX) may also be prepared from the phenol (VI). As is shown in Scheme 4, the palladium (0) reaction is first conducted to generate the boron ester (XII). This intermediate is in turn subjected to Suzuki conditions with various aryl bromides to yield the phenols (XIII). Subsequently alkylation of the phenolic group provides compounds of the general structure (IX).

Scheme 3

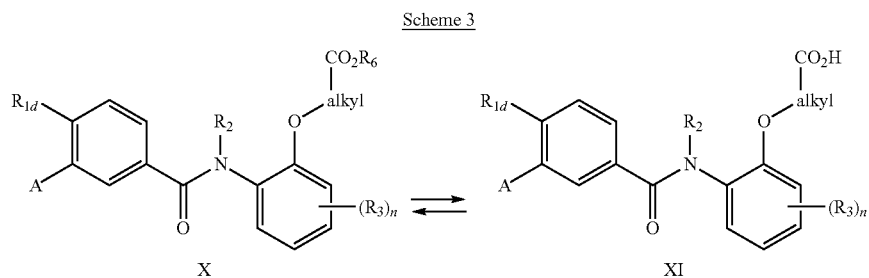

X ⇌ XI

In the case where the substituent $R_5$ is represented by a carboxylic acid ester (X), deprotection of the ester using acid or base conditions is used to produce the free carboxylic acid (XI) as depicted in Scheme 3. Compounds of general formula (X) may conversely be prepared by esterification of acids (XI) as required.

Scheme 4

Scheme 5

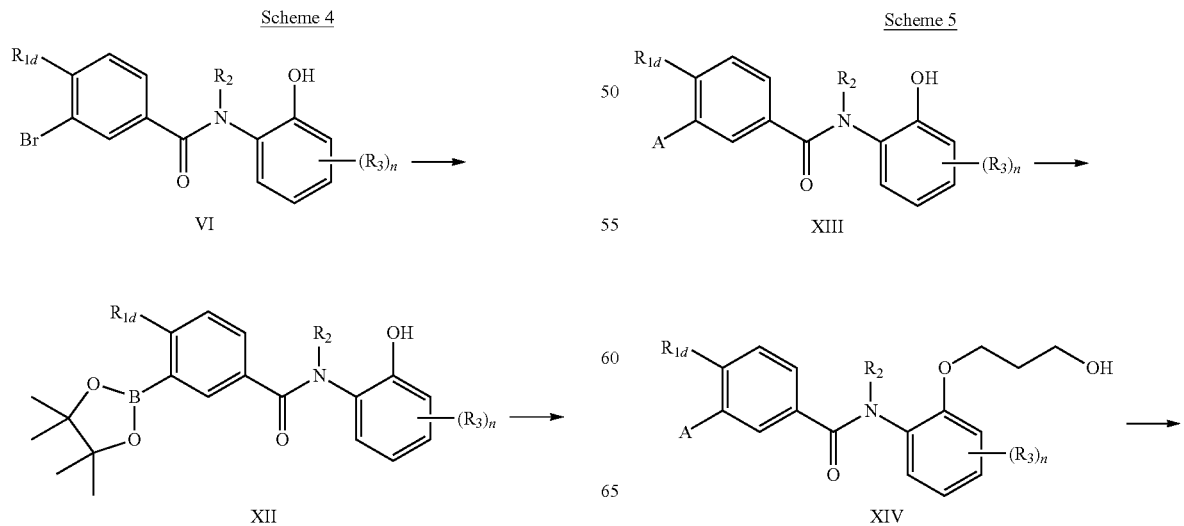

VI

XIII

XII

XIV

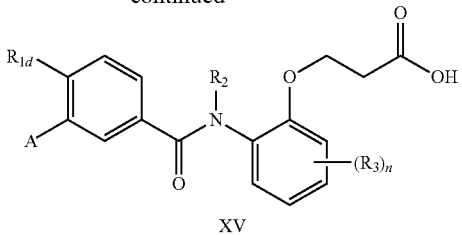

An alternative synthesis of compounds of formula (IX) is described in Scheme 5. In this case, phenol (XIII) is alkylated with 3-bromopropanol to give (XIV). Oxidation of the alcohol yields the carboxylic acid (XV).

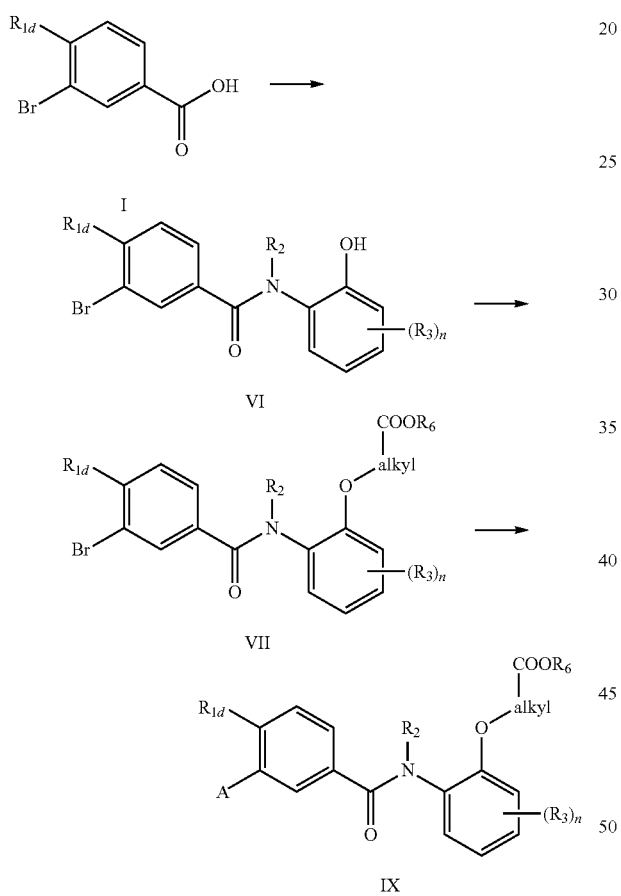

Alternatively, (VI) may be obtained by reaction of the acyl chloride, generated in situ from the acid (I), with a N-substituted hydroxyaniline as is described in Scheme 6. Intermediate (VI) is alkylated by the corresponding substituted alkyl bromide such as bromo-alkyl ester (Br-alkyl-$COOR_6$) to yield the ether (VII), which may be further elaborated to compounds of formula (IX) as previously described in Scheme 2. In Scheme 6, the amide (VI) may either be prepared as described or synthesized from a suitably substituted 2-aminocresol ($R_2$=H). Alkylation of the amide nitrogen may be performed at a later stage in the reaction sequence. Typically for the case where the $R_2$ group is a hydrogen, the additional N-alkylation step is carried out in DMF with strong base such as sodium hydride and $R_2X$ (X=Br, I) on the intermediate (VII) before completing the additional steps in the reaction sequence.

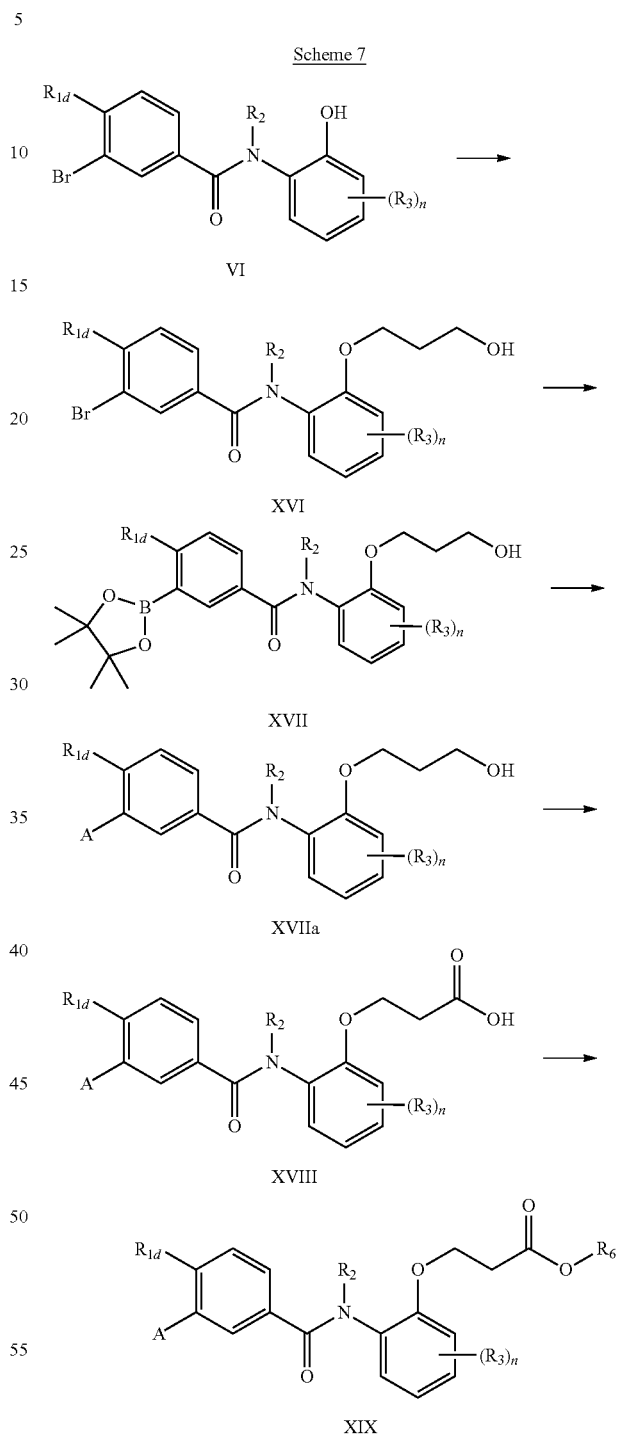

Intermediate phenol (VI) is alkylated with 3-bromopropanol. The intermediate bromide (XVI) is converted to the corresponding boronic ester (XVII). Suzuki reaction with suitable aryl or heteroaryl halide gives the alcohol (XVIIa). This derivative may be subsequently oxidized to yield the acid (XVIII). Optionally the acid may be converted to its alkyl ester (XIX) directly from the acid.

Scheme 8

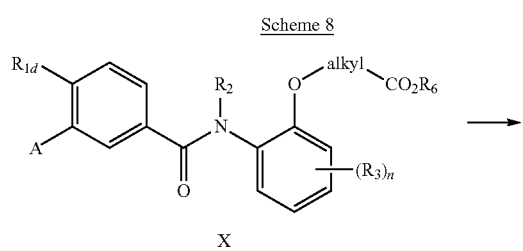

In a further elaboration of Scheme 3, esters (where $R_6$ is, for instance, methyl or ethyl) may be subjected to aminolysis to give the amide XX.

Scheme 9

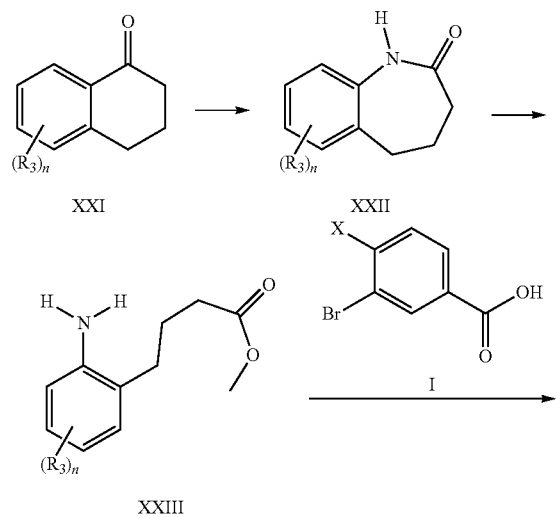

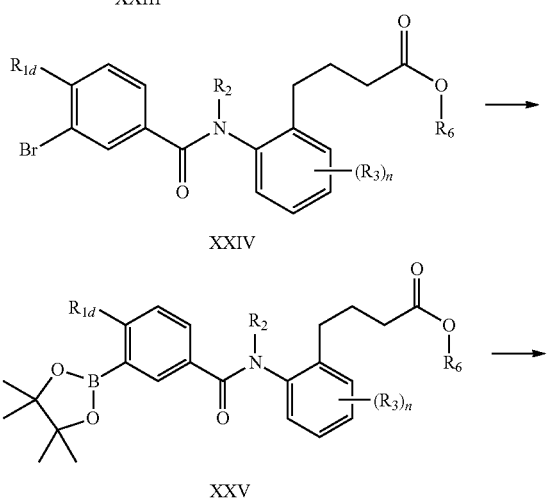

α-Tetralone (XXI) is converted into the corresponding lactam (XXII) and then opened to form the aniline methyl ester (XXIII). This aniline was coupled to benzoyl chloride formed from the acid (I, see also Scheme 1) to generate the amide (XXIV, $R_2$=H). A subsequent N-alkylation step is carried out in DMF with strong base such as sodium hydride and $R_2X$ (X=Br, I) to give the fully substituted (XXIV, $R_2$=alkyl, $R_6$=methyl). Bromide (XXIV) is then transformed into the boronic ester (XXV) through a palladium (0) catalyzed reaction. Suzuki reaction with a suitable aryl or heteroaryl halide yields the ester (XXVI). The ester may be converted to the acid (XXVII) as necessary. In cases where the "A" group introduced is sensitive to the deprotection conditions necessary to remove the methyl ester, the ester substitution $R_6$ may be changed when required. In this respect, ester (XXIV) is first deprotected under conditions of basic hydrolysis before re-esterification with a suitable alcohol (exemplified by $R_6$=tert-butyl). The final steps in Scheme 9 remain constant for both intermediates.

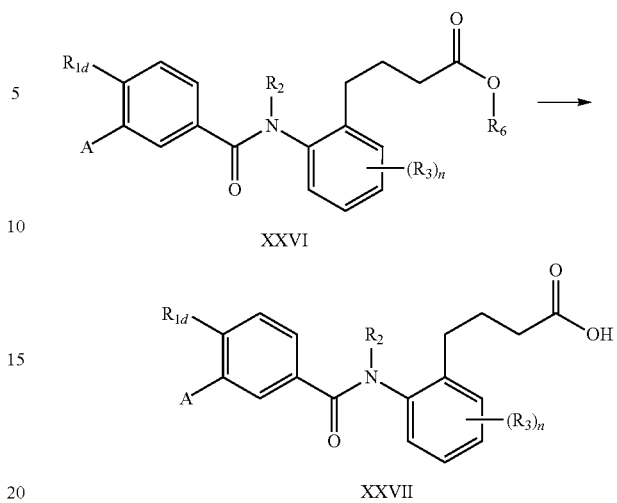

Scheme 10

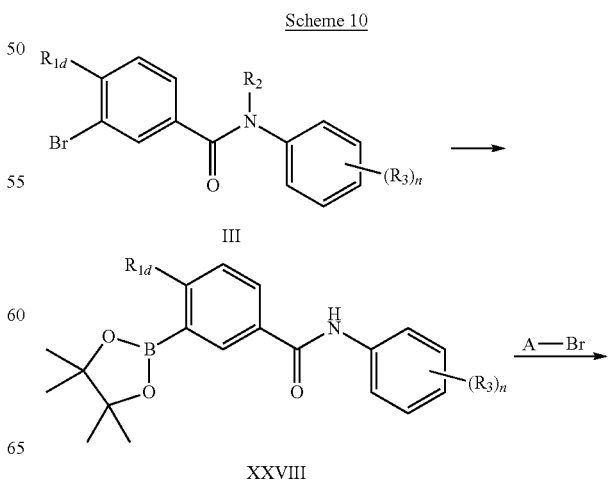

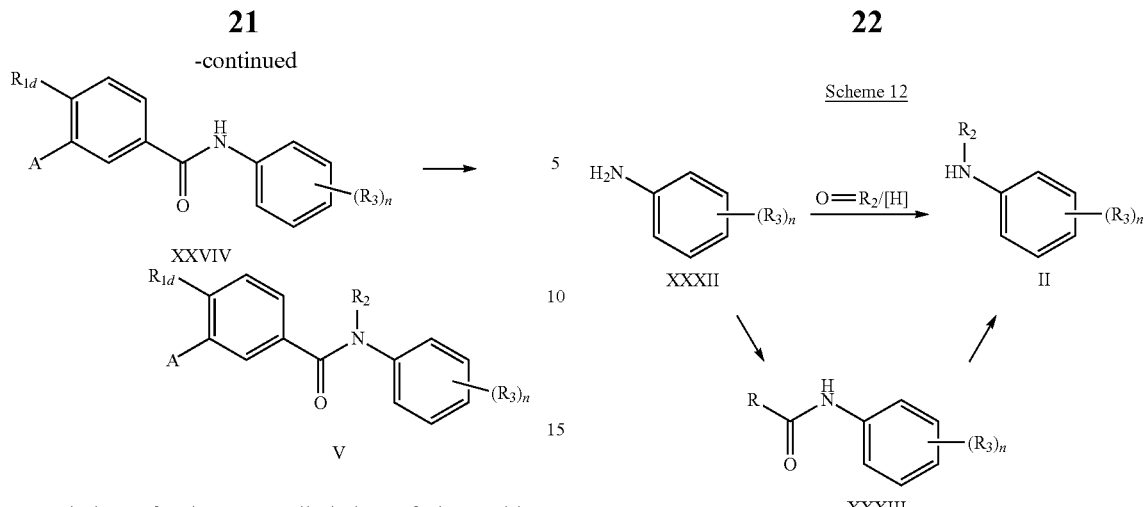

In a variation of scheme 1, alkylation of the amide nitrogen may be delayed to facilitate diversification of the substitution at this position. Thus, as is described in Scheme 10, amide (III) may be converted first to the boron ester (XXVIII) and then to the intermediate (XIV) via the Suzuki protocol. Alkylation of the amide nitrogen is effected by reaction with a suitable electrophilic reagent in the presence of strong base to yield the fully substituted product (V).

Synthesis of appropriately substituted aniline (II) may be directly accomplished by reductive amination of the primary aniline (XXXII) with a carbonyl equivalent such as aldehyde, ketone or substituted ketal, or via a 2-step route involving direct acylation. In this case, the intermediate

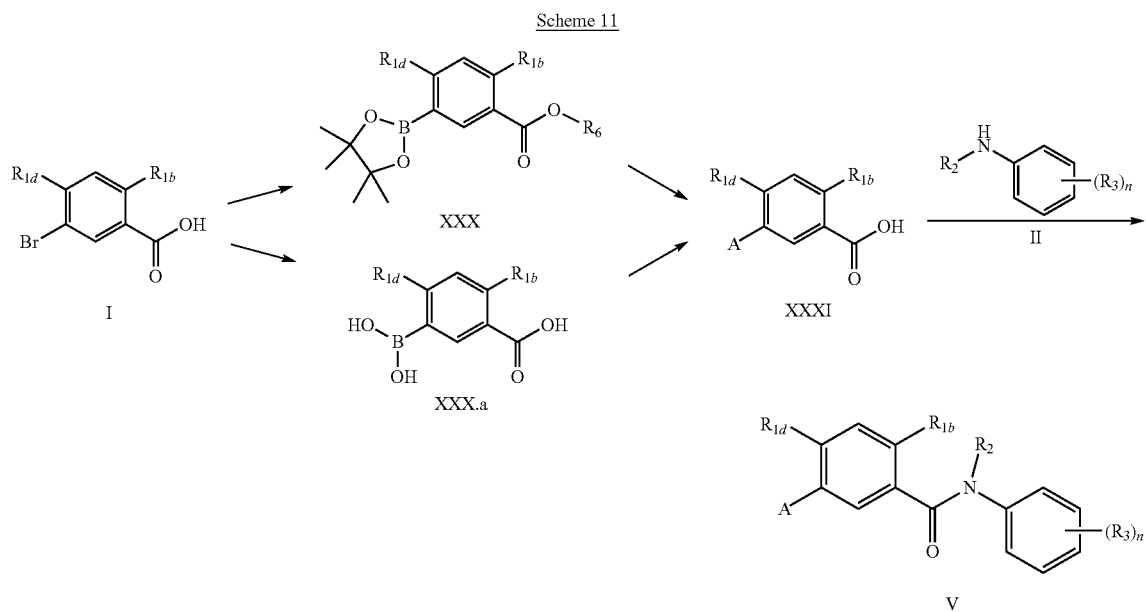

In a modification of Scheme 1, the palladium coupling reactions may be performed earlier in the reaction sequence. Thus, benzoic acid (I) is first transformed to its carboxylic ester and then converted to the boron ester (XXX). This intermediate is subjected to Suzuki coupling conditions resulting in compound (XXXI) after ester hydrolysis. Alternatively, commercially available (XXX.a) maybe used to produce XXXI in one step via Suzuki coupling reaction. The acid (XXXI) is activated as the acid chloride in situ and coupled with anilines of general structure (II) to obtain the amides (V). When $R_2$ is hydrogen, a subsequent N-alkylation step may be carried out in DMF with strong base such as sodium hydride and $R_2X$ (X=Br, I) to give (V).

(XXXIII, R is H, alkyl or substituted alkyl) is reduced with, for instance, lithium aluminum hydride to generate the desired product.

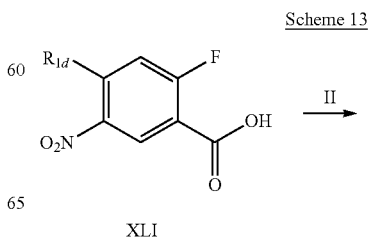

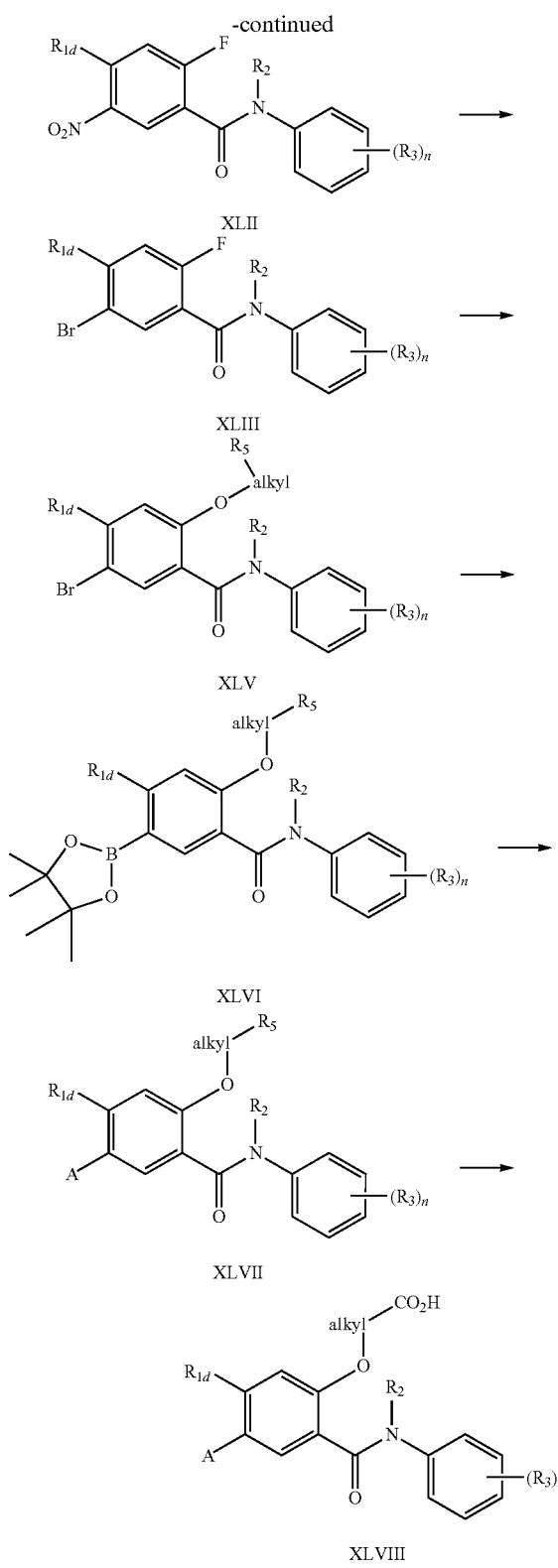

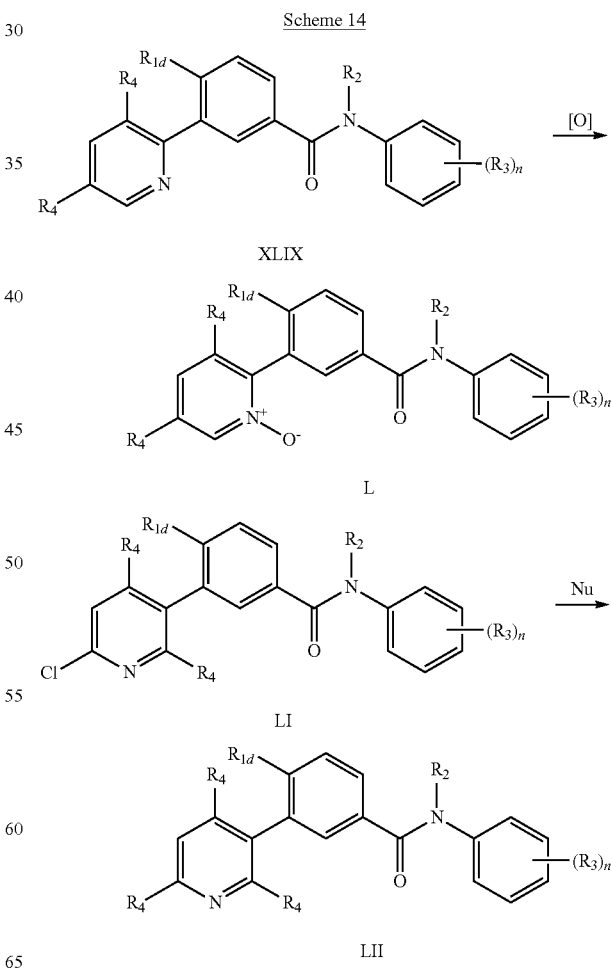

additional N-alkylation using an alkyl halide [$R_2X$ (X=Br, I)] is carried out under conditions such as in DMF with a strong base such as sodium hydride. (XLII) is then transformed into the bromide (XLIII) by initial reduction of the nitro function followed by a diazotization of the aniline in the presence of copper (II) bromide. (XLV) may be prepared in several ways including substituting the fluoro group of (XLIII) by using an appropriately substituted alcohol directly to insert the alkyl side chain. Alternatively, the substitution is performed with sodium methoxide to generate the methoxy derivative. De-methylation of this methoxy compound is generally accomplished with $BBr_3$ to facilitate preparation of the phenol which may be subsequent alkylated with a substituted alkyl bromide (exemplified by Br-alkyl-$R_5$) to yield the intermediate (XLV). Bromide (XLV) may be used in a palladium (0) catalyzed reaction to give the boron ester (XLVI). Under Suzuki conditions this ester could be reacted with a suitable aryl or heteroaryl halide to yield (XLVII). Compounds of general structure (XLVII, $R_5$ is —$COOR_6$) may be converted to the (XLVIII) by deprotection of the ester under acidic or basic conditions. Alternately, oxidation of the corresponding alcohol (XLVII, $R_5$ is hydroxy) may also yield structure (XLVIII). In all cases, as required, the acid could be re-converted to a suitable ester as previously described.

Scheme 14

4-Substituted-2-fluoro 3-nitro-benzoic acid (XLI) is converted into the corresponding acyl chloride and is coupled with a substituted aniline (II) to form the amide (XLII). Alternatively, (XLII) can be prepared by a coupling reaction of (XLI) with (II) in the presence of an activating reagent such as HBTU. When the $R_2$ group of (II) is hydrogen, an -continued

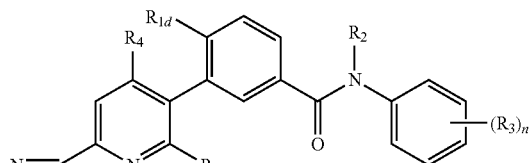

LIII

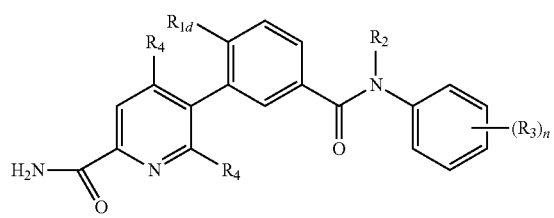

LIV

When A is a substituted pyridine, several additional synthetic transformations are possible and some are shown here. The substituted pyridine (XLIX) is for example oxidized to yield an N-oxide (L) as the product. Additionally, when the pyridine ring contains one or more halogens such as chlorine in an activated position (ortho or para to the pyridine nitrogen), the halogen in (LI) may be displaced by a suitable nucleophile to yield the product (LII). Such nucleophiles are represented by mercaptans or nucleophilic heterocycles such as pyrazole or imidazole. Other substitution patterns within the pyridine may also be modified according to known general procedures for the modification of functional groups attached to heteroaryl or aryl rings. This is exemplified in the described hydrolysis of the nitrile (LIII) whereby treatment of compounds of this general structure with aqueous base provided access to the amides of general structure (LIV).

Scheme 15

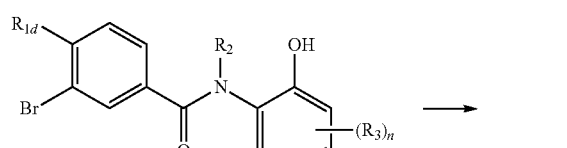

VI

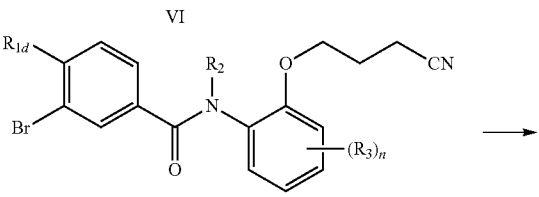

LV

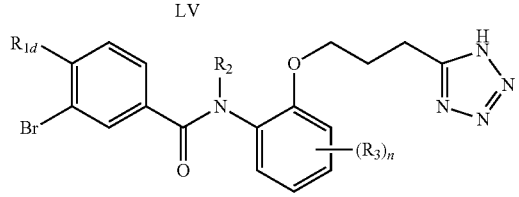

LVI

-continued

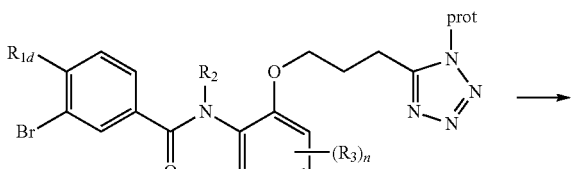

LVII

LVIII

LIX

LX

Intermediate phenol (VI) is alkylated under basic conditions to generate the alkyl nitrile (LV). This intermediate is coupled with an activated azide to allow for the synthesis of the tetrazole (LVI). At this stage the terazole moiety is protected by reaction with a suitable substituted alkyl halide (such as trimethylsilylethoxy methyl chloride) possibly resulting in a mix of isomers. The resultant alkyl tetrazole (LVII) is then converted to the boron ester (LVIII) as described previously before reaction with a suitable aryl or heteroaryl halide yields the protected intermediate (LIX). Subsequent deprotection of this species afforded the tetrazole (LX).

Scheme 16

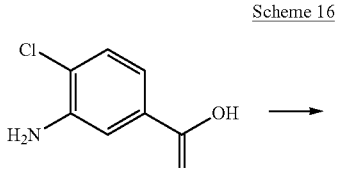

LXI

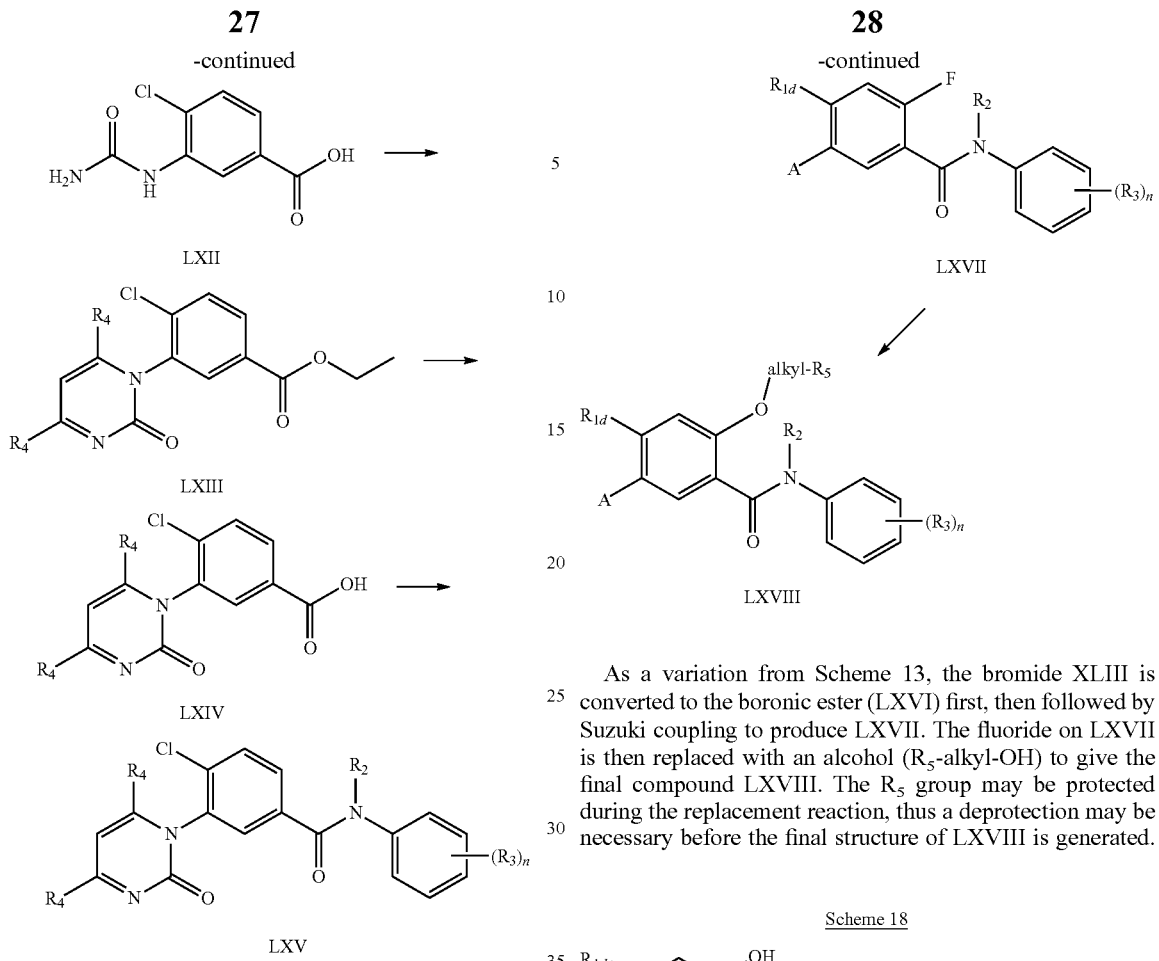

Aminobenzoic acid (LXI) is condensed with urea in acetic acid at high temperature. The resulting urea (LXII) is subjected to a second condensation with a suitably substituted 1,3-diketone in the presence of a strong acid to afford the aryl ester (LXIII). Removal of the ester function is accomplished through acidic hydrolysis to give the acid (LXIV) which was subsequently coupled to suitably substituted anilines (II) to yield the amides (LXV).

As a variation from Scheme 13, the bromide XLIII is converted to the boronic ester (LXVI) first, then followed by Suzuki coupling to produce LXVII. The fluoride on LXVII is then replaced with an alcohol ($R_5$-alkyl-OH) to give the final compound LXVIII. The $R_5$ group may be protected during the replacement reaction, thus a deprotection may be necessary before the final structure of LXVIII is generated.

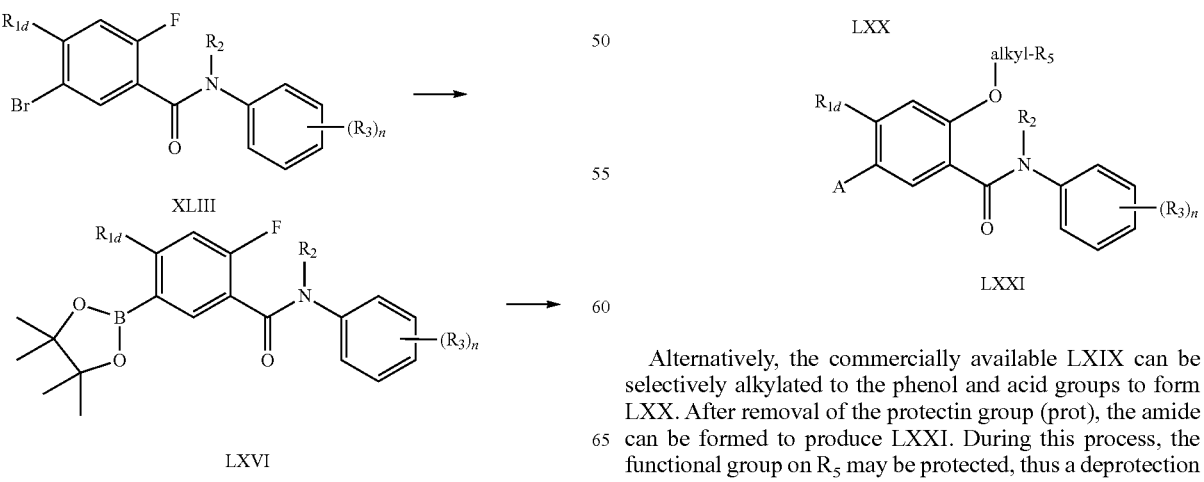

Alternatively, the commercially available LXIX can be selectively alkylated to the phenol and acid groups to form LXX. After removal of the protectin group (prot), the amide can be formed to produce LXXI. During this process, the functional group on $R_5$ may be protected, thus a deprotection may be necessary.

Scheme 19

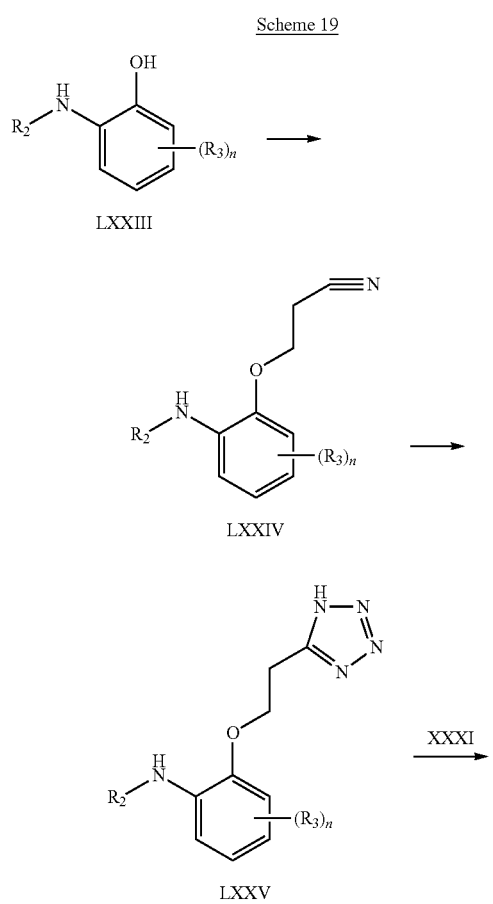

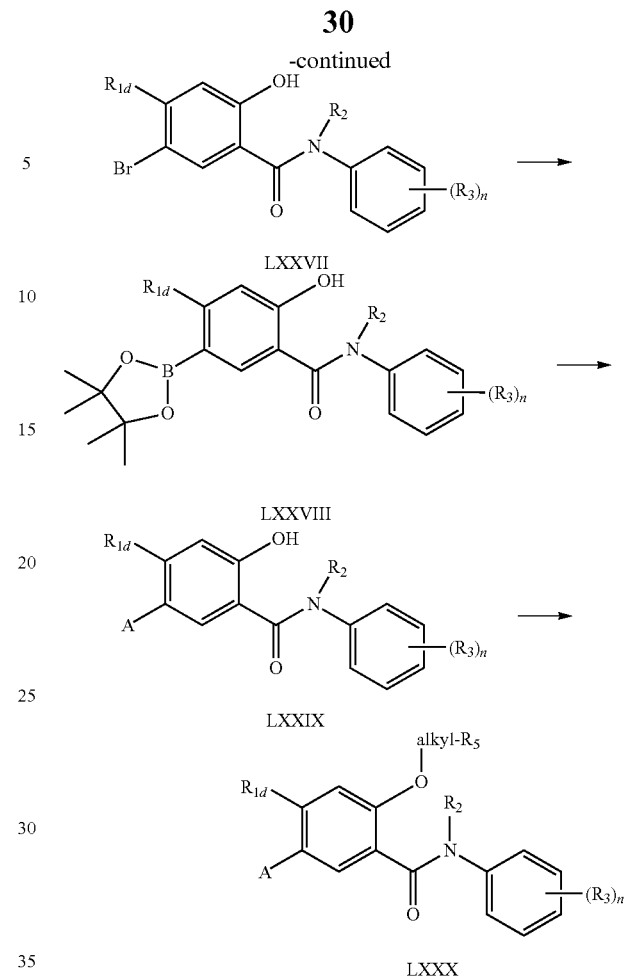

As a variation on Scheme 11, the aminophenol LXXIII reacts with acrylonitrile to form LXXIV which can be transformed into the tetrazole intermediate LXXV. Subsequently XXXI is activated by converting it into the corresponding acyl chloride which then reacts with LXXV in an aqueous solution to produce the desired product LXXVI.

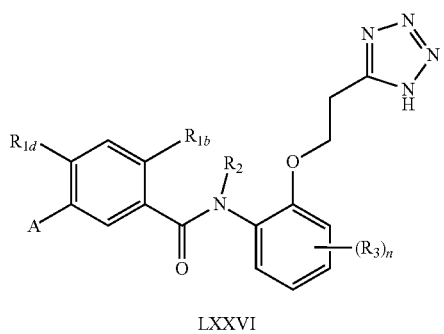

Scheme 20

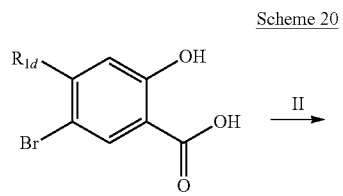

5-Bromo-4-$R_{1d}$-2-hydroxy-benzoic acid is coupled with a substituted aniline (II) to form the amide (LXXVII) in the presence of $P_2O_5$. Alternatively, (LXXVII) may be prepared by a coupling reaction with (II) in the presence of an activating reagent such as HBTU. Amide (LXXVII) may be used in a palladium (0) catalyzed reaction to give the boron ester (LXXVIII). Under Suzuki conditions this boronic ester could be reacted with a suitable aryl or heteroaryl halide to yield (LXXIX), which may be converted to the (LXXX) by alkylation with alkyl halides or mesylates or by a Mitsunobu reaction with alkyl alcohols.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids which form non-toxic salts. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or acid groups are bonded to any group that, when administered to a patient, cleaves to form the hydroxy, amine or acid groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures as well as individual enantiomers or diastereomers. All such isomeric forms are included within the present invention, including mixtures thereof.

The compounds of the present invention may exist in a continuum of solid states ranging from fully amorphous to fully crystalline. Furthermore, some of the crystalline forms of the compounds of structure (I) may exist as polymorphs, which are included in the present invention. In addition, some of the compounds of structure (I) may also form solvates with water or other organic solvents. The term solvate is used herein to describe a molecular complex comprising a compound of the present invention and one or more pharmaceutically acceptable solvent molecules. Such solvates are similarly included within the scope of this invention.

The present invention also includes all pharmaceutically acceptable isotopically labeled compounds of structure (I) where on or more atoms are replaced by atoms having the same atomic number but a different atomic mass. Examples include $^2H$ and $^3H$ for hydrogen, $^{11}C$, $^{13}C$ and $^{14}C$ for carbon, $^{36}Cl$ for chlorine, $^{18}F$ for fluorine, $^{123}I$ and $^{125}I$ for iodine, $^{13}N$ and $^{15}N$ for nitrogen, and $^{35}S$ for sulfur.

Compounds of the present invention include compounds of structure (I) as defined, including all polymorphs, prodrugs, isomers (including optical, geometric and tautomeric), salts, solvates and isotopes thereof.

The effectiveness of a compound as a GnRH receptor antagonist may be determined by various assay techniques. Assay techniques well known in the field include the use of cultured pituitary cells for measuring GnRH activity (Vale et al., *Endocrinology* 91:562-572, 1972) and the measurement of radioligand binding to rat pituitary membranes (Perrin et al., *Mol. Pharmacol.* 23:44-51, 1983) or to membranes from cells expressing cloned receptors as described below. Other assay techniques include (but are not limited to) measurement of the effects of GnRH receptor antagonists on the inhibition of GnRH-stimulated calcium flux, modulation of phosphoinositol hydrolysis, activation of ERK1/2, mast cell histamine release, and the circulating concentrations of gonadotropins in the castrate animal. Descriptions of these techniques, the synthesis of radiolabeled ligand, the employment of radiolabeled ligand in radioimmunoassay, and the measurement of the effectiveness of a compound as a GnRH receptor antagonist follow.

Cloning and Expression of GnRH Receptors cDNA's of human, rhesus macaque, rabbit, dog and rat GnRH receptors are cloned into pcDNA3.1 (+) (Invitrogen). Full length sequences of all receptors are confirmed by DNA sequencing. HEK 293, CHO, COS-7, or rat basophilic leukemia (RBL) cells are stably transfected with human, rat, or macaque GnRH receptors and high expressing single cell clones ($B_{max} \geq 0.4$ pMol/mg membrane protein) are isolated and maintained in Dulbecco's Modified Eagles Medium (DMEM) with following supplements: 10 mM HEPES; 2 mM L-glutamine; 1 mM Sodium Pyruvate; 50 U/mL penicillin, 50 µg/mL streptomycin; 10% Heat-inactivated Fetal Bovine Serum and 200 µg/mL Geneticin (G-4,8-Sulfate). Non-essential amino acids (0.1 mM) (Irvine Scientific; Santa Ana, Calif.) are included in the RBL cell media.

In general, initial peptide radioligand binding assays are carried out using membranes from stably transfected RBL cells. RBL stable clones are found to more consistently express high levels of GnRH receptor and are therefore used for subsequent binding studies as well as $Ca^{++}$ flux and inositol phosphate accumulation assays. Transiently transfected COS-7 cells are used for preparation of membranes containing GnRH receptors from multiple species (as well as those of mutant receptors for other studies) because of the convenience for rapidly analyzing multiple receptors. Stably transfected CHO cells are used for ERK1/2 stimulation assays because of superior signal/noise characteristics in this assay.

Membrane Preparation

HEK293 cells stably transfected with the human GnRH receptor are grown for two days after achieving confluence then are harvested by striking tissue culture flasks against a firm surface. Cells are collected by centrifugation at 1000 g for 5 minutes. Cell pellets are resuspended in 5% sucrose and homogenized using a polytron homogenizer for two 15 second homogenization steps. Cell homogenates are then centrifuged for 5 minutes at 3000 g to remove nuclei and the supernatant subsequently centrifuged for 30 minutes at 44,000 g to collect the membrane fraction. The membrane pellet is resuspended in GnRH binding buffer (10 mM HEPES, pH 7.5, 150 mM NaCl and 0.1% BSA) and aliquots immediately snap-frozen in liquid nitrogen and stored at –80° C. Protein content of the membrane suspension is determined using the Bio-Rad protein assay kit (Bio-Rad).

RBL cells stably transfected with the human GnRH receptor are grown to 80% confluency prior to harvesting. The cells are incubated at 37° C. for 10 min in 0.5 mM EDTA/PBS ($Ca^{++}$, $Mg^{++}$ free), and are dislodged from the plate by gentle rapping of the flasks. Cells are collected and pelleted by centrifugation at 1000 g for 5 minutes. Cell pellets are resuspended in buffer (DPBS supplemented with 10 mM $MgCl_2$, 2 mM EGTA, pH=7.4), and cell lysis is performed using a pressure cell and applying $N_2$ at a pressure of 900 psi for 30 min at 4° C. Unbroken cells and larger debris were removed by centrifugation at 1200 g for 10 min at 4° C. The cell membrane supernatant is then centrifuged at 45,000 g and the resulting membrane pellet is resuspended in assay buffer and homogenized on ice using a tissue homogenizer. Protein concentrations are determined using the Coomassie Plus Protein Reagent kit. Membranes are aliquoted and stored at –80° C. until ready for use.

COS-7 cells transiently transfected with GnRH receptors from different species (human, macaque, dog, rabbit, rat) or mutant GnRH receptors are prepared by bulk electroporation. COS-7 cells are obtained from American Type Cell Culture (Manassas, Va.) and are maintained in Dulbeccos's modified Eagle's medium (DMEM) (MediaTech Inc., Herndon, Va.) containing 10% fetal bovine serum, 10 mM HEPES, 2 mM L-glutamine, 1 mM sodium pyruvate, 50 U/mL penicillin, 50 μg/mL streptomycin. COS-7 cells are seeded in 500 cm² tissue culture plates and grown to confluency prior to cell transfection. $5 \times 10^7$ cells are transfected with 50 μg of the appropriate GnRH receptor DNA construct by electroporation in a BTX ElectroCell Manipulator ECM 600 (Fisher Scientific, Pittsburgh, Pa.) using the following settings: 1000 μF capacitance, 48Ω resistance, and 300 V/cm charging voltage. Transfected cells are cultured for 36-48 h prior to membrane preparation. Transiently transfected COS-7 cells are harvested, washed, and resuspended in membrane buffer (20 mM HEPES pH 7.2, 6 mM $MgCl_2$, 1 mM EDTA). Cells are centrifuged and the cell pellets are resuspended in a small volume of membrane buffer. Cells are lysed by release of pressure following incubation at 900 psi for 30 minutes at 4° C. in a nitrogen chamber. The homogenate is centrifuged at 1000 g for 10 minutes at 4° C. to remove nuclei and cellular debris. Membranes are collected from the supernatant by centrifugation at 44,000 g for 45 minutes at 4° C. Membranes are resuspended in membrane buffer at a concentration of 1 mg/mL, quick-frozen in liquid nitrogen, and stored at −80° C. until used.

Radioligand Binding Assays

Radioligand binding displacement assays using the peptide radioligands are performed in buffer containing 10 mM HEPES, 150 mM NaCl and 0.1% BSA, pH=7.5. Radioligand binding assays employing the use of [³H]-1-(2,6-difluorobenzyl)-3-[(2R)-amino-2-phenethyl]-5-(2-fluoro-3-methoxyphenyl)-6-methyluracil (here the 3-methoxy group is tritiated) are run in buffer containing 50 mM Tris, 150 mM NaCl, 5 mM $MgCl_2$, 0.01% saponin and 0.5 mM EDTA, pH=7.5. Radioligand displacement assays are performed by incubating radioligand ([$^{125}$I-Tyr⁵, DLeu⁶, NMeLeu⁷, Pro⁹-NEt]GnRH (0.1 nM), [His⁵, $^{125}$I-DTyr⁶]GnRH (0.2 nM) (31) or [³H]-1-(2,6-difluorobenzyl)-3-[(2R)-amino-2-phenethyl]-5-(2-fluoro-3-methoxyphenyl)-6-methyluracil (1 nM)), unlabeled competitors at concentrations ranging from 0.3 pM to 10 μM, and membranes for 2 hrs at rt. 10 to 20 μg protein/well is used from membrane preparations for human, monkey and rabbit GnRH receptor. 5 μg/well and 60 μg/well of membranes are used for rat and dog GnRH receptors, respectively. Binding assays are performed in either Millipore 96-well GF/C filtration plates (for ([$^{125}$I-Tyr⁵, DLeu⁶, NMeLeu⁷, Pro⁹-NEt]GnRH assays), or in 96 well low binding plates, which are subsequently filtered onto GF/C Unifilters. Filters are pretreated with 0.5% PEI for 30 min prior to use. Reactions are terminated by rapid vacuum filtration, and the filters are washed twice with 250 μL ice cold PBS pH=7.4 (0.01% Tween-20 is included in wash media for [His⁵, $^{125}$I-DTyr⁶]GnRH and [³H]-1-(2,6-difluorobenzyl)-3-[(2R)-amino-2-phenethyl]-5-(2-fluoro-3-methoxyphenyl)-6-methyluracil radioligands). The filters are dried, and the Millipore filters are monitored for radioactivity using a Cobra II gamma counter (Perkin Elmer Life Sciences). For assays filtered onto the GF/C Unifilter plates, 50 μL scintillation fluid is added to each filter, and radioactivity is monitored using a TopCount NXT. For iodinated radioligands, total radioligand is monitored on a gamma counter, and for the tritiated radioligand, total radioligand is monitored using a Perkin Elmer 1600TR liquid scintillation counter. Total radioligand bound does not exceed 10% of the total radioligand added, a level of depletion which does not appreciably affect the measurement of $K_i$. Nonspecific binding does not exceed 2% of the total radioligand added in any of the displacement assays. Inhibition of radioligand binding is fit to one-site and two-site competition binding equations and the best fit determined using an F-test. For all displacement binding experiments a single site binding model fit best (p<0.05). The $K_i$ values are calculated from the $IC_{50}$ values using the method of Cheng and Prusoff (*Biochem. Pharmacol.* 22:3099, 1973) and may be converted to a $pK_i$ value (negative log of the $K_i$ value).

$$K_i = \frac{IC_{50}}{1 + L/K_D}$$

where L=radioligand and $K_D$=affinity of radioligand for receptor. GnRH receptor antagonists of this invention have a $K_i$ of 10 μM or less. In other embodiments of this invention, the GnRH receptor antagonists have a $K_i$ of less than 1 μM, and in many instances have a $K_i$ of less than 0.1 μM (i.e., 100 nM).

Compounds of the present invention as shown in Examples 2 to 52 below (not including chemical intermediates) which were tested in one or more of the peptide competition human receptor binding assays shown have $K_i$ values of 1 μM or less. Additionally, the following compounds of the present invention as shown in Examples 2 to 52 below (not including chemical intermediates) which were tested in one or more of the peptide competition human receptor binding assays shown have Ki values of 100 nM or less, while the underlined compounds have Ki values of 10 nM or less:

<u>2-1</u>, 2-2, <u>2-3</u>, 2-6, 2-8, 2-9, <u>2-10</u>, 2-11, <u>2-12</u>, <u>2-13</u>, <u>2-14</u>, 2-15, 2-16, <u>2-18</u>, 2-19, 2-21, 2-22, 2-24, 2-25, 2-26, <u>2-27</u>, <u>2-29</u>, <u>2-31</u>, <u>2-33</u>, <u>2-34</u>, <u>2-35</u>, 2-36, 2-37, <u>2-39</u>, 2-42, 2-45, 2-46, 2-48, <u>2-49</u>, 2-50, <u>2-53</u>, 2-54, <u>2-55</u>, <u>2-57</u>, 2-58, 2-59, 2-60, 2-61, 2-62, <u>2-63</u>, 2-64, <u>2-65</u>, 2-66, 2-67, 2-68, <u>2-69</u>, 2-70, 2-71, 2-72, 2-75, 2-76, 2-77, 2-79, 2-80, 2-81, 3-1, 3-2, 3-3, 3-4, 3-5, 3-8, 3-9, 3-10, <u>3-11</u>, 3-12, 3-18, 3-19, 3-22, 4-1, <u>4-2</u>, <u>4-3</u>, 4-4, <u>4-5</u>, <u>4-6</u>, 4-7, <u>4-8</u>, 4-9, <u>4-10</u>, <u>4-11</u>, <u>4-12</u>, <u>5-1</u>, <u>5-2</u>, <u>5-3</u>, <u>5-4</u>, <u>5-5</u>, <u>5-6</u>, <u>6-1</u>, 7-1, <u>8-7</u>, <u>9-5</u>, <u>10-1</u>, <u>10-2</u>, <u>11-1</u>, <u>11-2</u>, <u>11-3</u>, <u>11-4</u>, <u>11-5</u>, <u>11-6</u>, <u>11-7</u>, <u>11-8</u>, 13-3, 14-1, 14-2, 14-3, <u>14-4</u>, 15-1, 16-1, 16-2, 17-2, 18-1, 19-1, <u>19-2</u>, 19-3, 19-5, 19-6, <u>19-7</u>, <u>19-8</u>, 19-9, <u>19-10</u>, <u>20-1</u>, <u>20-2</u>, <u>20-3</u>, <u>21-1</u>, <u>21-2</u>, <u>21-3</u>, <u>21-4</u>, 21-5, <u>21-6</u>, <u>21-7</u>, <u>21-8</u>, <u>22-1</u>, <u>22-2</u>, <u>22-3</u>, <u>22-4</u>, <u>22-6</u>, <u>22-7</u>, 22-8, <u>22-9</u>, <u>22-10</u>, <u>23-1</u>, 24-2, 26-1, <u>27-1</u>, <u>28-1</u>, 30-2, 30-5, 30-7, <u>30-8</u>, 30-9, 30-10, 30-11, <u>30-12</u>, <u>30-13</u>, 30-14, 30-15, 30-16, 30-17, <u>31-1</u>, <u>33-1</u>, <u>33-2</u>, 33-3, <u>34-1</u>, <u>34-2</u>, <u>34-3</u>, <u>34-4</u>, <u>34-5</u>, <u>34-6</u>, <u>34-7</u>, <u>34-8</u>, 34-9, <u>34-10</u>, <u>34-11</u>, <u>34-12</u>, 34-13, 34-15, 34-16, 34-17, <u>34-18</u>, 34-19, 34-20, <u>34-23</u>, 34-24, 34-25, <u>34-26</u>, <u>35-1</u>, 36-1, <u>36-2</u>, 37-1, 37-2, 37-3, 37-4, <u>38-1</u>, <u>39-1</u>, <u>39-2</u>, <u>39-3</u>, <u>39-4</u>, <u>39-5</u>, <u>39-6</u>, <u>39-7</u>, 39-8, 39-9, <u>39-10</u>, <u>39-11</u>, <u>39-12</u>, <u>39-13</u>, <u>39-14</u>, 39-15, <u>39-16</u>, <u>39-17</u>, <u>39-18</u>, <u>39-20</u>, <u>39-21</u>, <u>39-23</u>, <u>40-1</u>, <u>41-1</u>, <u>42-1</u>, <u>42-2</u>, <u>42-3</u>, <u>42-4</u>, <u>42-5</u>, <u>42-6</u>, <u>42-7</u>, <u>42-8</u>, <u>42-9</u>, <u>42-10</u>, <u>42-11</u>, <u>42-12</u>, <u>42-13</u>, <u>42-14</u>, <u>42-15</u>, <u>42-16</u>, <u>42-17</u>, <u>42-18</u>, <u>43-1</u>, <u>44-1</u>, <u>45-1</u>, <u>46-1</u>, 46-2, <u>46-3</u>, <u>46-4</u>, <u>47-1</u>, <u>47-2</u>, <u>47-3</u>, <u>47-4</u>, <u>47-5</u>, <u>48-1</u>, <u>48-2</u>, 49-1, <u>49-2</u>, <u>49-3</u>, 49-4, 50-1, 50-2, 50-3, <u>51-1</u>, <u>52-1</u>, 53-1, 53-2.

Wheat-germ agglutinin (WGA)-coupled polystyrene (PS) imaging beads (Amersham Biosciences, Piscataway, N.J.) are used in our scintillation proximity assay, permitting whole-plate light imaging with a CCD imaging system, as used by Viewlux (PerkinElmer Life Sciences, Boston, Mass.). Integrity of the receptor and radiolabel is monitored by saturation analysis measured at each time point to ensure a consistent $K_d$. Generally, the GnRH SPA assay produced reliable binding data up to 16 h of incubation. The optimal membrane/SPA bead ratio is determined for each membrane preparation and is typically 40 μg membrane/0.5 mg bead per well. Typically, the instrument is set to measure luminescence for 300 sec using a 613-nm filter to capture the red-shifted emission of the imaging beads and programmed to record at 60-min intervals for 11 h.

Reactions typically consist of 50 μL unlabeled compound various concentrations; 50 μL radiolabeled [$^{125}$I]-His$^5$, D-Tyr$^6$ GnRH ligand (~300 pM, 2200 Ci/mmol; PerkinElmer Life Sciences); and 100 μL membrane/SPA bead added sequentially in assay buffer (10 mM HEPES, 150 mM NaCl, 0.1% bovine serum albumin [BSA; Fraction V], pH 7.5) to low binding 96-well plates (Corning, Palo Alto, Calif.). Cell membrane fractions were prepared as previously described and resuspended in assay buffer.

SPA beads and membrane (rat basophilic leukemia [RBL] cells stably expressing human GnRH-R) are pre-incubated for 2 h prior to compound and radiolabel addition. The complete reaction is briefly shaken and allowed to settle at room temperature in the Viewlux instrument. The amount of bound radioligand is determined at the indicated time intervals.

A single-site binding model is applied for all displacement binding experiments, as determined by a partial F test (p>0.05). Dose-response curves for both time points of all compounds tested are normalized to zero and 100% specific binding, and $K_i$ values are calculated using the Cheng-Prusoff equation with a sigmoidal dose-response fit using Prism 4.0 software (GraphPad Software, San Diego, Calif.) using Kd values of 0.2 nM for [$^{125}$I]-His$^5$, D-Tyr$^6$ GnRH, as determined from saturation binding experiments. Hill slopes for all curves routinely range from −0.8 to −1.1.

Radioligand association experiments to estimate the affinity of compounds of the present invention may be initiated by the addition of cell membranes to wells containing an appropriate amount of a radiolabeled tracer, in the absence and presence of a range of concentrations of compound (Sullivan et al., *Biochemical Pharmacology*, 72, 2006, 838-849). All buffers are pre-heated to 37° C. prior to initiation of experiment, and assay plates are maintained at this temperature throughout the experiment. The assay mixture (total volume of 200 μL) is incubated at 37° C. for 1 min to 3 hr (15 time points), and the assay is terminated by rapid vacuum filtration through a cell harvester (UniFilter-96 Filtermate; Packard, PerkinElmer Life Sciences) onto Unifilter GF/B filter plate pretreated with 0.5% polyethylenimine in distilled water for 30 min. After filtration, membranes are washed two times with 400 μL wash buffer (Dulbecco's Phosphate-Buffered Saline, 0.01% Tween-20, pH 7.5). Filter plates are dried, 50 μL scintillation fluid is added (Microscint 20; PerkinElmer Life Sciences), and the plate is monitored for radioactivity using a TopCount NXT at 30% efficiency (PerkinElmer Life Sciences). The total amount of radioligand added to the assay is measured using a 1600TR liquid scintillation counter (PerkinElmer Life Sciences) at 47% efficiency. Analyses are performed using Prism 4.1 Software (GraphPad Software, San Diego, Calif.).

Ca$^{++}$ Flux Measurement

To determine the inhibition of GnRH-stimulated calcium flux in cells expressing the human GnRH receptor, a 96-well plate is seeded with RBL cells stably transfected with the human GnRH receptor at a density of 50,000 cells/well and allowed to attach overnight. Cells were loaded for 1 hour at 37° C. in the following medium: DMEM with 20 mM HEPES, 10% FBS, 2 μM Fluo-4, 0.02% pluronic acid and 2.5 mM probenecid. Cells are washed 4 times with wash buffer (Hanks balanced salt, 20 mM HEPES, 2.5 mM probenecid) after loading, leaving 150 μL in the well after the last wash. GnRH is diluted in 0.1% BSA containing FLIPR buffer (Hanks balanced salt, 20 mM HEPES) to a concentration of 20 nM and dispensed into a low protein binding 96-well plate. Various concentrations of antagonists are prepared in 0.1% BSA/FLIPR buffer in a third 96-well plate. Cell, agonist, and antagonist containing plates are loaded into a fluorometric imaging plate reader (FLIPR) (Molecular Devices, FLIPR384 system, Sunnyvale, Calif.) for liquid handling and fluorescence measurements according to manufacturer's instructions. The instrument is programmed such that antagonist (50 μL at varying concentrations) is added to cell plates and preincubated for 1 minute prior to addition of agonist (50 μL, or 4 nM final concentration of GnRH).

Measurement of [$^3$H]IP Production

The procedure is modified from published protocols (Zhou et al., *J. Biol. Chem.* 270:18853-57 (1995)). Briefly, RBL cells stably transfected with human GnRH receptors are seeded in 24 well plates at a density of 200,000 cell/well for 24 hours. Cells are washed once with inositol-free medium containing 10% dialyzed FBS and then labeled with 1 μCi/mL of [myo-$^3$H]inositol. After 20-24 hours, cells are washed with buffer (140 mM NaCl, 4 mM KCl, 20 mM Hepes, 8.3 mM glucose, 1 mM MgCl$_2$, 1 mM CaCl$_2$ and 0.1% BSA) and treated with native GnRH peptide in the same buffer with or without various concentrations of antagonist and 10 mM LiCl for 1 hour at 37° C. Cells are extracted with 10 mM formic acid at 4° C. for 30 min and loaded to the Dowex AG1-X8 column, washed and eluted with 1 M ammonium formate and 0.1 M formic acid. The eluate is counted in a scintillation counter. Data from PI hydrolysis assay are plotted using non-linear least square regression by Prism program (GraphPad Software, San Diego, Calif.), from which dose ratio is also calculated. The Schild linear plot is generated from the dose-ratios obtained in four independent experiments by linear regression, the X-intercept is used to determine the affinity of the antagonist.

Activation of ERK1/2

CHO cells stably expressing GnRH receptor are serum-starved for 1 hour, incubated for 5 min with various doses of antagonist, and stimulated with 1 nM GnRH for 5 min at 37° C. Cells are washed once with PBS and harvested directly into 2×SDS sample buffer. Cell extracts are sonicated, heated at 55° C. for 5 min, and subjected to SDS-PAGE. Resolved proteins are transferred onto nitrocellulose membranes. The activated phosphorylated form of ERK1/2 is detected using an anti-phosphoMAPK p42/44 antibody (Cell Signaling Technology, Danvers, Mass.) diluted at 1:3000 in 1% nonfat dried milk in TBST (20 mM Tris-HCl, pH 7.4, 137 mM NaCl, 0.1% Tween20). Total ERK1/2 is detected with the anti-ERK2 antibody (K23, Santa Cruz Biotechnology, Santa Cruz, Calif.). Chemiluminescent detection is performed with SuperSignal West Pico reagent (Pierce, Rockford, Ill.) and quantified on the VersaDoc3000 (Bio-Rad) imaging system. Dose-response data are plotted and analyzed with GraphPad Prism software.

Histamine Release

Rat peritoneal mast cells are obtained in accordance with the current NIH guidelines for the humane and ethical use of laboratory animals and animal welfare, and under an IACUC approved protocol. This method has been previously described for the evaluation of mast cell histamine release by peptide GnRH antagonists (Sundarem et al., *Agents Actions* 25:307-13 (1988)). Briefly, six male Sprague Dawley rats 240-300 g are sacrificed by CO$_2$ asphyxiation and 40 mL of cold PIPES buffer (25 mM PIPES, 110 mM NaCl, 5 mM KCl, 1 mg/mL glucose, 1 mg/mL BSA and 20 U/mL heparin, pH7.4) is injected into the peritoneal cavity and the abdomen massaged gently. Peritoneal wash is recovered and stored on ice. Cells from the peritoneal wash are washed 3 times with 5 mL PIPES buffer, pooled and purified on a Percoll gradient (Wells and Mann, *Biochem. Pharmacol.* 32:837-42 (1983)). For stimulation assays, approximately $2 \times 10^5$ cells in 300 µL PIPES buffer are placed into a 1.5 mL eppendorf tube and test compound (100 µL) is added to the cell suspension. The tubes are incubated at 37° C. for 15 min and the reaction is stopped with 600 µl of ice-cold PIPES buffer. After centrifugation at 4° C., the histamine level in the supernatant is determined by histamine EIA kit from SPI-BIO (Cayman Chemical, Ann Arbor, Mich.) following manufacturer's instructions.

LH Suppression in Castrated Macaques

This study in macaques is conducted in accordance with the current NIH guidelines for the humane and ethical use of laboratory animals and animal welfare, and under an IACUC approved protocol. A complete orchiectomy (both testes) is performed approximately 4 weeks prior to the first dose on male cynomolgus monkeys approximately 3.7 to 6.5 years of age (3.7 to 4.8 kg). Sexual maturity is verified by testicular volume and testosterone levels prior to surgery. Blood samples are collected weekly during the 4-week post-surgery recovery period for measurement of testosterone, FSH and LH to verify the rise in gonadotropins. Antagonist is administered to the stomach by nasogastric gavage or by i.v. infusion (over ~15 minutes). Blood samples are collected prior to and after each dose for analysis of serum LH and plasma antagonist concentrations. For the intravenous infusion dose, samples are collected at 0.25, 0.33, 0.5, 1, 1.5, 4, 8, and 24 hours after the initiation of the infusion. Samples are collected at 0.25, 0.5, 1, 1.5, 2, 4, 8, and 24 hours postdose for the oral doses. Bioactive LH concentrations in serum samples are measured at the Oregon Regional Primate Center (Beaverton, Oreg.) or the Yerkes Primate Research Center at Emory University using a previously reported mouse Leydig cell bioassay, which detects as little as 3 ng LH/mL using cynomolgus LH RP-1 as the reference preparation (Ellenwood and Resko, *Endocrinology* 107:902-907 (1980)).

As mentioned above, the GnRH receptor antagonists of this invention may have utility over a wide range of therapeutic applications, and may be used to treat a variety of sex-hormone related conditions in both men and women, as well as mammals in general. For example, such applications include endometriosis, uterine fibroids, polycystic ovarian disease, dysmenorrhea, dyspareunia, menorrhagia, nonmenstrual pelvic pain, pelvic tenderness, induration, general disorders of the menstrual cycle, premature ovarian failure due to chemotherapy or early menopause, hirsutism, precocious puberty, gonadal steroid-dependent neoplasia such as cancers of the prostate, breast and ovary, gonadotroph pituitary adenomas, adenomyosis sleep apnea, irritable bowel syndrome, premenstrual syndrome, benign prostatic hypertrophy, lower urinary tract symptoms (LUTS), contraception and infertility (e.g., assisted reproductive therapy such as in vitro fertilization). The compounds of this invention may also be useful as an adjunct to treatment of growth hormone deficiency and short stature, and for the treatment of systemic lupus erythematosis.

In addition, the compounds may be useful in combination with androgens, estrogens, progesterones, antiestrogens, antiprogestogens, angiotensin-converting enzyme inhibitors, angiotensin II-receptor antagonists, renin inhibitors, bisphosphonates and other agents for the treatment and/or prevention of disturbances of calcium, phosphate and bone metabolism, aromatase inhibitors, analgesics such as non-steroidal anti-inflamatory drugs (NSAIDS), other COX inhibitors, and anti-NGF agents.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount which is effective to treat a particular disorder—that is, in an amount sufficient to achieve GnRH receptor antagonist activity, and preferably with acceptable toxicity to the patient. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration.

For oral administration, suitable pharmaceutical compositions of GnRH receptor antagonists include powders, granules, pills, tablets, lozenges, chews, gels, and capsules as well as liquids, syrups, suspensions, elixirs, and emulsions. The compounds of the invention may also be used in fast dissolving, fast disintegrating dosage forms. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramusclar, subcutaneous or other injection or infusion. Parenteral formulations may be prepared in aqueous injection solutions which may contain, in addition to the GnRH receptor antagonist, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intanasal administration, such as with a dry powder, an aerosol spray or as drops. Additional routes of administration for compounds of the present invention include intravaginal and rectal (by means of a suppository, pessary or enema), and ocular and aural.

For administration to human patient (or subject), the total daily dose of the compounds of the present invention may be in the range of 1 to 500 mg, typically 5 to 300 mg, more typically 25 to 250 mg, depending, of course on a number of factors including age, sex, and weight of a subject and also on the mode of administration. The total daily dose may be administered singly or in divided doses.

The following examples are provided for purposes of illustration, not limitation. In summary, the GnRH receptor antagonists of this invention may be assayed by the general methods disclosed above, while the following Examples disclose the synthesis of representative compounds of this invention.

EXAMPLES

HPLC Methods for Analyzing the Samples

Retention time, $t_R$, in minutes
Method 1: Column: Synergi 4μ, Max-RP 80A, 50×2 mm;
Gradients: from 95% $H_2O$+0.025% TFA/MeCN to 95% MeCN+0.025% TFA/$H_2O$ over 13 min;
Flow rate: 1 mL/min; UV: 222 and 254 nM
Method 2: Column: Synergi 4μ, Max-RP 80A, 50×2 mm;
Gradients: from 95% $H_2O$+0.025% TFA/MeCN to 95% MeCN+0.025% TFA/$H_2O$ over 13 min;
Flow rate: 1 mL/min; UV: 222 and 254 nM
Method 3: Column: Phenomenex 5μ, Gemini C18 110A, 150×4.6 mm
Gradients: from 95% $H_2O$+0.04% $NH_4OH$ to 90% MeCN+0.04% $NH_4OH$ over 9.86 min.
Flow rate: 2.5 mL/min. UV: 222 and 254 nM
Method 4: Column: Phenomenex 4μ, RP 80A, 50×2 mm
Gradients: from 95% [$H_2O$+10 mM $NH_4CHO$]; 5% [25% MeCN in MeOH] to 5% [$H_2O$+10 mM $NH_4CHO$] over 6.43 min.
Flow rate: 1 mL/min. UV: 222 and 254 nM
Method 5: Column: Waters Xterra RP, 250×3 mm
Gradients: from 90% [$H_2O$+0.025% TFA] to 95% [MeCN+0.025% TFA] over 46 min.
Flow rate: 0.8 mL/min. UV: 222 and 254 nM Example 1

5-Bromo-2-trifluoromethyl-isonicotinonitrile

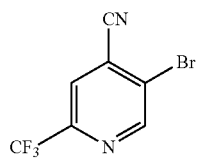

Step 1A: 5-Bromo-2-trifluoromethyl-isonicotinic acid

To a 100 mL round bottom flask equipped with a rubber septa and nitrogen inlet was charged 5 g (22.1 mmol) of 5-bromo-2-trifluoromethylpyridine. To the solid was charged 30 mL of anhydrous THF under a nitrogen atmosphere. After the solution became homogeneous, it was chilled with a −78° C. dry ice/acetone bath. To a separate 100 mL round bottom flask equipped with a rubber septa and nitrogen inlet was charged 3.4 mL (24.2 mL, 1.1 eq) of anhydrous diisopropyl amine. To the solution was charged 16.9 mL of anhydrous THF, placed under a nitrogen atmosphere and chilled with an ice bath. To the solution was carefully added 9.7 mL (24.3 mmol, 1.1 eq) of 2.5 M n-butyl lithium in hexanes. The light yellow LDA solution was chilled with a −78° C. dry ice/acetone bath. A 100 mL pear shaped flask equipped with a rubber septa, nitrogen inlet, stir bar, thermocouple and double headed cannula needle was placed under a nitrogen atmosphere and chilled with a −78° C. dry ice/acetone bath. To a 250 mL round bottom flask equipped with a rubber septa, $CO_2$ inlet, needle outlet and stir bar was charged 30 mL of anhydrous THF. The solution was chilled with a −78° C. dry ice/acetone bath and anhydrous $CO_2$ bubbled through the solution for 10 minutes.

To the empty 100 mL flask was charged 5 mL of the LDA solution. To this was charged 5 mL of the 5-bromo-2-trifluoromethylpyridine solution at such a rate to keep the solution temperature <−60° C. Upon addition, the mixture was stirred for 1 minute then transferred via cannula under positive nitrogen pressure to the $CO_2$ saturated solution. This afforded a light maroon solution. The process was repeated until all starting materials were transferred to the $CO_2$ solution. The $CO_2$ solution was allowed to stir with a −78° C. dry ice/acetone bath for 1 hour. The cooling bath was removed and the solution allowed to warm to ambient temperature.

To the reaction mixture was carefully added 150 mL of saturated ammonium chloride solution. The mixture was transferred to a 500 mL separatory funnel. The lower aqueous phase was separated and the organic phase extracted with 100 mL of 1N sodium hydroxide solution. The combined aqueous phases were extracted with 100 mL of MTBE. The aqueous phase was acidified to pH 1 with concentrated hydrochloric acid. The cloudy aqueous mixture was extracted twice with 200 mL of MTBE. The combined organic phases were washed once with 100 mL of brine, dried over magnesium sulfate, filtered and concentrated in vacuo to afford 5-bromo-2-trifluoromethyl-isonicotinic acid (4.7 g) as an off-white solid in a 78% yield.

Step 1B:
5-Bromo-2-trifluoromethyl-isonicotinamide

To a 500 mL round bottom flask equipped with a stir bar, condenser and nitrogen inlet was charged 38.9 g (144 mmol) of 5-bromo-2-trifluoromethyl-isonicotinic acid. To the solid was charged 250 mL of anhydrous dichloromethane followed by 13.2 mL (151 mmol, 1.05 eq) oxalyl chloride. To the mixture was added 0.5 mL of anhydrous dimethylformamide and the mixture was stirred at ambient temperature for 2 h. The reaction was complete as evidenced by HPLC (methanol quench of aliquot). The solvent was removed in vacuo affording an amber oil.

To a 1 L Erlenmeyer flask equipped with a stir bar in an ice-bath was charged 500 mL of aqueous ammonium hydroxide. To the chilled solution was added dropwise the crude acid chloride. The residue was transferred with a small amount of acetonitrile. The mixture was stirred for 20 minutes following addition. The resulting precipitate was collected by filtration and washed with water. The filter cake was dried in vacuo at 45° C. affording 31.8 g of 5-bromo-2-trifluoromethyl-isonicotinamide as an off-white solid in a 82% yield. The compound may also be purified using an ether slurry and collecting the solid.

Step 1C:
5-Bromo-2-trifluoromethyl-isonicotinonitrile

To a 100 mL round bottom equipped with a stir bar, condenser and nitrogen inlet was charged 5.2 g (19.3 mmol) of 5-bromo-2-trifluoromethyl-isonicotinamide. The solid was diluted with 12 mL of phosphorus oxychloride. The mixture was heated at 70° C. for 3 hr. The mixture was cooled to ambient temperature and poured onto ice. The mixture was neutralized with the careful addition of 50% sodium hydroxide. The resulting off-white solid was collected by filtration, washed with water and dried in vacuo at 50° C. for 18 h. This afforded 4.5 g of 5-bromo-2-trifluoromethyl-isonicotinonitrile 1-1 as an off-white solid in a 94% yield. $^1$HNMR (CDCl$_3$), δ, 9.03 (s, 1H), 7.91 (s, 1H).

5-Bromo-4-methyl-2-(trifluoromethyl)pyridine

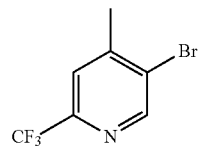

Step 1E:
5-Bromo-4-methyl-2-(trifluoromethyl)pyridine

In a dried 250 mL 3-neck round bottom flask fitted with a stirrer bar, thermometer, and flushed with nitrogen, was placed anhydrous THF (16 mL, Aldrich, inhibitor free) followed by N,N-diisopropylamine (0.895 g, 8.85 mmol, Aldrich, redistilled 99.95% pure). After cooling the stirred solution to −70° C., n-butyl lithium (3.54 mL of a 2.5M solution in hexanes, 8.85 mmol) was added dropwise, keeping the reaction temperature less than −60° C. The resulting solution was stirred at −70° C. for a further 10 min, then warmed to −20° C., before immediately cooling to −90° C. A solution of 5-bromo-2-(trifluoromethyl)pyridine (2 g, 8.85 mmol) in anhydrous THF (8 mL, Aldrich, inhibitor free) was added dropwise, keeping the reaction temperature less than −85° C. The resulting orange solution was stirred at −90° C. for 40 min.

In a separate dried 250 mL 3-neck round bottom flask fitted with a stirrer bar, thermometer, and flushed with nitrogen, was placed anhydrous THF (5 mL, Aldrich, inhibitor free) followed by methyl iodide (5 mL, 80 mmol). The solution was cooled to −90° C. To this was added (via cannula) the solution of the pre-formed lithiated pyridine, controlling the rate so as to keep the reaction temperature of the receiving flask less than −80° C. The resulting dark solution was stirred at −90° C. for a further 15 min (LCMS indicated reaction complete). The reaction was quenched with sat aq. NH$_4$Cl solution (50 mL), then allowed to slowly warm to room temperature. Organics were extracted with EtOAc (2×50 mL), then the combined organic layers washed with water (50 mL), then brine (50 mL), separated, dried over MgSO$_4$, and then filtered. Concentration in vacuo gave 1.68 g of a brown oil which was purified via short-path vacuum distillation (45-46° C., ca. 5 mmHg) to give 5-bromo-4-methyl-2-(trifluoromethyl)pyridine 1-2 (0.289 g, 14%) as a yellow oil (>97% pure). MS (M+H)$^+$: 241.8, $t_R$=2.458 min (method 1); $^1$H NMR (CDCl$_3$) δ 8.74 (1H, s), 7.56 (1H, s), 2.50 (3H, s).

5-Bromo-2-cyano-4-methylpyridine

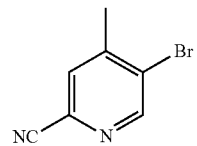

Step 1F: 2,5-Dibromo-4-methylpyridine

2-Amino-5-bromo-4-methylpyridine (2.0 g, 10.7 mmol) was dissolved in 48% aqueous HBr (14 mL, 123 mmol) and cooled to 2° C. in a salt/ice bath. Bromine (1.65 mL, 32.1 mmol) was added dropwise keeping the internal temperature below 2° C. A solution of sodium nitrite (3.69 g, 53.5 mmol) in water (5 mL) was added keeping the internal temperature below 5° C. and stirred for 1 h between 0° C. and 5° C. The pH was adjusted to ~13 by slow addition with cooling of 50% NaOH (aq). After warming to r.t. the reaction was extracted with ether, the organics were dried over MgSO$_4$ and concentrated to give a brown oil. Flash chromatography on silica gel eluting with 5% ether/hexane gave the product as a white solid (1.83 g, 7.29 mmol, 68%). MS [M+H]$^+$: 251.9; $t_R$=2.3 min. (method 1)

Step 1G: (5-Bromo-4-methylpyridin-2-yl)-N-t-butyl carboxylic amide 2,5-Dibromo-4-methylpyridine (1.83 g, 7.29 mmol) was dissolved in toluene (100 mL), cooled to −78° C. and a solution of nBuLi (4.4 mL, 8.8 mmol, 2.0 M in pentane) was added dropwise and stirred at −78° C. for 2 h. A solution of tBuNCO (1.1 mL, 9.5 mmol) in toluene (3 mL) was added dropwise and stirred for 1 h at −78° C. then warmed to −10° C. and quenched by addition of NH$_4$Cl (aq). After warming to r.t. the reaction was extracted with ether and the organics dried over Na$_2$SO$_4$ and concentrated. The product was used without further purification. MS [M+H]$^+$: 271.0; $t_R$=2.44 min. (method 1)

Step 1H: 5-Bromo-2-cyano-4-methylpyridine

This material was dissolved in toluene (10 mL). POCl$_3$ (10 mL) was added and the solution refluxed for 5 h. After cooling to room temperature the solvents were removed in vacuo, the reaction was basified by addition of 2 M NaOH (aq) and extracted with ether. The organic extract was washed with brine, dried over MgSO$_4$ and concentrated. Chromatography on silica gel eluting with 20% EtOAc/Hexane gave 5-bromo-2-cyano-4-methylpyridine 1-3 as an off-white crystalline solid (920 mg, 4.7 mmol, 64% over 2 steps). ¹H NMR (300 MHz, CDCl₃) 8.73 (1H, s), 7.56 (1H, s), 2.46 (3H, s). MS [M+H]⁺: 196.8.0; $t_R$=2.04 min. (method 1).

2-Bromo-3,5-dichloro-6-methylpyridine

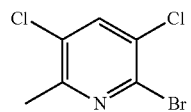

Step 1I: 2-Bromo-3,5-dichloro-6-methylpyridine

2-Amino-3,5-dichloro-6-methylpyridine (3.54 g, 20 mmol) was suspended in aqueous 48% HBr solution at room temperature and the mixture was cooled to −20° C. This suspension was maintained at −20° C. while bromine (2.87 mL, 56 mmol) was added dropwise. The resultant paste was stirred for 30 minutes at this temperature before the dropwise addition of a cooled solution of sodium nitrite (3.59 g, 52 mmol) in water (5 mL). At this point the reaction mixture was allowed to warm to room temperature. After stirring for a further 60 minutes, the mixture was again cooled to −20° C. and treated with a solution of sodium hydroxide (16 g, 0.4 mol) in water (20 mL). This mixture was extracted with ethyl acetate and the organic layer washed with water and then brine solution. The organic solution was dried over MgSO₄, filtered and the residue obtained from solvent evaporation was purified using silica gel chromatography [eluent: 10% ethyl acetate in hexane]. 2-Bromo-3,5-dichloro-6-methylpyridine 1-4 (2.14 g, 45%) was obtained as a solid.

5-Bromo-4-chloro-2-methyl-pyridine

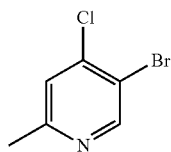

Step 1J: 5-Bromo-2-methyl-4-nitropyridine oxide

A mixture of 5-bromo-2-methyl-pyridine (10.0 g, 58.0 mmol), hydrogen peroxide (28 mL, 30% in water) in acetic acid (28 mL) was heated to 90° C. for 2 days, then additional hydrogen peroxide (14 mL) was added. The mixture was heated for another 1 day. Upon cooling to room temperature, it was extracted with CHCl₃ three times. The organic solution was then dried over MgSO₄, and concentrated to yield the crude pyridine oxide. MS: 187.7 (M+H)⁺; $t_R$=2.22 min. (method 1).

The above pyridine oxide was added into a mixture of HNO₃ (18 mL) and H₂SO₄ (16 ml) at 0° C. The mixture was then heated to 90° C. for 48 hrs, allowed to cool to room temperature and poured into iced water resulting in a precipitation. The solid was filtered and dried to afford 5-bromo-2-methyl-4-nitropyridine oxide (7.32 g). MS: 232.7 (M+H)⁺; $t_R$=1.94 min. (method 1).

Step 1K: 5-Bromo-4-chloro-2-methylpyridine

5-Bromo-2-methyl-4-nitropyridine oxide (7.0 g, 30 mmol) was refluxed in conc. HCl (80 mL) for 16 hrs. The mixture was allowed to cool to room temperature, partially concentrated and then neutralized by NaOH (10N) to pH 7. The crude was partitioned between CHCl₃ and water. The organic solution was separated, dried and concentrated to yield 5-bromo-4-chloro-2-methylpyridine oxide as a white solid (6.71 g). MS [M+H]⁺: 223.7; $t_R$=1.91 min. (method 1).

To the solid (6.71 g, 30 mmol) in CHCl₃ (60 mL) at 0° C., was added POCl₃ (7.85 mL, 90 mmol) slowly. The mixture was heated to reflux for 3 hrs and allowed to cool to room temperature. The product was extracted by CHCl₃. The extracted solution was washed with sat. NaHCO₃, water and dried over MgSO₄. The filtrate was then concentrated to yield 5-bromo-4-chloro-2-methylpyridine 1-5 as a yellow oil (5.9 g). MS [M+H−Cl]⁺: 171.9; $t_R$=2.13 min. (method 1)

Example 2

4-Chloro-3-(6-chloro-pyridin-3-yl)-N-(2-methoxyphenyl)-N-methyl-benzamide

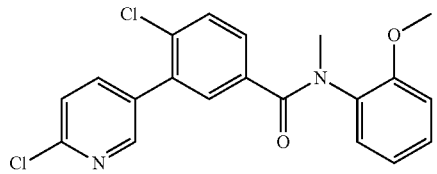 [SMILES: COc1ccccc1N(C)C(=O)c1ccc(Cl)c(-c2ccc(Cl)nc2)c1]

Step 2A: 3-Bromo-4-chloro-benzoyl chloride

To 3-bromo-4-chloro-benzoic acid (9.4 g, 40 mmol) in dry DCM (100 mL), was added DMF (0.5 mL) followed by addition of oxalyl chloride (22.5 mL, 55 mmol, 2M in DCM) slowly. The mixture was stirred for 1 hr, then concentrated to yield 3-bromo-4-chloro-benzoyl chloride as an off-white solid.

Step 2B: 3-Bromo-4-chloro-N-(2-methoxy-phenyl)-benzamide

3-Bromo-4-chloro-benzoyl chloride in DCM (200 mL) was cooled in an ice bath and triethylamine (11.1 mol, 80 mmol) was added slowly, followed by the drop-wise addition of o-anisidine (4.5 mL, 40 mmol) in DCM (50 mL). At this time the ice bath was removed and the mixture was stirred for 12 hrs, followed by partition between DCM and water. The organic layer was washed with 1 N HCl, saturated NaHCO₃, brine and dried over MgSO₄. Concentration of the filtrate yielded 3-bromo-4-chloro-N-(2-methoxy-phenyl)-benzamide as a pinkish solid (13.5 g).

Step 2C: 3-Bromo-4-chloro-N-(2-methoxy-phenyl)-N-methyl-benzamide

To 3-bromo-4-chloro-N-(2-methoxy-phenyl)-benzamide (13.5 g, 39 mmol) in DMF (100 mL) at 0-5° C., was added NaH (1.9 g, 46.8 mmol, 60% in mineral oil) in several portions, followed by addition of iodomethane (3.15 mL, 50.7 mmol). The mixture was stirred at room temperature for 4 hrs and was partitioned between ethyl acetate and water.

The organic layer was then washed with 1N HCl, saturated NaHCO₃, brine and dried over MgSO₄. Filtration over a silica gel pad followed by concentration and crystallization from ether/hexane yielded 3-bromo-4-chloro-N-(2-methoxy-phenyl)-N-methyl-benzamide (10.9 g) as a white solid. MS (M+H)⁺: 353.9, $t_R$=2.812 min (method 1); NMR (CDCl₃), δ, 7.62 (1H, d, J=1.5 Hz), 7.23-7.09 (3H, m), 7.06-7.00 (1H, m), 6.88-6.78 (2H, m), 3.75 (3H, s), 3.34 (3H, s)

Step 2C.1: 3-Bromo-4-chloro-N-(2-methoxy-phenyl)-N-methyl-benzamide (Alternate Synthesis)

To 3-bromo-4-chloro-benzoyl chloride (5.4 g, 21.4 mmol) in DCM (100 mL) cooled with an ice bath, was added methoxy-N-methylaniline (3.2 g, 23.4 mmol), followed by addition of triethylamine (5.9 mL, 42.5 mmol) slowly. Upon the completion of the addition, the ice bath was removed and the mixture was stirred at room temperature for 12 hrs, followed by partition between DCM and water. The organic layer was then washed with 1 N HCl, saturated NaHCO₃, brine and was dried over MgSO₄. Concentration and purification by silica gel column chromatography eluting with hexane/ethyl acetate (4/1) yielded 3-bromo-4-chloro-N-(2-methoxy-phenyl)-N-methyl-benzamide (5.1 g) as a solid.

Step 2D: 4-Chloro-N-(2-methoxy-phenyl)-N-methyl-3-(4,4,5,5-tetramethyl-[1,3,2]dioxaborolan-2-yl)-benzamide To 3-bromo-4-chloro-N-(2-methoxy-phenyl)-N-methyl-benzamide (9.7 g, 27.4 mmol) in dioxane (150 mL), were added bis(pinacolato)diboron (10.4 g, 41.1 mol), potassium acetate (8.05 g, 82.2 mmol) and Pd(dppf)₂Cl₂·CH₂Cl₂ (1.1 g, 1.35 mmol). The mixture was bubbled with N₂ for 10 min and then heated under N₂ at 80° C. for 24 hrs. The mixture was cooled to room temperature, filtered through a silica gel pad, then concentrated. The resulting oil was purified by silica gel column chromatography eluting with ethyl acetate in hexanes from 20% to 30% to yield 4-chloro-N-(2-methoxy-phenyl)-N-methyl-3-(4,4,5,5-tetramethyl-[1,3,2]dioxaborolan-2-yl)-benzamide (10.7 g). NMR (CDCl₃), δ, 7.66 (1H, d, J=2.4 Hz), 7.32-7.23 (1H, m), 7.17-7.07 (2H, m), 7.02-6.95 (1H, m), 6.82-6.74 (2H, m), 3.74 (3H, s), 3.33 (3H, s), 1.30 (12H, s).

Step 2E: 4-Chloro-3-(6-chloro-pyridin-3-yl)-N-(2-methoxy-phenyl)-N-methyl-benzamide 2-1

A mixture of toluene (1.5 mL) and water (0.5 mL) containing 4-chloro-N-(2-methoxy-phenyl)-N-methyl-3-(4,4,5,5-tetramethyl-[1,3,2]dioxaborolan-2-yl)-benzamide (60 mg, 0.15 mmol), 5-bromo-2-chloro-pyridine (29 mg, 0.15 mmol), Pd(PPh₃)₄ (12 mg, 0.01 mmol), Na₂CO₃ (2N, 0.15 mL, 0.3 mmol), was bubbled with N₂ for 5 min, then heated at 100° C. for 12 hrs. The mixture was filtered and purified by prep. LCMS to yield 4-chloro-3-(6-chloro-pyridin-3-yl)-N-(2-methoxy-phenyl)-N-methyl-benzamide 2-1 (22.6 mg). MS: 386.7 (M+H)⁺; $t_R$=7.77 min (method 2).

Step 2E.1: 4-Chloro-3-(6-chloro-pyridin-3-yl)-N-(2-methoxy-phenyl)-N-methyl-benzamide (Alternate Synthesis)

A mixture of 4-chloro-N-(2-methoxy-phenyl)-N-methyl-3-(4,4,5,5-tetramethyl-[1,3,2]dioxaborolan-2-yl)-benzamide (60 mg, 0.15 mmol), 5-bromo-2-chloro-pyridine (29 mg, 0.15 mmol), Pd(PPh₃)₄ (12 mg, 0.01 mmol), K₂CO₃ (41 mg, 0.3 mmol) in dioxane (1 mL), was heated at 100° C. for 12 hrs. The mixture was filtered and purified by prep. LCMS to yield 4-chloro-3-(6-chloro-pyridin-3-yl)-N-(2-methoxy-phenyl)-N-methyl-benzamide 2-1.

The following compounds were prepared according to the procedures described above.

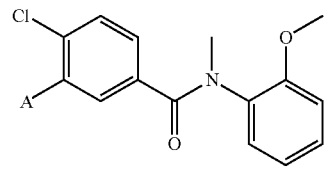

| Ex. | A | MS (M + H)⁺ | $t_R$ (min) | HPLC Method |
|---|---|---|---|---|
| 2-1 | 6-methyl-pyridin-3-yl | 366.8 | 4.45 | 2 |
| 2-2 | 6-cyano-pyridin-3-yl | 377.7 | 7.32 | 2 |
| 2-3 | 4,6-dichloro-pyridin-3-yl | 422.9 | 8.32 | 2 |
| 2-4 | 2-chloro-6-methyl-pyridin-3-yl | 400.7 | 7.47 | 2 |
| 2-5 | 2,6-dimethyl-pyridin-3-yl | 380.8 | 4.30 | 2 |
| 2-6 | 2,6-dichloro-pyridin-3-yl | 420.7 | 8.43 | 2 |
| 2-7 | 6-methoxy-4-methyl-pyridin-3-yl | 397.0 | 7.38 | 2 |
| 2-8 | 4-chloro-6-methyl-pyridin-3-yl | 401.0 | 6.31 | 2 |
| 2-9 | 4,6-dimethyl-pyridin-3-yl | 380.8 | 4.23 | 2 |
| 2-10 | 6-cyano-4-methyl-pyridin-3-yl | 392.0 | 7.38 | 2 |
| 2-11 | 6-trifluoromethyl-pyridin-3-yl | 420.7 | 9.63 | 3 |
| 2-12 | 4-methyl-6-trifluoromethyl-pyridin-3-yl | 434.9 | 9.81 | 3 |
| 2-13 | 6-chloro-4-methyl-pyridin-3-yl | 410.5 | 8.32 | 2 |
| 2-14 | 4-cyano-6-trifluoromethyl-pyridin-3-yl | 446.0 | 8.26 | 2 |

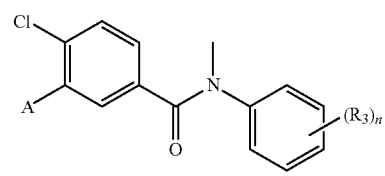

| Ex. | A | | MS (M + H)⁺ | $t_R$ (min) | HPLC Method |
|---|---|---|---|---|---|
| 2-15 | 6-chloro-pyridin-3-yl | 2-methyl-phenyl | 370.9 | 9.04 | 3 |
| 2-16 | 4-chloro-6-methyl-pyridin-3-yl | 2-methyl-phenyl | 384.8 | 6.57 | 2 |

-continued

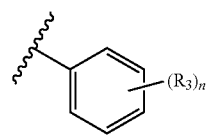

| Ex. | A | (R₃)ₙ phenyl | MS (M + H)⁺ | $t_R$ (min) | HPLC Method |
|---|---|---|---|---|---|
| 2-17 | 2-chloro-6-methyl-pyridin-3-yl | 2-methyl-phenyl | 386.7 | 7.77 | 2 |
| 2-18 | 6-chloro-4-methyl-pyridin-3-yl | 2-methyl-phenyl | 384.8 | 8.23 | 2 |
| 2-19 | 4-chloro-6-methyl-pyridin-3-yl | 2,6-dimethyl-phenyl | 398.7 | 6.91 | 2 |
| 2-20 | 2-chloro-6-methyl-pyridin-3-yl | 2,6-dimethyl-phenyl | 398.7 | 8.09 | 2 |
| 2-21 | 4-chloro-2,6-dimethyl-pyridin-3-yl | 2,3-dimethyl-phenyl | 413.0 | 5.87 | 2 |
| 2-22 | 4-chloro-6-methyl-pyridin-3-yl | 2,3-dimethyl-phenyl | 398.8 | 7.04 | 2 |
| 2-23 | 2-chloro-6-methyl-pyridin-3-yl | 2,3-dimethyl-phenyl | 398.8 | 8.12 | 2 |
| 2-24 | 4-chloro-6-methyl-pyridin-3-yl | 2-methyl-3-trifluoromethyl-phenyl | 452.7 | 7.61 | 2 |
| 2-25 | 4-chloro-2,6-dimethyl-pyridin-3-yl | 2-methyl-3-trifluoromethyl-phenyl | 466.7 | 6.56 | 2 |
| 2-26 | 6-methoxy-4-methyl-pyridin-3-yl | 2-methoxy-6-methyl-phenyl | 411.1 | 9.64 | 3 |
| 2-27 | 4-chloro-6-methyl-pyridin-3-yl | 2-methoxy-6-methyl-phenyl | 414.9 | 9.13 | 3 |
| 2-28 | 2,6-dimethyl-pyridin-3-yl | 2-methoxy-6-methyl-phenyl | 395.7 | 8.60 | 3 |
| 2-29 | 4,6-dichloro-pyridin-3-yl | 2-methoxy-6-methyl-phenyl | 437.1 | 10.21 | 3 |
| 2-30 | 2-chloro-4-methyl-pyridin-3-yl | 2-methoxy-6-methyl-phenyl | 416.7 | 7.66 | 2 |
| 2-31 | 6-chloro-4-methyl-pyridin-3-yl | 2-methoxy-6-methyl-phenyl | 414.8 | 8.32 | 2 |
| 2-32 | 6-trifluoromethyl-pyridin-3-yl | 2-methoxy-6-methyl-phenyl | 435.0 | 9.96 | 3 |
| 2-33 | 4-methyl-6-trifluoromethyl-pyridin-3-yl | 2-methoxy-6-methyl-phenyl | 449.4 | 10.11 | 3 |
| 2-34 | 6-cyano-4-methyl-pyridin-3-yl | 2-methoxy-6-methyl-phenyl | 406.0 | 7.73 | 2 |
| 2-35 | 4-cyano-6-trifluoromethyl-pyridin-3-yl | 2-methoxy-6-methyl-phenyl | 459.9 | 9.81 | 3 |
| 2-36 | 6-chloro-4-methyl-pyridin-3-yl | 2-fluoro-phenyl | 388.7 | 8.10 | 2 |
| 2-37 | 4-chloro-6-methyl-pyridin-3-yl | 2-fluoro-phenyl | 388.8 | 6.46 | 2 |
| 2-38 | 4-chloro-2,6-dimethyl-pyridin-3-yl | 2-fluoro-phenyl | 402.7 | 5.46 | 2 |
| 2-39 | 6-bromo-4-methyl-pyridin-3-yl | 2-fluoro-phenyl | 434.9 | 8.13 | 2 |
| 2-40 | 4-chloro-6-methyl-pyridin-3-yl | phenyl | 370.8 | 6.16 | 2 |
| 2-41 | 4-chloro-2,6-dimethyl-pyridin-3-yl | phenyl | 384.8 | 5.24 | 2 |
| 2-42 | 6-chloro-4-methyl-pyridin-3-yl | 3-chloro-2-methoxy-phenyl | 436.9 | 7.90 | 2 |
| 2-43 | 2,6-dimethyl-pyridin-3-yl | 3-chloro-2-methoxy-phenyl | 414.7 | 4.60 | 2 |
| 2-44 | 4-chloro-2,6-dimethyl-pyridin-3-yl | 3-chloro-2-methoxy-phenyl | 450.7 | 5.84 | 2 |
| 2-45 | 6-methoxy-4-methyl-pyridin-3-yl | 3-chloro-2-methoxy-phenyl | 430.7 | 8.07 | 2 |
| 2-46 | 4-chloro-6-methyl-pyridin-3-yl | 3-chloro-2-methoxy-phenyl | 434.7 | 6.94 | 2 |
| 2-47 | 2-chloro-6-methyl-pyridin-3-yl | 3-chloro-2-methoxy-phenyl | 434.7 | 8.00 | 2 |
| 2-48 | 3-formyl-quinolin-2-yl | 2-methoxy-phenyl | 430.9 | 5.67 | 2 |
| 2-49 | 3-cyano-quinolin-2-yl | 2-methoxy-phenyl | 427.9 | 5.63 | 2 |
| 2-50 | 5-methyl-thieno[2,3-d]pyrimidin-4-yl | 2-methoxy-phenyl | 423.7 | 7.07 | 2 |
| 2-51 | 4,6-di-trifluoromethyl-2-hydroxy-phenyl | 2-methoxy-phenyl | 503.8 | 8.96 | 2 |
| 2-52 | 2,4-di-trifluoromethyl-phenyl | 2-methoxy-phenyl | 487.8 | 9.75 | 2 |
| 2-53 | 2-cyano-4-trifluoromethyl-phenyl | 2-methoxy-phenyl | 444.8 | 6.16 | 2 |
| 2-54 | 2,4-dichloro-phenyl | 2-methoxy-phenyl | 419.8 | 6.54 | 2 |
| 2-55 | 4-chloro-2-cyano-phenyl | 2-methoxy-phenyl | 410.8 | 6.04 | 2 |
| 2-56 | 5-chloro-pyridin-2-yl | 2-methoxy-phenyl | 387.0 | 9.38 | 3 |

-continued

| Ex. | A | (R₃)ₙ | MS (M + H)⁺ | $t_R$ (min) | HPLC Method |
|---|---|---|---|---|---|
| 2-57 | 5-chloro-3-methyl-pyridin-2-yl | 2-methoxy-phenyl | 400.8 | 7.83 | 2 |
| 2-58 | 3-chloro-5-methyl-pyridin-2-yl | 2-methoxy-phenyl | 400.7 | 7.46 | 2 |
| 2-59 | 3,5-difluoro-pyridin-2-yl | 2-methoxy-phenyl | 388.8 | 7.39 | 2 |
| 2-60 | 3,5-dimethyl-pyridin-2-yl | 2-methoxy-phenyl | 380.8 | 4.83 | 2 |
| 2-61 | 3-chloro-5-trifluoromethyl-pyridin-2-yl | 2-methoxy-phenyl | 454 | 8.65 | 2 |
| 2-62 | 5-chloro-3-methyl-pyridin-2-yl | 2-fluoro-phenyl | 388.8 | 7.94 | 2 |
| 2-63 | 5-chloro-3-methyl-pyridin-2-yl | 2,6-dimethyl-phenyl | 398.8 | 8.48 | 2 |
| 2-64 | 3-chloro-5-methyl-pyridin-2-yl | 2,6-dimethyl-phenyl | 398.8 | 8.07 | 2 |
| 2-65 | 3-chloro-5-trifluoromethyl-pyridin-2-yl | 2,6-dimethyl-phenyl | 452.7 | 9.21 | 2 |
| 2-66 | 3,5-difluoro-pyridin-2-yl | 2,6-dimethyl-phenyl | 386.8 | 8.02 | 2 |
| 2-66 | 3,5-dimethyl-pyridin-2-yl | 2,6-dimethyl-phenyl | 378.8 | 5.37 | 2 |
| 2-67 | 3-chloro-5-methyl-pyridin-2-yl | 2,3-dimethyl-phenyl | 399.0 | 8.03 | 2 |
| 2-68 | 3,5-dimethyl-pyridin-2-yl | 2,3-dimethyl-phenyl | 379.0 | 5.33 | 2 |
| 2-69 | 3,5-dichloro-pyridin-2-yl | 2-methoxy-6-methyl-phenyl | 436.9 | 10.08 | 2 |
| 2-70 | 3,5-dimethyl-pyridin-2-yl | 3-chloro-2-methoxy-phenyl | 414.7 | 5.38 | 2 |
| 2-71 | 5-chloro-3-methyl-pyridin-2-yl | 2,3-dimethyl-phenyl | 398.7 | 8.48 | 2 |
| 2-72 | 5-chloro-3-methyl-pyridin-2-yl | 2-benzoic acid methyl ester | 428.7 | 7.58 | 2 |
| 2-73 | 3,5-difluoro-pyridin-2-yl | 2-benzoic acid methyl ester | 416.7 | 7.15 | 2 |
| 2-74 | 3,5-dimethyl-pyridin-2-yl | 2-benzoic acid methyl ester | 408.8 | 4.71 | 2 |
| 2-75 | 3-chloro-5-trifluoromethyl-pyridin-2-yl | 2-benzoic acid methyl ester | 482.7 | 8.38 | 2 |
| 2-76 | 3-chloro-5-trifluoromethyl-pyridin-2-yl | 2-fluoro-phenyl | 442.9 | 8.64 | 2 |
| 2-77 | 3-chloro-5-methyl-pyridin-2-yl | 2-benzoic acid methyl ester | 428.7 | 7.21 | 2 |
| 2-78 | 3,5-dimethyl-pyridin-2-yl | 2-methoxy-6-methyl-phenyl | 394.8 | 7.25 | 2 |
| 2-79 | 3-methyl-quinolin-2-yl | 2-methoxy-phenyl | 416.9 | 6.67 | 2 |
| 2-80 | 3,5-dichloro-6-methyl-pyridin-2-yl | 2-methoxy-phenyl | 435 | 8.63 | 2 |
| 2-81 | 4-cyano-6-trifluoromethyl-pyridin-3-yl | 2-methylsulfanyl-phenyl | 461.9 | 6.19 | 4 |

Similarly, using 3-bromo-4-fluoro-benzoic acid as the starting material, 3-(4-cyano-6-trifluoromethyl-pyridin-3-yl)-4-fluoro-N-(2-methoxy-phenyl)-N-methyl benzamide 2-82 was prepared. MS: 430.0 (M+H)⁺; $t_R$=5.73 min (method 2).

Example 3

(2-{[4-chloro-3-(6-chloro-4-methyl-pyridin-3-yl)-benzoyl]-methyl-amino}-phenoxy)-acetic acid methyl ester

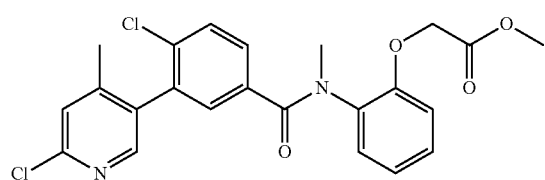 [SMILES: COC(=O)COc1ccccc1N(C)C(=O)c1ccc(Cl)c(-c2cnc(Cl)cc2C)c1]

Step 3A: 3-Bromo-4-chloro-N-(2-methoxy-phenyl)-N-methyl-benzamide (Alternate Synthesis)

To 3-bromo-4-chloro-benzoyl chloride (Step 2A, 14.4 mmol) in DCM (70 mL) cooled with an ice bath, was added methoxy-N-methylaniline (2 g, 14.6 mmol) in DCM (10 mL), followed by addition of diisopropylethylamine (3.4 mL, 18.95 mmol) slowly. Upon completion of the addition, the ice bath was removed and the mixture was stirred at room temperature for 48 hrs. The mixture was washed with 1 N HCl, saturated NaHCO₃, and brine, dried over Na₂SO₄, filtered and concentrated in vacuo to yield 3-bromo-4-chloro-N-(2-methoxy-phenyl)-N-methyl-benzamide as a solid (5.1 g, 96%). MS [M+H]⁺: 355.7; $t_R$=2.89 min. (method 1)

Similarly, 9.2 g (88%) 3-bromo-4-chloro-N-(2-methoxy-6-methyl-phenyl)-benzamide was prepared from 2-methoxy-6-methyl-phenylamine (4.2 g, 30.3 mmol). MS [M+H]⁺: 355.9; $t_R$=2.80 min. (method 1)

Similarly, 2.35 g (93%) of 3-bromo-4-chloro-N-(3-fluoro-2-methoxy-phenyl)-benzamide was prepared from 3-fluoro-2-methoxy-phenylamine (1 g, 7.08 mmol) with the difference that silica gel column chromatography (eluent: EtOAc/hexanes=1/4) was used for purification. MS[M+H]$^+$: 359.9; $t_R$=2.56 min. (method 1)

Step 3A.1: 3-Bromo-4-chloro-N-(2-methoxy-6-methyl-phenyl)-N-methyl-benzamide

This step was only used if the aniline used in step 3A was not N-methylated.

3-Bromo-4-chloro-N-(2-methoxy-6-methyl-phenyl)-N-methyl-benzamide (4.2 g) was prepared from 3-bromo-4-chloro-N-(2-methoxy-6-methyl-phenyl)-benzamide (4 g, 11.3 mmol) using the procedure of Step 2C. MS [M+H]$^+$: 369.9; $t_R$=2.89 min. (method 1)

Similarly, 2.3 g (98%) 3-bromo-4-chloro-N-(3-fluoro-2-methoxy-phenyl)-N-methyl-benzamide was prepared from 3-bromo-4-chloro-N-(3-fluoro-2-methoxy-phenyl)-benzamide (2.3 g, 6.4 mmol). Silica gel column chromatography was used for purification (eluent: EtOAc/hexanes=1/4 with gradient up to 2/3). MS [M+H]$^+$: 373.9; $t_R$=2.44 min. (method 1)

Step 3B: 3-Bromo-4-chloro-N-(2-hydroxy-phenyl)-N-methyl-benzamide

To a cooled solution (−70° C.) of 3-bromo-4-chloro-N-(2-methoxy-phenyl)-N-methyl-benzamide (2 g, 5.64 mmol) in DCM (20 mL), BBr$_3$ (1.7 mL, 18 mmol) was added drop-wise over a 20 minute period. The reaction temperature was allowed to increase to room temperature over 12 hrs until completion of the reaction. After concentration in vacuo the mixture was partitioned between DCM and water. 1N NaOH was added to increase pH to ~5. The organic layer was separated and washed with brine and dried over Na$_2$SO$_4$. Concentration and purification by silica gel column chromatography eluting with hexane/ethyl acetate (4/1 with gradient up to 3/2) yielded 3-bromo-4-chloro-N-(2-hydroxy-phenyl)-N-methyl-benzamide (1.78 g, 93%). MS [M+H]$^+$: 341.9; $t_R$=2.56 min. (method 1)

Similarly 1.9 g (100%) 3-bromo-4-chloro-N-(2-hydroxy-6-methyl-phenyl)-N-methyl-benzamide was prepared from 3-bromo-4-chloro-N-(2-methoxy-6-methyl-phenyl)-N-methyl-benzamide (2 g, 5.4 mmol). MS [M+H]$^+$: 355.9; $t_R$=2.60 min. (method 1)

Similarly 1.65 g (90%) of 3-bromo-4-chloro-N-(3-fluoro-2-hydroxy-phenyl)-N-methyl-benzamide was prepared from 3-bromo-4-chloro-N-(3-fluoro-2-methoxy-phenyl)-N-methyl-benzamide (1.9 g, 5.1 mmol). MS [M+H]$^+$: 359.9; $t_R$=2.22 min. (method 1)

Step 3C: {2-[(3-Bromo-4-chloro-benzoyl)-methyl-amino]-phenoxy}-acetic acid methyl ester A mixture of 3-bromo-4-chloro-N-(2-hydroxy-phenyl)-N-methyl-benzamide (442 mg, 1.3 mmol), methylbromoacetate (0.247 mL, 2.6 mmol) and K$_2$CO$_3$ (717 mg, 5.2 mmol) was heated in DMF (8 mL) at 80° C. for 5 hrs. After cooling to room temperature, the mixture was partitioned between ethyl acetate and water. The organic layer was separated and washed with brine, dried over Na$_2$SO$_4$, then purified by silica gel column chromatography eluted with ethyl acetate/hexane (1/4) to yield {2-[(3-bromo-4-chloro-benzoyl)-methyl-amino]-phenoxy}acetic acid methyl ester (495 mg). MS [M+H]$^+$: 413.9; $t_R$=2.75 min. (method 1)

4-{2-[(3-Bromo-4-chloro-benzoyl)-methyl-amino]-phenoxy}-butyric acid methyl ester (0.41 g) was similarly prepared in 72% yield. MS [M+H]$^+$: 441.9; $t_R$=2.87 min. (method 1)

5-{2-[(3-Bromo-4-chloro-benzoyl)-methyl-amino]-phenoxy}-pentanoic acid methyl ester (0.53 g) was similarly prepared in 99% yield. MS [M+H]$^+$: 456.0; $t_R$=2.94 min. (method 1)

4-{2-[(3-Bromo-4-chloro-benzoyl)-methyl-amino]-3-methyl-phenoxy}-butyric acid methyl ester (0.54 g) was similarly prepared in 85% yield. MS [M+H]$^+$: 456.0; $t_R$=2.94 min. (method 1)

4-{2-[(3-Bromo-4-chloro-benzoyl)-methyl-amino]-6-fluoro-phenoxy}-butyric acid methyl ester (0.93 g) was similarly prepared in 93% yield. MS [M+H]$^+$: 460.0; $t_R$=2.45 min. (method 1)

4-{2-[(3-Bromo-4-chloro-benzoyl)-methyl-amino]-3-methyl-phenoxy}-butyric acid tert-butyl ester (0.78 g) was similarly prepared in 79% yield. MS [M+H]$^+$: 498.1; $t_R$=2.75 min. (method 1)

Step 3D: (2-{[4-Chloro-3-(4,4,5,5-tetramethyl-[1,3,2]dioxaborolan-2-yl)-benzoyl]-methyl-amino}-phenoxy)-acetic acid methyl ester A mixture of {2-[(3-bromo-4-chloro-benzoyl)-methyl-amino]-phenoxy}-acetic acid methyl ester (495 mg, 1.2 mmol), bis(pinacolato)diboron (457 mg, 1.8 mmol), Pd(dppf)$_2$Cl$_2$ (70 mg, 2.4 mmol), potassium acetate (352 mg, 3.6 mmol) in dioxane (10 mL) was degassed by bubbling N$_2$ for 5 minutes and then was heated under sealed condition to 95° C. for 14 hrs. Upon cooling to room temperature, the mixture was diluted with ethyl acetate, washed with water and brine, and dried over Na$_2$SO$_4$. Concentration and purification by silica gel column chromatography eluting with ethyl acetate/hexane (3/7) yielded (2-{[4-chloro-3-(4,4,5,5-tetramethyl-[1,3,2]dioxaborolan-2-yl)-benzoyl]-methyl-amino}-phenoxy)-acetic acid methyl ester (0.61 g, 100% yield). MS [M+H]$^+$: 460.1; $t_R$=2.56 min (method 1)

Similarly, the following compounds were made from the corresponding aryl bromides:

4-(2-{[4-Chloro-3-(4,4,5,5-tetramethyl-[1,3,2]dioxaborolan-2-yl)-benzoyl]-methyl-amino}-phenoxy)-butyric acid methyl ester (0.47 g, 100% yield) MS [M+H]$^+$: 488; $t_R$=2.99 min (method 1)

4-(2-{[4-Chloro-3-(4,4,5,5-tetramethyl-[1,3,2]dioxaborolan-2-yl)-benzoyl]-methyl-amino}-3-methyl-phenoxy)-butyric acid methyl ester (0.6 g, 100% yield) MS [M+H]$^+$: 502.0; $t_R$=2.74 min (method 1)

4-(2-{[4-Chloro-3-(4,4,5,5-tetramethyl-[1,3,2]dioxaborolan-2-yl)-benzoyl]-methyl-amino}-6-fluoro-phenoxy)-butyric acid methyl ester (0.6 g, 100% yield) MS [M+H]$^+$: 506.2; $t_R$=2.59 min (method 1)

4-(2-{[4-Chloro-3-(4,4,5,5-tetramethyl-[1,3,2]dioxaborolan-2-yl)-benzoyl]-methyl-amino}-3-methyl-phenoxy)-butyric acid tert-butyl ester (0.39 g, 91% yield) MS [M+H]$^+$: 544.2; $t_R$=2.81 min (method 1).

Step 3D.1: Alternative Synthesis of 4-(2-{[4-chloro-3-(4,4,5,5-tetramethyl-[1,3,2]dioxaborolan-2-yl)-benzoyl]-methyl-amino}-3-methyl-phenoxy)-butyric acid tert-butyl ester 2-Amino-m-cresol (4.9 g, 40 mmol) was dissolved in a mixture of acetonitrile (90 mL) and water (80 mL) containing NaHCO$_3$ (6.7 g, 80 mmol) with vigorous stirring. 3-Bromo-4-chloro-benzoyl chloride (10.1 g, 40 mmol, Step 2A) was added in several portions and the mixture was stirred at room temperature for 3 hrs. The resulting precipitates were filtered, washed with water and tert-butyl methyl ether, then dried to yield 3-bromo-4-chloro-N-(2-hydroxy-6-methyl-phenyl)-benzamide (11.3 g). MS (M+H)$^+$: 339.7/341.7; $t_R$=2.36 min. (method 1)

A mixture of 3-bromo-4-chloro-N-(2-hydroxy-6-methyl-phenyl)-benzamide (11.3 g, 33.2 mmol), t-butyl 4-bromobutyrate (8.2 g, 36.6 mmol) and K$_2$CO$_3$ (9.2 g, 66.5 mmol) was heated in DMF (100 mL) at 60° C. for 14 hrs. The mixture was then concentrated to remove DMF and partitioned between ethyl acetate and water. The organic layer was separated and washed with water and brine, dried over MgSO$_4$, then purified by silica gel column chromatography eluting with ethyl acetate/hexane (1/4) to yield a red solid, which was further washed with ether to produce a white powder as 4-[2-(3-bromo-4-chloro-benzoylamino)-3-methyl-phenoxy]-butyric acid tert-butyl ester (10.2 g). MS [M-(t-Bu)+H]$^+$: 425.8/427.8; $t_R$=2.79 min. (method 1)

To a solution of 4-[2-(3-bromo-4-chloro-benzoylamino)-3-methyl-phenoxy]-butyric acid tert-butyl ester (10.2 g, 21.3 mmol) in dry DMF (100 mL) at 0° C. under N$_2$, NaH (60% in mineral oil, 1.7 g, 42.6 mmol) was added in several portions with stirring. 10 minutes later, iodomethane (2.0 mL, 32.1 mmol) was added. The mixture was warmed to room temperature by removal of ice bath and stirring was continued for 1 hr. Water (10 mL) was then added and organics were extracted by ethyl acetate, which was then washed by water and brine, and was dried over MgSO$_4$. After concentration, the crude product was purified by silica gel chromatography eluting with ethyl acetate/hexane (1/4) to yield 4-{2-[(3-bromo-4-chloro-benzoyl)-methyl-amino]-3-methyl-phenoxy}-butyric acid tert-butyl ester (9.5 g).

A mixture of 4-{2-[(3-bromo-4-chloro-benzoyl)-methyl-amino]-3-methyl-phenoxy}-butyric acid tert-butyl ester (6.1 g, 12.3 mmol), bis(pinacolato)diboron (4.7 g, 18.5 mmol), Pd(dppf)$_2$Cl$_2$ (0.73 g, 1.0 mmol) and potassium acetate (3.6 g, 36.9 mmol) in dioxane (80 mL) was degassed by bubbling N$_2$ for 5 minutes and then heated under sealed condition to 95° C. for 14 hrs. Upon cooling to room temperature, the mixture was passed through a pad of Celite. The Celite was further washed with ethyl acetate. The combined solutions were washed with water and brine, and were dried over MgSO$_4$. Concentration and purification by silica gel column chromatography eluting with ethyl acetate/hexane (1/4) yielded 4-(2-{[4-chloro-3-(4,4,5,5-tetramethyl-[1,3,2]dioxaborolan-2-yl)-benzoyl]-methyl-amino}-3-methyl-phenoxy)-butyric acid tert-butyl ester (6.5 g) as a light yellow oil.

4-(2-{[4-Chloro-3-(4,4,5,5-tetramethyl-[1,3,2]dioxaborolan-2-yl)-benzoyl]-methyl-amino-phenoxy)-butyric acid tert-butyl ester was prepared similarly. MS [M+H-isobutene]$^+$: 474.2; $t_R$=2.72 min. (method 1)

Step 3E: (2-{[4-Chloro-3-(6-chloro-4-methyl-pyridin-3-yl)-benzoyl]-methyl-amino}-phenoxy)-acetic acid methyl ester A mixture of (2-{[4-chloro-3-(4,4,5,5-tetramethyl-[1,3,2]dioxaborolan-2-yl)-benzoyl]-methyl-amino}-phenoxy)-acetic acid methyl ester (45 mg, 0.11 mmol), 5-bromo-2-chloro-4-methyl-pyridine (25 mg, 0.12 mmol), Pd(PPh$_3$)$_4$ (6.5 mg, 0.0056 mmol), and K$_2$CO$_3$ (38 mg, 0.28 mmol) in dioxane (600 ul), was heated at 95° C. for 12 hrs. The mixture was purified after a filtration by prep. LCMS to yield (2-{[4-chloro-3-(6-chloro-4-methyl-pyridin-3-yl)-benzoyl]-methyl-amino}-phenoxy)-acetic acid methyl ester 3-1. MS [M+H]$^+$: 459.0; $t_R$=7.70 min; (method 2)

The following compounds were prepared according to the procedures described above.

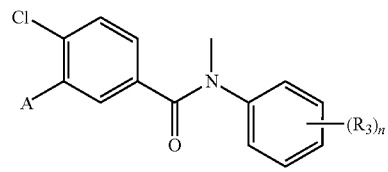

| Ex. | A | (R$_3$)$_n$ | MS ion | $t_R$ (min) | HPLC Method |
|---|---|---|---|---|---|
| 3-1 | 6-chloro-4-methyl-pyridin-3-yl | 2-[(methoxycarbonyl)methoxy]-phenyl | 459.0 | 7.70 | 2 |
| 3-2 | 6-chloro-4-methyl-pyridin-3-yl | 2-[3-(methoxycarbonyl)propyloxy]-phenyl | 487.0 | 8.21 | 2 |
| 3-3 | 6-cyano-4-methyl-pyridin-3-yl | 2-[(methoxycarbonyl)methoxy]-phenyl | 450.0 | 7.3 | 2 |
| 3-4 | 4-chloro-6-methyl-pyridin-3-yl | 2-[(methoxycarbonyl)methoxy]-phenyl | 459.0 | 6.13 | 2 |
| 3-5 | 6-chloro-4-methyl-pyridin-3-yl | 2-[3-(methoxycarbonyl)propyloxy]-6-methyl-phenyl | 500.9 | 8.80 | 2 |
| 3-6 | 6-chloro-4-methyl-pyridin-3-yl | 3-fluoro-2-[3-(methoxycarbonyl)propyloxy]-phenyl | 504.9 | 8.60 | 2 |
| 3-7 | 4-methyl-6-trifluoromethyl-pyridin-3-yl | 2-[3-(methoxycarbonyl)propyloxy]-phenyl | 521.3 | 8.89 | 2 |
| 3-8 | 6-cyano-4-methyl-pyridin-3-yl | 2-[3-(methoxycarbonyl)-propyloxy]-phenyl | 478.1 | 7.76 | 2 |
| 3-9 | 6-cyano-4-methyl-pyridin-3-yl | 2-[3-(methoxycarbonyl)propyloxy]-6-methyl-phenyl | 491.9 | 8.38 | 2 |
| 3-10 | 4-cyano-6-trifluoromethyl-pyridin-3-yl | 2-[3-(methoxycarbonyl)propyloxy]-phenyl | 531.8 | 8.88 | 2 |
| 3-11 | 4-cyano-6-trifluoromethyl-pyridin-3-yl | 2-[3-(methoxycarbonyl)propyloxy]-6-methyl-phenyl | 545.8 | 9.09 | 2 |
| 3-12 | 4-cyano-6-trifluoromethyl-pyridin-3-yl | 3-fluoro-2-[3-(methoxycarbonyl)propyloxy]-phenyl | 549.9 | 8.92 | 2 |
| 3-13 | 4-methyl-6-trifluoromethyl-pyridin-3-yl | 3-fluoro-2-[3-(methoxycarbonyl)propyloxy]-phenyl | 539.3 | 9.08 | 2 |
| 3-14 | 4-methyl-6-trifluoromethyl-pyridin-3-yl | 3-fluoro-2-[3-(methoxycarbonyl)propyloxy]-phenyl | 504.9 | 8.60 | 2 |
| 3-15 | 6-cyano-4-methyl-pyridin-3-yl | 3-fluoro-2-[3-(methoxycarbonyl)propyloxy]-phenyl | 495.9 | 8.21 | 2 |
| 3-16 | 4-methyl-6-trifluoromethyl-pyridin-3-yl | 2-[3-(t-butyloxycarbonyl)propyloxy]-phenyl | 577.2 | 10.54 | 2 |
| 3-17 | 3-chloro-5-trifluoromethyl-pyridin-2-yl | 2-[3-(t-butyloxycarbonyl)propyloxy]-phenyl | 596.9 | 10.68 | 2 |
| 3-18 | 3-cyano-quinolin-2-yl | 2-[3-(t-butyloxycarbonyl)propyloxy]-phenyl | 569.9 | 2.77 | 1 |
| 3-19 | 3-cyano-quinolin-2-yl | 2-[3-(t-butyloxycarbonyl)propyloxy]-phenyl | 499.7 | 10.61 | 2 |
| 3-20 | 4-cyano-2-methyl-phenyl | 2-[3-(t-butyloxycarbonyl)propyloxy]-phenyl | 519.8 | 2.63 | 1 |
| 3-21 | 4-cyano-6-trifluoromethyl-pyridin-3-yl | 2-[3-(t-butyloxycarbonyl)propyloxy]-phenyl | 517.9 | 2.89 | 1 |

-continued

| Ex. | A | (R₃)ₙ substituent | MS ion | $t_R$ (min) | HPLC Method |
|---|---|---|---|---|---|
| 3-22 | 4-cyano-6-trifluoromethyl-pyridin-3-yl | 2-[3-(t-butyloxycarbonyl)-propyloxy]-6-methyl-phenyl | 531.8 | 10.35 | 2 |
| 3-23 | 4-chloro-2-cyano-phenyl | 2-[3-(t-butyloxycarbonyl)-propyloxy]-phenyl | 482.9 | 6.63 | 4 |

Example 4

(2-{[4-Chloro-3-(6-chloro-4-methyl-pyridin-3-yl)-benzoyl]-methyl-amino}-phenoxy)acetic acid

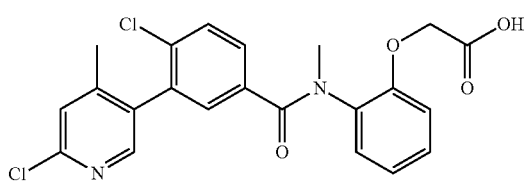 [SMILES: Cc1cc(Cl)ncc1-c1cc(C(=O)N(C)c2ccccc2OCC(=O)O)ccc1Cl]

Step 4A: (2-{[4-Chloro-3-(6-chloro-4-methyl-pyridin-3-yl)-benzoyl]-methyl-amino}phenoxy)-acetic acid (2-{[4-Chloro-3-(6-chloro-4-methyl-pyridin-3-yl)-benzoyl]-methyl-amino}-phenoxy)-acetic acid methyl ester (10 mg, 0.02 mmol) was dissolved in THF (300 μL) and 1M LiOH (100 μL) was added. The mixture was stirred at room temperature until LCMS indicated that starting material was completely consumed. The mixture was diluted with EtOAc and acidified with 1 N HCl. The organic layer was concentrated, dissolved in MeOH and purified by prep LCMS to yield (2-{[4-chloro-3-(6-chloro-4-methyl-pyridin-3-yl)-benzoyl]-methyl-amino}-phenoxy)-acetic acid 4-1. MS [M+H]⁺: 445.0; $t_R$=6.75 min, (method 2)

The following compounds were prepared according to the procedure described above. In cases where the molecule was substituted with a cyano group it should be noted that lithium hydroxide was added in 3 portions over a 90 minute period. Typically at 0.04 mmole of starting ester in 200 μL THF, a 1N solution of LiOH (60 μL) was added in 3×20 μL portions every 30 minutes. The reaction was allowed to proceed for 4 hours.

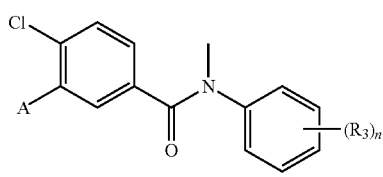

| Ex. | A | (R₃)ₙ substituent | MS (M + H)⁺ | $t_R$ (min) | HPLC method |
|---|---|---|---|---|---|
| 4-1 | 6-chloro-4-methyl-pyridin-3-yl | 2-[(hydroxycarbonyl)-methoxy]-phenyl | 445.0 | 6.75 | 2 |
| 4-2 | 6-chloro-4-methyl-pyridin-3-yl | 2-[3-(hydroxycarbonyl)-propyloxy]-phenyl | 473.0 | 7.17 | 2 |
| 4-3 | 6-chloro-4-methyl-pyridin-3-yl | 2-[3-(hydroxycarbonyl)-propyloxy]-6-methyl-phenyl | 486.8 | 7.71 | 2 |
| 4-4 | 6-chloro-4-methyl-pyridin-3-yl | 3-fluoro-2-[3-(hydroxycarbonyl)-propyloxy]-phenyl | 490.8 | 7.49 | 2 |
| 4-5 | 6-chloro-4-methyl-pyridin-3-yl | 2-[4-(hydroxycarbonyl)-butyloxy]-phenyl | 487.0 | 7.42 | 2 |
| 4-6 | 4-methyl-6-trifluoromethyl-pyridin-3-yl | 2-[3-(hydroxycarbonyl)-propyloxy]-phenyl | 507.1 | 4.82 | 2 |
| 4-7 | 4-methyl-6-trifluoromethyl-pyridin-3-yl | 3-fluoro-2-[3-(hydroxycarbonyl)-propyloxy]-phenyl | 525.1 | 3.77 | 2 |
| 4-8 | 6-cyano-4-methyl-pyridin-3-yl | 2-[3-(hydroxycarbonyl)-propyloxy]-6-methyl-phenyl | 477.9 | 7.35 | 2 |
| 4-9 | 6-cyano-4-methyl-pyridin-3-yl | 3-fluoro-2-[3-(hydroxycarbonyl)-propyloxy]-phenyl | 481.9 | 7.12 | 2 |
| 4-10 | 4-cyano-6-trifluoromethyl-pyridin-3-yl | 2-[3-(hydroxycarbonyl)-propyloxy]-phenyl | 517.8 | 7.84 | 2 |
| 4-11 | 4-cyano-6-trifluoromethyl-pyridin-3-yl | 2-[3-(hydroxycarbonyl)-propyloxy]-6-methyl-phenyl | 531.8 | 8.15 | 2 |
| 4-12 | 4-cyano-6-trifluoromethyl-pyridin-3-yl | 3-fluoro-2-[3-(hydroxycarbonyl)-propyloxy]-phenyl | 535.8 | 7.88 | 2 |

Example 5

4-(2-{[4-Chloro-3-(6-cyano-4-methyl-pyridin-3-yl)-benzoyl]-methyl-amino}-phenoxy)-butyric acid

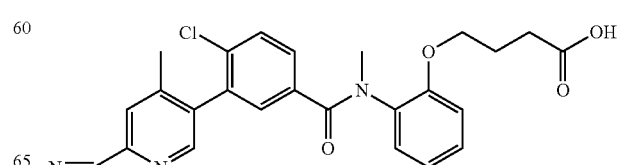

Step 5A: 4-(2-{[4-chloro-3-(6-cyano-4-methyl-pyridin-3-yl)-benzoyl]-methyl-amino}-phenoxy)-butyric acid 4-(2-{[4-Chloro-3-(6-cyano-4-methyl-pyridin-3-yl)-benzoyl]-methyl-amino}-phenoxy)-butyric acid tert-butyl ester (60 mg, 0.12 mmol) was stirred in a mixture of DCM (400 μL) and TFA (400 μL) for 1 hr. The mixture was concentrated, dissolved in MeOH and purified by prep LCMS to yield 4-(2-{[4-chloro-3-(6-cyano-4-methyl-pyridin-3-yl)-benzoyl]-methyl-amino}-phenoxy)-butyric acid 5-1. MS [M+H]$^+$: 463.7; $t_R$=3.46 min, (method 2)

The following compounds were prepared according to the procedure described above.

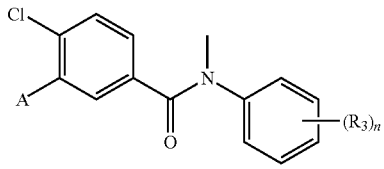

| Ex. | A | 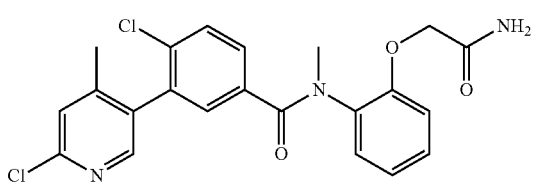 [SMILES: Cc1cc(Cl)ncc1-c1cc(C(=O)N(C)c2ccccc2OCC(N)=O)ccc1Cl] (R$_3$)$_n$ | MS (M + H)$^+$ | $t_R$ (min) | Method |
|---|---|---|---|---|---|
| 5-1 | 6-cyano-4-methyl-pyridin-3-yl | 2-[3-(hydroxycarbonyl)-propyloxy]-phenyl | 463.7 | 3.46 | 2 |
| 5-2 | 4-methyl-6-trifluoromethyl-pyridin-3-yl | 2-[3-(hydroxycarbonyl)-propyloxy]-6-methyl-phenyl | 521.2 | 8.13 | 2 |
| 5-3 | 3-chloro-5-trifluoromethyl-pyridin-2-yl | 2-[3-(hydroxycarbonyl)-propyloxy]-6-methyl-phenyl | 540.8 | 8.17 | 2 |
| 5-4 | 3-cyano-quinolin-2-yl | 2+3-(hydroxycarbonyl)-propyloxy]-6-methyl-phenyl | 513.8 | 4.78 | 2 |
| 5-5 | 3-cyano-quinolin-2-yl | 2-[3-(hydroxycarbonyl)-propyloxy]-phenyl | 500.2 | 24.60 | 5 |
| 5-6 | 4-chloro-2-cyano-phenyl | 2-[3-(hydroxycarbonyl)-propyloxy]-phenyl | 482.8 | 7.81 | 2 |

Example 6

N-(2-Carbamoylmethoxy-phenyl)-4-chloro-3-(6-chloro-4-methyl-pyridin-3-yl)-N-methyl-benzamide

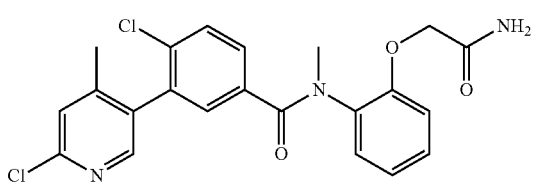 [SMILES: Cc1cc(Cl)ncc1-c1cc(C(=O)N(C)c2ccccc2OCC(N)=O)ccc1Cl]

Step 6A: N-(2-Carbamoylmethoxy-phenyl)-4-chloro-3-(6-chloro-4-methyl-pyridin-3-yl)-N-methyl-benzamide (2-{[4-Chloro-3-(6-chloro-4-methyl-pyridin-3-yl)-benzoyl]-methyl-amino}-phenoxy)-acetic acid methyl ester (28 mg, 0.06 mmol) was dissolved in 7N ammonia in MeOH (1 mL) and stirred at room temperature until starting material was consumed. The mixture was concentrated and taken up in MeOH, filtered and washed with methanol to yield N-(2-carbamoylmethoxy-phenyl)-4-chloro-3-(6-chloro-4-methyl-pyridin-3-yl)-N-methyl-benzamide 6-1. MS [M+H]$^+$: 444.0; $t_R$=6.25 min; (method 2)

Similarly, N-[2-(3-carbamoyl-propoxy)-phenyl]-4-chloro-3-(6-chloro-4-methyl-pyridin-3-yl)-N-methyl-benzamide 6-2, MS [M+H]$^+$: 472.0; $t_R$=6.51 min; (method 2) and N-[2-(4-carbamoyl-butoxy)-phenyl]-4-chloro-3-(6-chloro-4-methyl-pyridin-3-yl)-N-methyl-benzamide 6-3, MS [M+H]$^+$: 485.9; $t_R$=6.87 min; (method 2) were prepared.

Example 7

4-Chloro-3-(4,6-dichloro-pyridin-3-yl)-N-[2-(2-dimethylamino-ethoxy)-phenyl]-N-methyl-benzamide

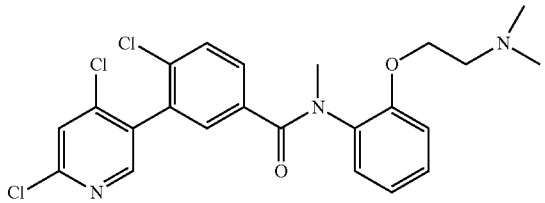 [SMILES: CN(C)CCOc1ccccc1N(C)C(=O)c1ccc(Cl)c(-c2cnc(Cl)cc2Cl)c1]

Step 7A: 3-Bromo-4-chloro-N-[2-(2-dimethylamino-ethoxy)-phenyl]-N-methyl-benzamide A mixture of 3-bromo-4-chloro-N-(2-hydroxy-phenyl)-N-methyl-benzamide (404 mg, 1.18 mmol, Step 3B), β-dimethylaminobromide hydrobromide (553 mg, 2.38 mmol) and K$_2$CO$_3$ (655 mg, 4.75 mmol) was heated in DMF (7 mL) at 80° C. for 14 hrs. The mixture was then diluted with ethyl acetate and water. The organic layer was separated and washed with water and brine, dried over Na$_2$SO$_4$, then purified by silica gel column chromatography eluting with DCM/MeOH (95/5 with gradient to 9/1) to yield 3-bromo-4-chloro-N-[2-(2-dimethylamino-ethoxy)-phenyl]-N-methyl-benzamide (97 mg). MS [M+H]$^+$: 412.7; $t_R$=2.24 min. (method 1)

Step 7B: 4-Chloro-3-(4,6-dichloro-pyridin-3-yl)-N-[2-(2-dimethylamino-ethoxy)-phenyl]-N-methyl benzamide A mixture of dioxane (1.0 mL) containing 3-bromo-4-chloro-N-[2-(2-dimethylamino-ethoxy)-phenyl]-N-methyl-benzamide (44.0 mg, 0.11 mmol), Pd$_2$(dba)$_3$ (10 mg, 0.01 mmol), P(t-Bu)$_3$HBF$_4$ (7 mg, 0.022 mmol), KF (22 mg, 0.38 mmol) and 2,4 dichloropyridine-5-boronic acid (21 mg, 0.11 mmol) was degassed by bubbling N$_2$ for 5 minutes and then sealed and heated at 110° C. overnight. The mixture was filtered and purified by preparative LCMS to yield 4-chloro-3-(4,6-dichloro-pyridin-3-yl)-N-[2-(2-dimethylaminoethoxy)-phenyl]-N-methyl benzamide 7-1. MS [M+H]⁺: 478.0; $t_R$=5.26 min. (method 2)

Example 8

4-Chloro-3-(6-cyano-4-methyl-pyridin-3-yl)-N-(2-hydroxy-phenyl)-N-methyl-benzamide

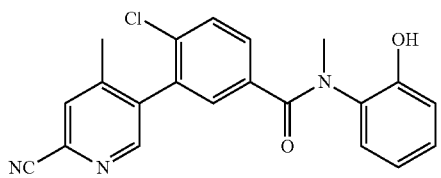 [SMILES: Cc1cc(C#N)ncc1-c1cc(C(=O)N(C)c2ccccc2O)ccc1Cl]

Step 8A: 4-Chloro-N-(2-hydroxy-phenyl)-N-methyl-3-(4,4,5,5-tetramethyl-[1,3,2]dioxaborolan-2-yl)-benzamide A mixture of 3-bromo-4-chloro-N-(2-hydroxy-phenyl)-N-methyl-benzamide (485 mg, 1.42 mmol, Step 3B), bis(pinacolato)diboron (0.543 g, 2.1 mmol), Pd(dppf)₂Cl₂ (83 mg, 0.11 mmol) and potassium acetate (419 mg, 4.3 mmol) in dioxane (10 mL) was degassed by bubbling N₂ for 5 minutes and then heated under sealed condition to 95° C. for 14 hrs. Upon cooling to room temperature, the mixture was diluted with ethyl acetate and washed with water and brine, then dried over Na₂SO₄. Concentration followed by purification by silica gel column chromatography eluting with ethyl acetate/hexane (1/4 up to 2/3) gave 4-chloro-N-(2-hydroxy-phenyl)-N-methyl-3-(4,4,5,5-tetramethyl-[1,3,2]dioxaborolan-2-yl)-benzamide (540 mg). MS [M+H]⁺: 388.1; $t_R$=2.74 min. (method 1)

Step 8B: 4-Chloro-3-(6-cyano-4-methyl-pyridin-3-yl)-N-(2-hydroxy-phenyl)-N-methyl-benzamide A mixture of 4-chloro-N-(2-hydroxy-phenyl)-N-methyl-3-(4,4,5,5-tetramethyl-[1,3,2]dioxaborolan-2-yl)-benzamide (100 mg, 0.26 mmol), 5-bromo-4-methyl-pyridine-2-carbonitrile (61 mg, 0.31 mmol), Pd(PPh₃)₄ (15 mg, 0.013 mmol), K₂CO₃ (90 mg, 0.65 mmol) in dioxane (1.2 mL), was heated at 95° C. for 12 hrs. The mixture was diluted with EtOAc, washed with water and brine, dried (Na₂SO₄) and concentrated in vacuo. Silica gel column chromatography (eluent: ethyl acetate/hexane (1/4 up to 4/1)) yielded 4-chloro-3-(6-cyano-4-methyl-pyridin-3-yl)-N-(2-hydroxy-phenyl)-N-methyl-benzamide 8-1 (68 mg).

The following compounds were prepared according to the procedure described above.

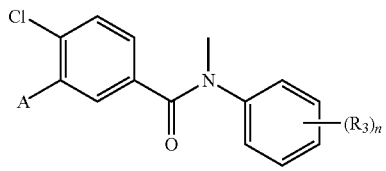

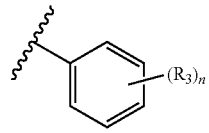

| Ex. | A | | MS (M + H)⁺ | $t_R$ (min) method 1 |
|---|---|---|---|---|
| 8-1 | 6-cyano-4-methyl-pyridin-3-yl | 2-hydroxy-phenyl | 378.1 | 2.22 |
| 8-2 | 6-chloro-4-methyl-pyridin-3-yl | 2-hydroxy-phenyl | 387.0 | 2.27 |
| 8-3 | 4-methyl-6-trifluoromethyl-pyridin-3-yl | 2-hydroxy-phenyl | 421.0 | 2.36 |
| 8-4 | 4-cyano-6-trifluoromethyl-pyridin-3-yl | 2-hydroxy-phenyl | 432.0 | 2.32 |
| 8-5 | 6-cyano-4-methyl-pyridin-3-yl | 2-hydroxy-6-methyl-phenyl | 392.1 | 2.25 |
| 8-6 | 4-methyl-6-trifluoromethyl-pyridin-3-yl | 2-hydroxy-6-methyl-phenyl | 435.1 | 2.41 |
| 8-7 | 4-cyano-6-trifluoromethyl-pyridin-3-yl | 2-hydroxy-6-methyl-phenyl | 446.1 | 2.33 |

Example 9

4-Chloro-3-(6-cyano-4-methyl-pyridin-3-yl)-N-[2-(3-hydroxy-propoxy)-phenyl]-N-methyl-benzamide

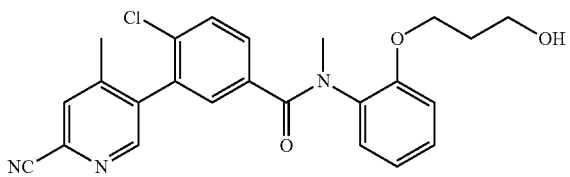 [SMILES: Cc1cc(C#N)ncc1-c1cc(C(=O)N(C)c2ccccc2OCCCO)ccc1Cl]

Step 9A: 4-Chloro-3-(6-cyano-4-methyl-pyridin-3-yl)-N-[2-(3-hydroxy-propoxy)-phenyl]-N-methyl-benzamide A mixture of 4-chloro-3-(6-cyano-4-methyl-pyridin-3-yl)-N-(2-hydroxy-phenyl)-N-methyl-benzamide 8-1 (50 mg, 0.13 mmol), 4-bromopropanol (18 μL, 0.2 mmol) and K₂CO₃ (55 mg, 0.40 mmol) in DMF (0.4 mL) was stirred at room temperature for 14 hrs. Ethyl acetate was added and the combined organic layers were washed with water, dried over Na₂SO₄, then purified by silica gel column chromatography eluting with ethyl acetate/hexane (2/3) up to 100% EtOAc to yield 4-chloro-3-(6-cyano-4-methyl-pyridin-3-yl)-N-[2-(3-hydroxy-propoxy)-phenyl]-N-methyl-benzamide (30 mg). Example 1. MS [M+H]⁺: 436.1; $t_R$=2.19 min. (method 1)

The following compounds were prepared according to the procedure described above.

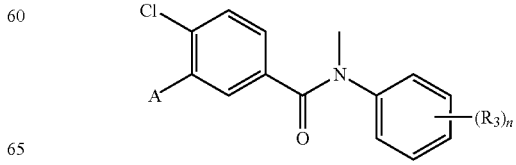

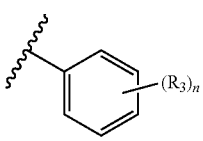

| Ex. | A | (R₃)ₙ | MS (M + H)⁺ | HPLC $t_R$ (min) | Method |
|---|---|---|---|---|---|
| 9-1 | 6-cyano-4-methyl-pyridin-3-yl | 2-(3-hydroxy-propoxy)-phenyl | 436.1 | 2.18 | 1 |
| 9-2 | 6-chloro-4-methyl-pyridin-3-yl | 2-(3-hydroxy-propoxy)-phenyl | 445.1 | 2.26 | 1 |
| 9-3 | 4-methyl-6-trifluoromethyl-pyridin-3-yl | 2-(3-hydroxy-propoxy)-phenyl | 479.1 | 2.33 | 1 |
| 9-4 | 4-cyano-6-trifluoromethyl-pyridin-3-yl | 2-(3-hydroxy-propoxy)-phenyl | 490.1 | 2.30 | 1 |
| 9-5 | 6-cyano-4-methyl-pyridin-3-yl | 2-(3-hydroxy-propoxy)-6-methyl-phenyl | 449.9 | 7.00 | 2 |
| 9-6 | 4-methyl-6-trifluoromethyl-pyridin-3-yl | 2-(3-hydroxy-propoxy)-6-methyl-phenyl | 492.1 | 2.40 | 1 |
| 9-7 | 4-cyano-6-trifluoromethyl-pyridin-3-yl | 2-(3-hydroxy-propoxy)-6-methyl-phenyl | 504.1 | 2.34 | 1 |

Example 10

4-Chloro-3-(2-cyano-4-trifluoromethyl-phenyl)-N-[2-(3-hydroxy-propoxy)-6-methyl-phenyl]-N-methyl-benzamide

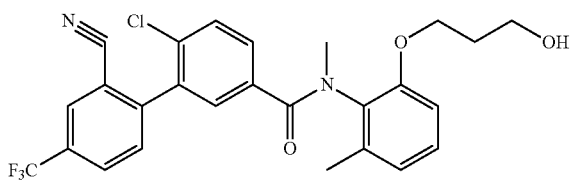 [SMILES: Cc1cccc(OCCCO)c1N(C)C(=O)c1ccc(Cl)c(-c2ccc(C(F)(F)F)cc2C#N)c1]

Step 10A: 3-Bromo-4-chloro-N-[2-(3-hydroxy-propoxy)-6-methyl-phenyl]-N-methyl-benzamide 3-Bromo-1-propanol (2.48 mL, 27.3 mmol) was added to a solution of 3-bromo-4-chloro-N-(2-hydroxy-6-methyl-phenyl)-N-methyl-benzamide (6.47 g, 18.3 mmol, Step 3B) in DMF (80 mL). To this was added $K_2CO_3$ (3.3 g, 24 mmol) and the mixture was stirred at room temperature for approximately 16 hrs. At this time the reaction was neutralized with 1N hydrochloric acid and the mixture was extracted with ethyl acetate. The organic layer was washed with first water and then brine solution. The organic filtrate was evaporated and the residue purified using column chromatography in a gradient of 50% ethyl acetate to 60% ethyl acetate in hexanes giving 3-bromo-4-chloro-N-[2-(3-hydroxy-propoxy)-6-methyl-phenyl]-N-methyl-benzamide (5.7 g, 76%). MS [M+H]⁺: 413.9; $t_R$=2.29 min. (method 1)

Similarly, 3-bromo-4-chloro-N-[2-(3-hydroxy-propoxy)-phenyl]-N-methyl-benzamide was prepared from the corresponding 3-bromo-4-chloro-N-(2-hydroxy-phenyl)-N-methyl-benzamide (Step 3B). MS [M+H]⁺: 399.6; $t_R$=2.21 min. (method 1)

Step 10B: 4-chloro-N-[2-(3-hydroxy-propoxy)-6-methyl-phenyl]-N-methyl-3-(4,4,5,5-tetramethyl-[1,3,2]dioxaborolan-2-yl)-benzamide A mixture of 3-bromo-4-chloro-N-[2-(3-hydroxy-propoxy)-6-methyl-phenyl]-N-methyl-benzamide (5.5 g, 13.4 mmol), bis(pinnacolato)diboron (5.1 g, 20.0 mmol), $PdCl_2(dppf)_2$ (781.7 mg, 1.1 mmol) and KOAc (3.92 g, 40.1 mmol) in dioxane (70 mL), was heated at 95° C. for approximately 16 hrs after degassing of the solvent with a stream of nitrogen. The mixture was allowed to cool to room temperature and then filtered over a celite pad. The pad was further washed with EtOAc. The combined organics were washed with water and brine and dried with $MgSO_4$. The filtrate from this was concentrated in vacuo and the residue purified by silica gel column chromatography (eluent: 20% ethyl acetate in hexane) to afford 4-chloro-N-[2-(3-hydroxy-propoxy)-6-methyl-phenyl]-N-methyl-3-(4,4,5,5-tetramethyl-[1,3,2]dioxaborolan-2-yl)-benzamide (5.5 g). MS [M+H]⁺: 460.1; $t_R$=2.47 min. (method 1)

Similarly, 4-chloro-N-[2-(3-hydroxy-propoxy)-phenyl]-N-methyl-3-(4,4,5,5-tetramethyl-[1,3,2]dioxaborolan-2-yl)-benzamide was prepared. MS [M+H]⁺: 446.0; $t_R$=2.42 min. (method 1)

Step 10C: 4-chloro-3-(2-cyano-4-trifluoromethyl-phenyl)-N-[2-(3-hydroxy-propoxy)-6-methyl-phenyl]-N-methyl-benzamide A mixture of 4-chloro-N-[2-(3-hydroxy-propoxy)-6-methyl-phenyl]-N-methyl-3-(4,4,5,5-tetramethyl-[1,3,2]dioxaborolan-2-yl)-benzamide (206 mg, 0.45 mmol), 2-bromo-5-(trifluoromethyl)-benzonitrile (75 mg, 0.3 mmol), $Pd(PPh_3)_4$ (34.7 mg, 0.03 mmol), $Na_2CO_3$ (190.8 mg, 1.8 mmol) in dioxane/water (9/1, 1.5 mL), was heated at 95° C. for approximately 16 hrs after degassing of the solvent with a stream of nitrogen. The reaction was allowed to cool to room temperature. The mixture was diluted with water and extracted with ethyl acetate. The organic layer was further washed with brine and dried with $MgSO_4$. The filtrate was evaporated and the residue purified by preparative TLC [eluent: 40% acetone in hexane] to afford 4-chloro-3-(2-cyano-4-trifluoromethyl-phenyl)-N-[2-(3-hydroxy-propoxy)-6-methyl-phenyl]-N-methyl-benzamide 10-1 (120 mg). MS [M+H]⁺: 502.9; $t_R$=8.15 min. (method 2)

Similarly, 4-chloro-3-(3-cyano-quinolin-2-yl)-N-[2-(3-hydroxy-propoxy)-phenyl]-N-methyl-benzamide 10-2 was prepared. MS [M+H]⁺: 471.9; $t_R$=6.89 min. (method 2)

Example 11

3-(2-{[4-Chloro-3-(6-cyano-4-methyl-pyridin-3-yl)-benzoyl]-methyl-amino}-phenoxy)-propionic acid

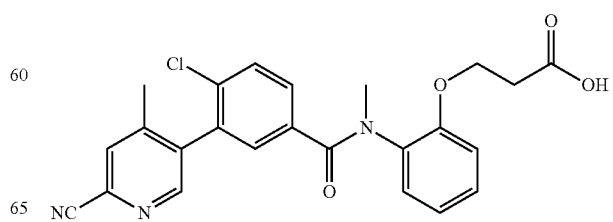

Step 11A: 3-(2-{[4-Chloro-3-(6-cyano-4-methyl-pyridin-3-yl)-benzoyl]-methyl-amino}-phenoxy)-propionic acid To a mixture of 4-chloro-3-(6-cyano-4-methyl-pyridin-3-yl)-N-[2-(3-hydroxy-propoxy)-phenyl]-N-methyl-benzamide 9-1 (30 mg, 0.07 mmol) in acetonitile (0.25 mL) and dichloromethane (0.25 mL), a solution of sodium periodate (40 mg, 0.19 mmol) in water (0.4 mL) was added followed by ruthenium (III) chloride (2 mg, 0.0096 mmol). The mixture was stirred 15 min, diluted with MeOH, stirred for 15 min and filtered. The filtrate was purified by prep. LCMS to yield 3-(2-{[4-chloro-3-(6-cyano-4-methyl-pyridin-3-yl)-benzoyl]-methyl-amino}-phenoxy)-propionic acid 11-1. MS [M+H]$^+$: 449.8; $t_R$=6.76 min. (method 2)

The following compounds were prepared according to the procedure described above.

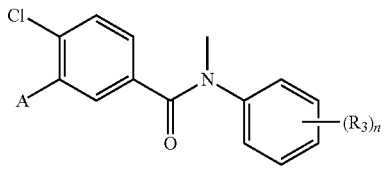

| Ex. | A | (R$_3$)$_n$ | MS (M + H)$^+$ | $t_R$ (min) method 2 |
|---|---|---|---|---|
| 11-1 | 6-cyano-4-methyl-pyridin-3-yl | 2-[2-(hydroxycarbonyl)-ethoxy]-phenyl | 449.8 | 6.76 |
| 11-2 | 6-chloro-4-methyl-pyridin-3-yl | 2-[2-(hydroxycarbonyl)-ethoxy]-phenyl | 458.8 | 7.13 |
| 11-3 | 4-methyl-6-trifluoromethyl-pyridin-3-yl | 2-[2-(hydroxycarbonyl)-ethoxy]-phenyl | 492.9 | 7.60 |
| 11-4 | 4-cyano-6-trifluoromethyl-pyridin-3-yl | 2-[2-(hydroxycarbonyl)-ethoxy]-phenyl | 503.8 | 7.62 |
| 11-5 | 4-methyl-6-trifluoromethyl-pyridin-3-yl | 2-[2-(hydroxycarbonyl)-ethoxy]-6-methyl-phenyl | 506.9 | 7.88 |
| 11-6 | 6-cyano-4-methyl-pyridin-3-yl | 2-[2-(hydroxycarbonyl)-ethoxy]-6-methyl-phenyl | 463.9 | 7.04 |
| 11-7 | 4-cyano-6-trifluoromethyl-pyridin-3-yl | 2-[2-(hydroxycarbonyl)-ethoxy]-6-methyl-phenyl | 517.8 | 7.85 |
| 11-8 | 2-cyano-4-trifluoromethyl-phenyl | 2-[2-(hydroxycarbonyl)-ethoxy]-6-methyl-phenyl | 516.8 | 8.17 |
| 11-9 | 3-cyano-quinolin-2-yl | 2-[2-(hydroxycarbonyl)-ethoxy]-phenyl | 485.9 | 6.96 |

Example 12

5-(2-{[4-Chloro-3-(6-chloro-4-methyl-pyridin-3-yl)-benzoyl]-methyl-amino}-phenoxy)-pentanoic acid methyl ester

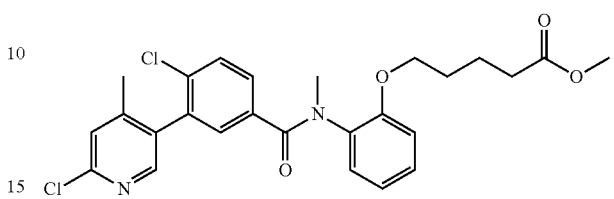

Step 12A: 4-Chloro-3-(6-chloro-4-methyl-pyridin-3-yl)-N-(2-hydroxy-phenyl)-N-methyl-benzamide A mixture of 4-chloro-N-(2-hydroxy-phenyl)-N-methyl-3-(4,4,5,5-tetramethyl-[1,3,2]dioxaborolan-2-yl)-benzamide (100 mg, 0.26 mmol, Step 8A), 5-bromo-2-chloro-4-methyl-pyridine (200 mg, 0.52 mmol), Pd(PPh$_3$)$_4$ (30 mg, 0.026 mmol), K$_2$CO$_3$ (180 mg, 1.3 mmol) in dioxane (2.5 mL), was heated at 100° C. for 12 hrs. The mixture was dried in vacuo in the presence of silica gel and directly chromatographed on silica gel (eluent: ethyl acetate/hexane (1/4 up to 2/3)) to yield 4-chloro-3-(6-chloro-4-methyl-pyridin-3-yl)-N-(2-hydroxy-phenyl)-N-methyl-benzamide (120 mg). MS [M+H]$^+$: 387.0; $t_R$=2.27 min. (method 1)

Step 12B: 5-(2-{[4-chloro-3-(6-chloro-4-methyl-pyridin-3-yl)-benzoyl]-methyl-amino}-phenoxy)-pentanoic acid methyl ester A mixture of 4-chloro-3-(6-chloro-4-methyl-pyridin-3-yl)-N-(2-hydroxy-phenyl)-N-methyl-benzamide (108 mg, 0.28 mmol), bromo methylvalerate (60 µL, 0.42 mmol) and K$_2$CO$_3$ (116 mg, 0.84 mmol) in DMF (1 mL) was stirred at room temperature for 14 hrs. Ethyl acetate was added and the combined organic layers were washed with water, dried over MgSO$_4$, then purified by silica gel column chromatography eluted with ethyl acetate/hexane (1/4) up to 1/3 to yield 5-(2-{[4-chloro-3-(6-chloro-4-methyl-pyridin-3-yl)-benzoyl]-methyl-amino}-phenoxy)-pentanoic acid methyl ester 12-1 (50 mg). MS [M+H]$^+$: 501; $t_R$=8.52 min. (method 1)

Example 13

4-(2-{[4-Chloro-3-(6-chloro-4-methyl-pyridin-3-yl)-benzoyl]-methyl-amino}-phenyl)-butyric acid methyl ester

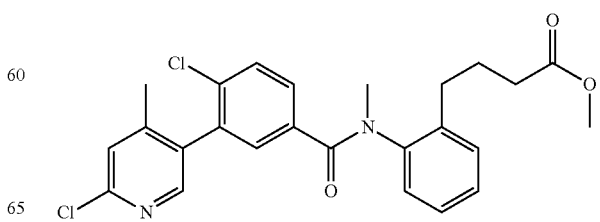

Step 13A: 1,3,4,5-tetrahydrobenzo[b]azepin-2-one

To a solution of α-tetralone (10 g, 68.5 mmol) in anhydrous MeOH (175 mL), hydroxylamine hydrochloride (7.6 g, 109.6 mmol) and triethylamine (15.3 mL, 109.6 mmol) were added. The mixture was stirred at room temperature for 16 hrs, followed by removal of the solvent in vacuo. The residue was dissolved in DCM, washed with water and brine, dried ($Na_2SO_4$), filtered and concentrated in vacuo to yield crude 3,4-dihydro-2H-naphthalen-1-one oxime (12 g). MS [M+H]$^+$: 162.1; $t_R$=2.03 min. (method 1)

To 3,4-dihydro-2H-naphthalen-1-one oxime (5 g, 31 mmol), PPA (50 g) was added and the mixture was heated at 120° C. for 4.5 hrs. While hot the mixture was quenched in a slurry of ice and water and vigorously stirred until a precipitate formed. The precipitate was filtered and rinsed with water to yield 1,3,4,5-tetrahydrobenzo[b]azepin-2-one (3.1 g). MS [M+H]$^+$: 162.0; $t_R$=1.76 min. (method 1)

Step 13B: 4-(2-Amino-phenyl)-butyric acid methyl ester

To 1,3,4,5-tetrahydro-benzo[b]azepin-2-one (1 g, 6.2 mmol) in MeOH (8 mL), concentrated sulfuric acid (0.5 mL) was added and the mixture was stirred at room temperature for 2 hrs and at 70° C. for an additional hr. The solvent was removed and DCM and water were added. The organic layer was removed and the aqueous layer was basified with sat $NaHCO_3$ and extracted with EtOAc (3×). The combined organic layers were washed with brine, dried ($Na_2SO_4$) and concentrated in vacuo to yield 4-(2-amino-phenyl)-butyric acid methyl ester (0.93 g). MS [M+H]$^+$: 194.1; $t_R$=1.49 min. (method 1)

Step 13C: 4-[2-(3-bromo-4-chloro-benzoylamino)-phenyl]-butyric acid methyl ester To 3-bromo-4-chloro-benzoyl chloride (1.09 g, 4.3 mmol) in DCM (30 mL) cooled with an ice bath, was added 4-(2-amino-phenyl)-butyric acid methyl ester (0.85 g, 4.4 mmol), followed by addition of diisopropylethylamine (1 mL, 5.6 mmol) slowly. Upon the completion of the addition, ice bath was removed and the mixture was stirred at room temperature for 12 hrs. The mixture was further diluted with DCM, washed with saturated $NaHCO_3$, 1N HCl, brine and dried over $Na_2SO_4$ and concentrated to yield 4-[2-(3-bromo-4-chloro-benzoylamino)-phenyl]-butyric acid methyl ester (1.8 g). MS [M+H]$^+$: 411.7; $t_R$=2.45 min. (method 1)

Step 13D: 4-{2-[(3-Bromo-4-chloro-benzo-methyl-amino]-phenyl}-butyric acid methyl ester To 4-[2-(3-bromo-4-chloro-benzoylamino)-phenyl]-butyric acid methyl ester (1.04 g, 2.54 mmol) in DMF (10 mL) at 0-5° C., was added NaH (152 mg, 3.81 mmol, 60% in mineral oil) in two portions. The mixture was stirred for 15 min at 0° C. and 15 min at rt. After addition of iodomethane (316 μl, 5.08 mmol), the mixture was stirred at room temperature for 12 hrs and was partitioned between ethyl acetate and citric acid. The separated organic layer was then washed with brine and dried over $Na_2SO_4$. Concentration and purification by silica gel column chromatography eluting with hexane/ethyl acetate (4/1) up to hexane/ethyl acetate (3/2) yielded 4-{2-[(3-bromo-4-chloro-benzoyl)-methyl-amino]-phenyl}-butyric acid methyl ester (1.0 g). MS [M+H]$^+$: 426.0; $t_R$=2.46 min. (method 1)

Step 13E: 4-(2-{[4-Chloro-3-(4,4,5,5-tetramethyl-[1,3,2]dioxaborolan-2-yl)-benzoyl]-methyl-amino}-phenyl)-butyric acid methyl ester A mixture of 4-{2-[(3-bromo-4-chloro-benzoyl)-methyl-amino]-phenyl}-butyric acid methyl ester (500 mg, 1.18 mmol), bis(pinacolato)diboron (448 mg, 1.76 mmol), Pd(dppf)$_2$Cl$_2$ (69 mg, 0.094 mmol) and potassium acetate (347 mg, 3.54 mmol) in dioxane (10 mL) was degassed by bubbling $N_2$ for 5 minutes and then heated under sealed condition to 95° C. for 14 hrs. Upon cooling to room temperature, the mixture was diluted with ethyl acetate and washed with water and brine, then dried over $Na_2SO_4$. Concentration and purification by silica gel column chromatography eluting with ethyl acetate/hexane (1/4 up to 2/3) gave 4-(2-{[4-chloro-3-(4,4,5,5-tetramethyl-[1,3,2]dioxaborolan-2-yl)-benzoyl]-methyl-amino}-phenyl)-butyric acid methyl ester as an oil (601 mg). MS [M+H]$^+$: 472.2; $t_R$=2.57 min. (method 1)

Step 13F: 4-(2-{[4-Chloro-3-(6-chloro-4-methyl-pyridin-3-yl)-benzoyl]-methyl-amino}-phenyl)-butyric acid methyl ester A mixture of 4-(2-{[4-chloro-3-(4,4,5,5-tetramethyl-[1,3,2]dioxaborolan-2-yl)-benzoyl]-methyl-amino}-phenyl)-butyric acid methyl ester (50 mg, 0.11 mmol), 5-bromo-2-chloro-pyridine (26 mg, 0.13 mmol), Pd(PPh$_3$)$_4$ (6 mg, 0.005 mmol), $K_2CO_3$ (36 mg, 0.18 mmol) in dioxane (0.6 mL), was heated at 100° C. for 12 hrs. The mixture was purified after a filtration by prep. LCMS to yield 4-(2-{[4-chloro-3-(6-chloro-4-methyl-pyridin-3-yl)-benzoyl]-methyl-amino}-phenyl)-butyric acid methyl ester 13-1. MS [M+H]$^+$: 470.9; $t_R$=8.41 min. (method 2).

The following compounds were prepared according to the procedure described above.

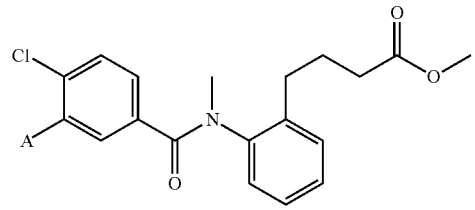

| Ex. | A | MS (M + H)$^+$ | $t_R$ (min) | HPLC Method |
|---|---|---|---|---|
| 13-1 | 6-chloro-4-methyl-pyridin-3-yl | 470.9 | 8.41 | 2 |
| 13-2 | 6-cyano-4-methyl-pyridin-3-yl | 461.9 | 7.95 | 2 |
| 13-3 | 4-cyano-6-trifluoromethyl-pyridin-3-yl | 516.2 | 8.86 | 2 |
| 13-4 | 4-methyl-6-trifluoromethyl-pyridin-3-yl | 504.9 | 8.92 | 2 |

Example 14

4-(2-{[4-Chloro-3-(6-chloro-4-methyl-pyridin-3-yl)-benzoyl]-methyl-amino}-phenyl)-butyric acid

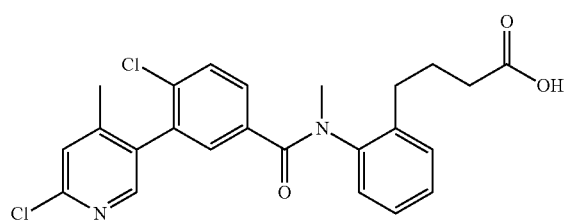 [SMILES: Cc1cc(Cl)ncc1-c1cc(C(=O)N(C)c2ccccc2CCCC(=O)O)ccc1Cl]

Step 14A: 4-(2-{4-Chloro-3-(6-chloro-4-methyl-pyridin-3-yl)-benzol-methyl-amino}-phenyl)-butyric acid 4-(2-{[4-Chloro-3-(6-chloro-4-methyl-pyridin-3-yl)-benzoyl]-methyl-amino}-phenyl)-butyric acid methyl ester 13-1 (9 mg, 0.019 mmol) was dissolved in THF (0.2 mL) and 1M LiOH (0.15 mL) was added. After 1 hour extra 1N LiOH (0.15 mL) was added and the mixture was stirred at room temperature until LCMS indicated that starting material was completely consumed. The mixture was acidified with 1N HCl until pH ~5, MeOH was added and purified by prep LCMS to yield 4-(2-{[4-chloro-3-(6-chloro-4-methyl-pyridin-3-yl)-benzoyl]-methyl-amino}-phenyl)-butyric acid 14-1. MS [M+H]$^+$: 456.9; $t_R$=7.33 min. (method 2)

The following compounds were prepared according to the procedure described above.

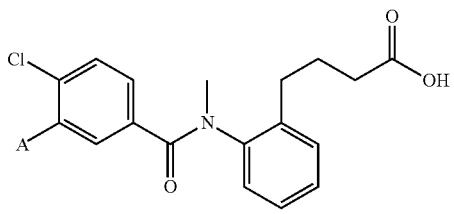

| Ex. | A | MS (M + H)$^+$ | $t_R$ (min) | HPLC Method |
|---|---|---|---|---|
| 14-1 | 6-chloro-4-methyl-pyridin-3-yl | 456.9 | 7.33 | 2 |
| 14-2 | 4-methyl-6-trifluoromethyl-pyridin-3-yl | 491.1 | 7.82 | 2 |
| 14-3 | 6-cyano-4-methyl-pyridin-3-yl | 448.2 | 6.97 | 2 |
| 14-4 | 4-cyano-6-trifluoromethyl-pyridin-3-yl | 502.1 | 7.77 | 2 |

Example 15

4-(2-{[4-Chloro-3-(3-cyano-quinolin-2-yl)-benzoyl]-methyl-amino}-phenyl)-butyric acid

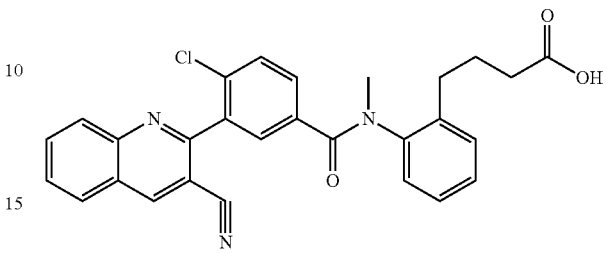

Step 15A: 4-{2-[(3-Bromo-4-chloro-benzoyl)-methyl-amino]-phenyl}-butyric acid To a solution of 4-{2-[(3-bromo-4-chloro-benzoyl)-methyl-amino]-phenyl}-butyric acid methyl ester (1.11 g, 2.6 mmol, Step 13D) in THF (8 mL), 2N LiOH (6.5 mL) was added and the mixture was stirred for 2 hours at rt. 1N HCl was added to the reaction mixture to yield a pH ~2 followed by extraction with EtOAc (2×). The combined organic layers were washed with water and brine, dried (Na$_2$SO$_4$) and concentrated in vacuo to afford 1.1 g of 4-{2-[(3-bromo-4-chloro-benzoyl)-methyl-amino]-phenyl}-butyric acid as a white solid. MS [M+H]$^+$: 411.7; $t_R$=2.57 min, (method 1)

Step 15B: 4-{2-[(3-Bromo-4-chloro-benzoyl)-methyl-amino]-phenyl}-butyric acid tert-butyl ester To a cooled solution (0° C.) of 4-{2-[(3-bromo-4-chloro-benzoyl)-methyl-amino]-phenyl}-butyric acid (1.07 g, 2.60 mmol) in anhydrous DCM (10 mL), oxalyl chloride (0.34 mL, 3.90 mmol) was added dropwise. The mixture was stirred at room temperature for 4 hours, concentrated in vacuo and redissolved in anhydrous dichloromethane (5 mL). A solution of t-butanol (960 mg, 13 mmol) in anhydrous DCM (5 mL) was added and the mixture was stirred at room temperature overnight. After dilution with DCM, the mixture was washed with sat NaHCO$_3$ and brine, dried over Na$_2$SO$_4$, filtered and concentrated. Purification by silica gel column chromatography (EtOAc/Hexanes: 1/4 with gradient up to EtOAc/Hexanes 1/3) afforded 1.1 g of 4-{2-[(3-bromo-4-chloro-benzoyl)-methyl-amino]-phenyl}-butyric acid tert-butyl ester as a colorless oil. MS [M+H]$^+$ (fragment):411.7 (f; $t_R$=3.10 min, (method 1)

Step 15C: 4-(2-{[4-Chloro-3-(4,4,5,5-tetramethyl-[1,3,2]dioxaborolan-2-yl)-benzoyl]-methyl-amino}-phenyl)-butyric acid tert-butyl ester A mixture of 4-{2-[(3-bromo-4-chloro-benzoyl)-methyl-amino]-phenyl}-butyric acid tert-butyl ester (1.0 g, 2.14 mmol), bis(pinacolato)diboron (816 mg, 3.21 mmol), Pd(dppf)$_2$Cl$_2$ (125 mg, 0.1117 mmol) and potassium acetate (629 mg, 6.42 mmol) in dioxane (20 mL) was degassed by bubbling N$_2$ for 5 minutes and then heated under sealed conditions to 95° C. for 14 hrs. Upon cooling to room temperature, the mixture was diluted with ethyl acetate, washed with water and brine and dried over Na$_2$SO$_4$. The filtrate was then concentrated and purified by silica gel column chromatography eluting with ethyl acetate/hexane (1/4) to yield 4-(2-{[4-chloro-3-(4,4,5,5-tetramethyl-[1,3,2]dioxaborolan-2-yl)-benzoyl]-methyl-amino}-phenyl)-butyric acid tert-butyl ester (1.1 g). MS [M+H]$^+$: 514.0; $t_R$=3.24 min (method 1)

Step 15D: 4-(2-{[4-Chloro-3-(3-cyano-quinolin-2-yl)-benzoyl]-methyl-amino}-phenyl)-butyric acid tert-butyl ester A mixture of THF (0.5 mL) and water (0.133 mL) containing 4-(2-{[4-chloro-3-(4,4,5,5-tetramethyl-[1,3,2]dioxaborolan-2-yl)-benzoyl]-methyl-amino}-phenyl)-butyric acid tert-butyl ester (70 mg, 0.14 mmol), 2-chloro-3-methylquinoline (24 mg, 0.125 mmol), Pd$_2$(dba)$_3$ (11 mg, 0.012 mmol), P(t-Bu)$_3$HBF$_4$ (7 mg, 0.024 mmol) and KOH (28 mg, 0.5 mmol), was bubbled with N$_2$ for 5 min and then heated at 70° C. for 6 hrs. The mixture was diluted with EtOAc, washed with water and brine, dried (Na$_2$SO$_4$), filtered and concentrated in vacuo. Purification by silica gel column chromatography (eluent EtOAc/Hexanes:1/4 with gradient up to EtOAc/Hexanes:1/1) yielded 20 mg of 4-(2-{[4-chloro-3-(3-cyano-quinolin-2-yl)-benzoyl]-methyl-amino}-phenyl)-butyric acid tert-butyl ester. MS: 539.9 (M+H)$^+$; $t_R$=2.99 min (method 1).

Step 15E: 4-(2-{[4-Chloro-3-(3-cyano-quinolin-2-yl)-benzoyl]-methyl-amino}-phenyl)-butyric acid 4-(2-{[4-Chloro-3-(3-cyano-quinolin-2-yl)-benzoyl]-methyl-amino}-phenyl)-butyric acid tert-butyl ester (20 mg, 0.037 mmol) was stirred in a mixture of DCM (0.2 mL) and TFA (0.2 mL) for 1 hr. The mixture was concentrated, dissolved in MeOH and purified by prep LCMS to yield 4-(2-{[4-chloro-3-(3-cyano-quinolin-2-yl)-benzoyl]-methyl-amino}-phenyl)-butyric acid 15-1. MS [M+H]$^+$: 483.9; $t_R$=7.05 min, (method 2)

Example 16

3-(2-{[4-Chloro-3-(6-cyano-4-methyl-pyridin-3-yl)-benzoyl]-methyl-amino}-6-methyl-phenoxy)-propionic acid ethyl ester

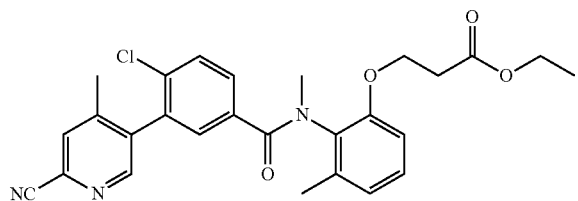 [SMILES: CCOC(=O)CCOc1cccc(C)c1N(C)C(=O)c1ccc(Cl)c(-c2cnc(C#N)cc2C)c1]

Step 16A: 3-(2-{[4-Chloro-3-(6-cyano-4-methyl-pyridin-3-yl)-benzoyl]-methyl-amino}-6-methyl-phenoxy)-propionic acid ethyl ester To a solution of 3-(2-{[4-chloro-3-(6-cyano-4-methyl-pyridin-3-yl)-benzoyl]-methyl-amino}-6-methyl-phenoxy)-propionic acid (160 mg, 0.35 mmol) in DCM (15 mL) was added oxalyl chloride (45.2 µL, 0.52 mmol) and 1 drop of DMF. The solution was stirred for 30 minutes before addition of ethanol (5 mL). The solution was stirred for a further 30 minutes at which time the solvent was evaporated and the residue purified by preparative TLC [eluent: 50% ethyl acetate in hexane] to yield 3-(2-{[4-chloro-3-(6-cyano-4-methyl-pyridin-3-yl)-benzoyl]-methyl-amino}-6-methyl-phenoxy)-propionic acid ethyl ester 16-1 (125 mg). MS [M+H]$^+$: 492.4; $t_R$=5.45 min. (method 4).

Similarly, 3-(2-{[4-chloro-3-(4-cyano-6-trifluoromethyl-pyridin-3-yl)-benzoyl]-methyl-amino}-phenoxy)-propionic acid ethyl ester 16-2 was prepared. MS [M+H]$^+$: 532.2; $t_R$=30.78 min. (method 5).

Example 17

[[4-Chloro-3-(3,5-dichloro-pyridin-2-yl)-benzoyl]-(2-methoxy-phenyl)-amino]-acetic acid methyl ester

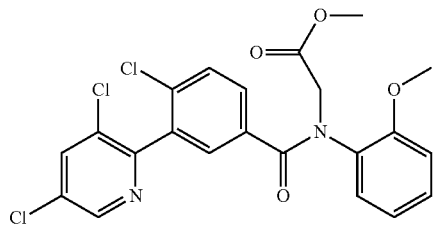 [SMILES: COC(=O)CN(C(=O)c1ccc(Cl)c(-c2ncc(Cl)cc2Cl)c1)c1ccccc1OC]

Step 17A: 4-Chloro-N-(2-methoxy-phenyl)-3-(4,4,5,5-tetramethyl-[1,3,2]dioxaborolan-2-yl)-benzamide A mixture of 3-bromo-4-chloro-N-(2-methoxy-phenyl)-benzamide (2 g, 5.85 mmol, Step 2B), bis(pinacolato)diboron (2.23 g, 8.78 mmol), Pd(dppf)$_2$Cl$_2$ (342 mg, 0.47 mmol), potassium acetate (1.72 g, 17.6 mmol) in dioxane (40 mL) was degassed by bubbling through N$_2$ for 5 minutes and then was heated under sealed condition to 95° C. for 14 hrs. Upon cooling to room temperature, the mix was diluted with ethyl acetate and washed with water and brine, and was dried over Na$_2$SO$_4$. Concentration and purification by silica gel column chromatography eluting with ethyl acetate/hexane (2/3) gave 4-chloro-N-(2-methoxy-phenyl)-3-(4,4,5,5-tetramethyl-[1,3,2]dioxaborolan-2-yl)-benzamide (2.3 g). MS [M+H]$^+$: 387.8; $t_R$=3.15 min. (method 1)

Step 17B: 4-Chloro-3-(3,5-dichloro-pyridin-2-yl)-N-(2-methoxy-phenyl)-benzamide

A solution of 2N Na$_2$CO$_3$ (5.85 mL) and Pd(PPh$_3$)$_4$ (340 mg, 0.29 mmol) was added to a degassed mixture of 4-chloro-N-(2-methoxy-phenyl)-3-(4,4,5,5-tetramethyl-[1,3,2]dioxaborolan-2-yl)-benzamide (2.2 g, 5.85 mmol) and 2-bromo-3,5-dichloro-pyridine (1.47 g, 6.44 mmol) in toluene (30 mL) and EtOH (6 mL). The mixture was heated at 100° C. for 12 hrs. Upon cooling to room temperature, the mixture was diluted with ethyl acetate and washed with water and brine, and was dried over Na$_2$SO$_4$. After filtration and concentration the mixture was taken up in EtOAc, filtered, washed with EtOAc (3×), MeOH and ether to yield 1.6 g of 4-chloro-3-(3,5-dichloro-pyridin-2-yl)-N-(2-methoxy-phenyl)-benzamide. MS [M+H]$^+$: 406.9; $t_R$=3.03 min. (method 1)

Step 17C: [[4-Chloro-3-(3,5-dichloro-pyridin-2-yl)-benzoyl]-(2-methoxy-phenyl)-amino]-acetic acid methyl ester To 4-chloro-3-(3,5-dichloro-pyridin-2-yl)-N-(2-methoxy-phenyl)-benzamide (40 mg, 0.1 mmol) in DMF (0.6 mL) at 0-5° C., NaH (8 mg, 0.2 mmol, 60% in mineral oil) was added and the mixture was stirred for 25 min at rt. Upon addition of bromomethylacetate (21 μL, 0.2 mmol), the mixture was stirred at room temperature for 12 hrs. Addition of MeOH (0.3 mL) was followed by filtration and purification on preparative HPLC to afford [[4-chloro-3-(3,5-dichloro-pyridin-2-yl)-benzoyl]-(2-methoxy-phenyl)-amino]-acetic acid methyl ester 17-1.

The following compounds were prepared according to the procedure described above.

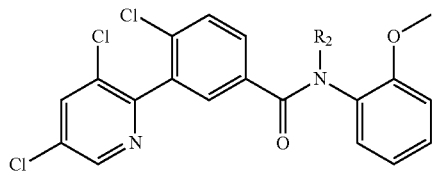

| Ex. | R₂ | MS (M + H)⁺ | $t_R$ (min) method 2 |
| --- | --- | --- | --- |
| 17-1 | acetic acid methyl ester | 478.6 | 9.92 |
| 17-2 | ethyl | 434.7 | 8.73 |
| 17-3 | 4-butyric acid methyl ester | 506.7 | 8.68 |

Example 18

4-Chloro-N-cyclopropyl-3-(3,5-dichloro-pyridin-2-yl)-N-(2-methoxy-phenyl)-benzamide

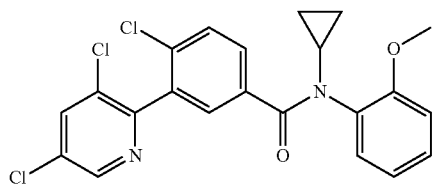 [SMILES: COc1ccccc1N(C(=O)c1ccc(Cl)c(-c2ncc(Cl)cc2Cl)c1)C1CC1]

Step 18A: 3-Bromo-4-chloro-benzoic acid methyl ester

To a suspension of 3-bromo-4-chloro-benzoic acid (10 g, 42.6 mmol) in MeOH (100 mL) cooled with ice bath, was added acetyl chloride (30.4 mL, 0.43 mol) dropwise. The mixture was then stirred at room temperature for 12 hrs and concentrated to yield 3-bromo-4-chloro-benzoic acid methyl ester as a yellow solid (10.6 g). NMR (CDCl₃), δ, 8.28 (1H, s), 7.91 (1H, brs), 7.52 (1H, brs), 3.92 (3H, s).

Step 18B: 4-Chloro-3-(4,4,5,5-tetramethyl-[1,3,2]dioxaborolan-2-yl)-benzoic acid methyl ester A mixture of 3-bromo-4-chloro-benzoic acid methyl ester (3.13 g, 12.6 mmol), bis(pinacolato)diboron (4.79 g, 18.8 mmol), PdCl₂(dppf)₂ (0.74 g, 1.0 mmol), KOAc (3.69 g, 37.7 mmol) in DMF (50 mL) was sealed and heated at 95° C. for 12 hrs. The mixture was partitioned between ethyl acetate and water. Organic layer was separated, washed with water, brine, dried over MgSO₄. After filtration and concentration, purification by silica gel chromatography eluting with ethyl acetate/hexane (1/9) gave 4-chloro-3-(4,4,5,5-tetramethyl-[1,3,2]dioxaborolan-2-yl)-benzoic acid methyl ester (3.5 g). NMR (DMSO-d₆), δ, 8.19 (1H, d, J=2.1 Hz), 7.99 (1H, dd, J=2.1, 8.4 Hz), 7.58 (1H, d, J=8.4 Hz), 3.85 (3H, s), 1.31 (12H, s).

Step 18C: 4-Chloro-3-(3,5-dichloro-pyridin-2-yl)-benzoic acid methyl ester

A mixture of 2-bromo-3,5-dichloropyridine (2.72 g, 12 mmol), 4-chloro-3-(4,4,5,5-tetramethyl-[1,3,2]dioxaborolan-2-yl)-benzoic acid methyl ester (1.78 g, 6 mmol)), 2N Na₂CO₃ (9.0 mL, 18 mmol), Pd(PPh₃)₄ (0.35 g, 0.3 mmol) in toluene/ethanol (30 mL/6 mL) was sealed and heated at 90° C. for 12 hrs. The mixture was concentrated and partitioned between ethyl acetate and water. The ethyl acetate layer was washed with water and brine and was dried over MgSO₄. After filtration and concentration, purification by silica gel chromatography eluting with ethyl acetate/hexane (5/95) gave 4-chloro-3-(3,5-dichloro-pyridin-2-yl)-benzoic acid methyl ester (1.8 g). MS (M+H)⁺: 315.6, $t_R$=8.505 min (method 2)

Step 18D: 4-Chloro-3-(3,5-dichloro-pyridin-2-yl)-benzoic acid

A mixture of THF (15 mL) and water (1 mL) containing 4-chloro-3-(3,5-dichloro-pyridin-2-yl)-benzoic acid methyl ester (1.7 g, 5.4 mmol) and LiOH.H₂O (0.68 g, 16.1 mmol) was stirred at room temperature for 12 hrs. The mixture was acidified and extracted with ethyl acetate. The organic layer was washed with brine and water and was dried. Filtration and concentration gave 4-chloro-3-(3,5-dichloro-pyridin-2-yl)-benzoic acid as a white solid (1.4 g). MS (M+H)⁺: 301.6, $t_R$=7.048 min (method 2)

Step 18E: Cyclopropyl-(2-methoxy-phenyl)-amine

To a mixture of 2-methoxyaniline (3 g, 24.3 mmol), HOAc (100 mL) and MeOH (50 mL), [(1-ethoxycyclopropyl)oxy]-trimethylsilane (5.6 mL, 28.0 mmol) was added dropwise at r.t. The mixture was refluxed at 65° C. for 3 hrs and subsequently concentrated in vacuo.

A mixture of NaBH₄ (1.84 g, 48.6 mmol) in anhydrous THF (25 mL) was cooled to 5° C. and BF₃.Et₂O (6.1 mL, 50 mmol) was added dropwise under N₂ atmosphere. The mixture was stirred for 1 hr at 5° C., then the crude oil from the previous step dissolved in THF (12 mL) was added dropwise at 5-10° C. in a time period of 20 min. The mixture was stirred at rt overnight and at reflux for 2 hrs, quenched in water (100 mL) and extracted with ether (3×). The combined organic layers were washed with water, dried (Na₂SO₄), filtered and concentrated to yield 4.1 g of cyclopropyl-(2-methoxy-phenyl)-amine as an oil which was used without further purification. MS [M+H]⁺: 164.0; $t_R$=2.46 min. (method 1)

Step 18F: 4-Chloro-N-cyclopropyl-3-(3,5-dichloro-pyridin-yl)-N-(2-methoxy-phenyl)-benzamide To 4-chloro-3-(3,5-dichloro-pyridin-2-yl)-benzoic acid (60 mg, 0.2 mmol) in dry DCM (0.6 mL) was added DMF (1 drop) followed by slow addition of oxalyl chloride (30 μL, 0.34 mmol). The mixture was stirred for 2.5 hrs, then concentrated to yield the corresponding 4-chloro-3-(3,5-dichloro-pyridin-2-yl)-benzoyl chloride which was dissolved in DCM (1 mL). Cyclopropyl-(2-methoxy-phenyl)-amine (55 mg, 0.34 mmol), followed by diisopropylethylamine (71 μL, 0.4 mmol) were added slowly. The mixture was stirred at room temperature for 12 hrs, concentrated and purified by preparative LCMS to yield 4-chloro-N-cyclopropyl-3-(3,5-dichloro-pyridin-2-yl)-N-(2-methoxy-phenyl)-benzamide 18-1. MS (M+H)$^+$: 446.9, $t_R$=8.59 min (method 2)

Example 19

4-Chloro-3-(3,5-dichloro-pyridin-2-yl)-N-(2-hydroxy-phenyl)-N-methyl-benzamide

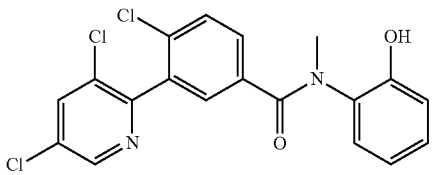 [SMILES: CN(C(=O)c1ccc(Cl)c(-c2ncc(Cl)cc2Cl)c1)c1ccccc1O]

Step 19A: 4-Chloro-3-(3,5-dichloro-pyridin-2-yl)-N-(2-hydroxy-phenyl)-N-methyl-benzamide To 4-chloro-3-(3,5-dichloro-pyridin-2-yl)-benzoic acid (100 mg, 0.33 mmol) in dry DCM (1 mL), was added DMF (1 drop) followed by addition of oxalyl chloride (35 μL, 0.40 mmol) slowly. The mixture was stirred for 2.5 hrs, then concentrated to yield 4-chloro-3-(3,5-dichloro-pyridin-2-yl)-benzoyl chloride, which was dissolved in DCM (1 mL). 2-Methylamino-phenol (45 mg, 0.36 mmol) was added followed by the slow addition of diisopropylethylamine (88 μL, 0.5 mmol). The mixture was stirred at room temperature for 12 hrs, concentrated and purified by preparative TLC (DCM/MeOH=9/1) followed by preparative LCMS to yield 4-chloro-3-(3,5-dichloro-pyridin-2-yl)-N-(2-hydroxy-phenyl)-N-methyl-benzamide 19-1. MS (M+H)$^+$: 409.0, $t_R$=7.55 min (method 2)

The following compounds were prepared according to the procedure described above.

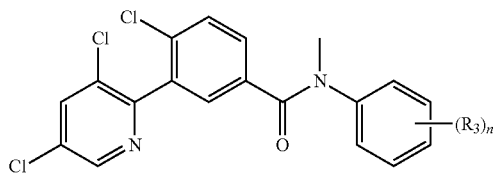

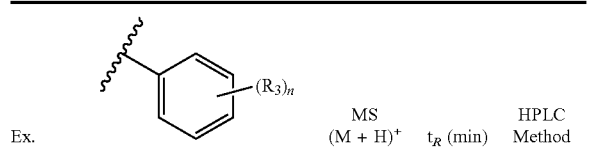

| Ex. | | MS (M + H)$^+$ | $t_R$ (min) | HPLC Method |
|---|---|---|---|---|
| 19-1 | 2-hydroxy-phenyl | 409.0 | 7.55 | 2 |
| 19-2 | 2-methoxy-phenyl | 420.8 | 8.29 | 2 |
| 19-3 | 3-fluoro-phenyl | 410.7 | 8.40 | 2 |
| 19-4 | 4-fluoro-phenyl | 409.6 | 8.34 | 2 |
| 19-5 | phenyl | 390.7 | 8.22 | 2 |
| 19-6 | 2-benzoic acid methyl ester | 448.6 | 8.06 | 2 |
| 19-7 | 3-chloro-2-methoxy-phenyl | 456.6 | 8.78 | 2 |
| 19-8 | 2,6-dimethyl-phenyl | 418.7 | 8.90 | 2 |
| 19-9 | 3-methoxy-phenyl | 420.7 | 8.21 | 2 |
| 19-10 | 2,3-dimethyl-phenyl | 418.7 | 8.90 | 2 |

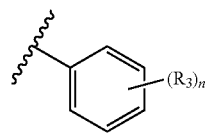

Example 20

4-[5-Chloro-4-(4-cyano-6-trifluoromethyl-pyridin-3-yl)-2-(methyl-o-tolyl-carbamoyl)-phenoxy]-butyric acid

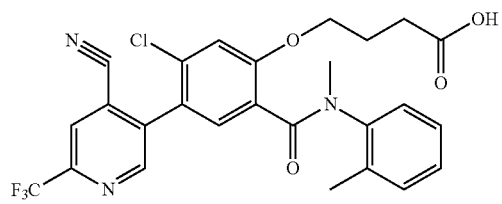 [SMILES: Cc1ccccc1N(C)C(=O)c1cc(-c2cnc(C(F)(F)F)cc2C#N)c(Cl)cc1OCCCC(=O)O]

Step 20A: 4-Chloro-2-fluoro-3-nitro-benzoyl chloride

To 4-chloro-2-fluoro-3-nitro-benzoic acid (5.0 g, 22.8 mmol) suspended in dry DCM (60 mL), was added DMF (0.5 mL) followed by the slow addition of oxalyl chloride (2.4 mL, 27.3 mmol, 2M in DCM). The mixture was stirred for 2 hrs, then concentrated to yield 4-chloro-2-fluoro-3-nitro-benzoyl chloride as a yellow solid.

Step 20B: 4-Chloro-2-fluoro-N-methyl-5-nitro-N-o-tolyl-benzamide

To 4-chloro-2-fluoro-3-nitro-benzoyl chloride in DCM (60 mL) cooled with a ice bath, triethylamine (6.3 mol, 45.5 mmol) was added slowly, followed by the dropwise addition of N-methyl-o-toluidine (3.8 mL, 27.3 mmol). The ice bath was removed and the mixture was stirred for 12 hrs, followed by partition between DCM and water. The organic layer was then washed with 1 N HCl, saturated NaHCO$_3$ and brine and was dried over MgSO$_4$. Concentration yielded 4-chloro-2-fluoro-N-methyl-5-nitro-N-o-tolyl-benzamide as a yellow solid (6.6 g). MS: 322.8 (M+H)$^+$: $t_R$=2.42 min (method 1);

Step 20C: 5-Amino-4-chloro-2-fluoro-N-methyl-N-o-tolyl-benzamide

To 4-chloro-2-fluoro-N-methyl-5-nitro-N-o-tolyl-benzamide (6.6 g, 20.3 mmol) was stirred vigorously in a mixture of water (30 mL) and THF (30 mL) containing Na$_2$S$_2$O$_4$ (17.6 g, 101.2 mmol) for 12 hrs. The organic layer was then separated and the water layer was further extracted with ethyl acetate. The combined organic solutions were washed with brine and dried over MgSO$_4$. Concentration yielded 5-amino-4-chloro-2-fluoro-N-methyl-N-o-tolyl-benzamide as a crude solid which was washed with ether to give a light yellow product (3.3 g). MS: 292.9 (M+H)$^+$; $t_R$=1.90 min (method 1)

Step 20D: 5-Bromo-4-chloro-2-fluoro-N-methyl-N-o-tolyl-benzamide

To a solution of acetonitrile (45.0 mL) containing CuBr$_2$ (3.2 g, 14.3 mmol) and n-butylnitrite (1.7 mL, 14.3 mmol) heated at 65° C. with stirring, was added 5-amino-4-chloro-2-fluoro-N-methyl-N-o-tolyl-benzamide (3.2 g, 11.0 mmol) in acetonitrile (10.0 mL) dropwise. After 2 hours the mixture was cooled to room temperature and was partitioned between ethyl acetate and water. The organic layer was separated, washed with 1N HCl, sat. NaHCO$_3$ and brine, dried over MgSO$_4$ and filtered. Concentration gave an oil which was purified by silica gel column chromatography eluting with ethyl acetate in hexanes (1/5) to give 5-bromo-4-chloro-2-fluoro-N-methyl-N-o-tolyl-benzamide as a light yellow oil (3.1 g). MS: 355.8 (M+H)$^+$; $t_R$=2.61 min (method 1)

Step 20E: 5-Bromo-4-chloro-2-methoxy-N-methyl-N-o-tolyl-benzamide

A mixture of 5-bromo-4-chloro-2-fluoro-N-methyl-N-o-tolyl-benzamide (2.5 g, 7.0 mmol) was heated in MeONa/MeOH (20 mL, 25%) at 55° C. for 12 hrs, then was concentrated and partitioned between DCM and water. The organic layer was then separated, washed with 3N HCl, sat NaHCO$_3$ and brine, dried over MgSO$_4$, and concentrated. Purification by silica gel column chromatography eluting with ethyl acetate in hexanes (1/4) gave 5-bromo-4-chloro-2-methoxy-N-methyl-N-o-tolyl-benzamide (2.75 g). MS: 367.8 (M+H)$^+$; $t_R$=2.51 min (method 1).

Step 20F: 5-Bromo-4-chloro-2-hydroxy-N-methyl-N-o-tolyl-benzamide

To a solution of DCM (15.0 mL) containing 5-bromo-4-chloro-2-methoxy-N-methyl-N-o-tolyl-benzamide (2.75 g, 7.5 mmol) at −78° C., was added BBr$_3$ (38.0 mL, 1M in DCM) dropwise. The mixture was gradually warmed to room temperature and stirred for 12 hrs. The mixture was concentrated to yield a solid which was washed by ether to give 5-bromo-4-chloro-2-hydroxy-N-methyl-N-o-tolyl-benzamide (2.6 g). MS: 353.8 (M+H)$^+$; $t_R$=2.50 min (method 1).

Step 20G: 4-[4-Bromo-5-chloro-2-(methyl-o-tolyl-carbamoyl)-phenoxy]-butyric acid tert-butyl ester To 5-bromo-4-chloro-2-hydroxy-N-methyl-N-o-tolyl-benzamide (2.6 g, 7.3 mmol) in dry DMF (30 mL), was added K$_2$CO$_3$ (2.0 g, 7.6 mmol), followed by addition of t-butyl 4-bromobutyrate (2.0 g, 8.8 mmol). The mixture was heated at 60° C. for 12 hrs and partitioned between ethyl acetate and water. The organic layer was separated, washed with water and brine, and dried over MgSO$_4$. After filtration, concentration and purification by silica gel column chromatography eluting with ethyl acetate in hexanes (3/7) gave 4-[4-bromo-5-chloro-2-(methyl-o-tolyl-carbamoyl)-phenoxy]-butyric acid tert-butyl ester (3.0 g). MS: 496.3 (M+H)$^+$; $t_R$=2.81 min (method 1).

Step 20H: 4-[5-chloro-2-(methyl-o-tolyl-carbamoyl)-4-(4,4,5-tetramethyl-[1,3,2]dioxaborolan-2-yl)-phenoxy]-butyric acid tert-butyl ester A mixture of 4-[4-bromo-5-chloro-2-(methyl-o-tolyl-carbamoyl)-phenoxy]-butyric acid tert-butyl ester (3.0 g, 6.1 mmol), bis(pinacolato)diboron (2.3 g, 9.1 mmol), PdCl$_2$(dppf)$_2$ (354.0 mg, 0.48 mmol) and potassium acetate (1.78 g, 18.2 mmol) in dioxane (30 mL) was sealed after degassed with N$_2$ for 5 min, and heated at 95° C. for 12 hrs. The mixture was filtered through celite to remove solids. The celite was washed by ethyl acetate several times. The combined solution was washed with water and brine, dried over MgSO$_4$ and filtered. Concentration and purification by silica gel column chromatography eluting with ethyl acetate in hexanes (1/5) gave 4-[5-chloro-2-(methyl-o-tolyl-carbamoyl)-4-(4,4,5,5-tetramethyl-[1,3,2]dioxaborolan-2-yl)-phenoxy]-butyric acid tert-butyl ester (3.0 g). MS: 544.0 (M+H)$^+$; $t_R$=2.90 min (method 1).

Step 20I: 4-[5-chloro-4-(4-cyano-6-trifluoromethyl-pyridin-3-yl)-2-(methyl-o-tolyl-carbamoyl)-phenoxy]-butyric acid tert-butyl ester 4-[5-Chloro-2-(methyl-o-tolyl-carbamoyl)-4-(4,4,5,5-tetramethyl-[1,3,2]dioxaborolan-2-yl)-phenoxy]-butyric acid tert-butyl ester (444.0 mg, 0.8 mmol), 5-bromo-2-trifluoromethyl-isonicotinonitrile (171.0 mg, 0.7 mmol), Pd(Ph$_3$P)$_4$ (78.6 mg, 0.07 mmol), Na$_2$CO$_3$ (432.0 mg, 4.1 mmol) in dioxane (9 mL) and water (1 mL) was degassed with N$_2$ for 5 min, sealed, and heated at 100° C. for 12 hrs. The mixture was then partitioned between ethyl acetate and water. The organic layer was washed with water and brine, dried over MgSO$_4$ and filtered. Concentration and purification by TLC plates eluting with ethyl acetate in hexanes (2/3) and again with TLC plates eluting with acetonitrile/dichloromethane (1/9) gave 4-[5-chloro-4-(4-cyano-6-trifluoromethyl-pyridin-3-yl)-2-(methyl-o-tolyl-carbamoyl)-phenoxy]-butyric acid tert-butyl ester (410 mg). MS: 588.7 (M+H)$^+$; $t_R$=11.05 min (method 3).

Step 20J: 4-[5-Chloro-4-(4-cyano-6-trifluoromethyl-pyridin-3-yl)-2-(methyl-o-tolyl-carbamoyl)-phenoxy]-butyric acid 4-[5-chloro-4-(4-cyano-6-trifluoromethyl-pyridin-3-yl)-2-(methyl-o-tolyl-carbamoyl)-phenoxy]-butyric acid tert-butyl ester (410 mg, 0.7 mmol) was stirred in a mixture of trifluoroacetic acid in DCM (1/1, 3 mL) for 2 hrs. Concentration followed by purification by HPLC gave 4-[5-chloro-4-(4-cyano-6-trifluoromethyl-pyridin-3-yl)-2-(methyl-o-tolyl-carbamoyl)-phenoxy]-butyric acid 20-1 (62 mg). MS: 532.6 (M+H)$^+$; $t_R$=5.29 min (method 3). NMR (CDCl$_3$, reported as the major isomer of cis-trans amide rotamers), δ, 8.54 (1H, s), 7.94 (1H, s), 7.34-7.25 (1H, m), 7.18-7.14 (2H, m), 7.14-7.04 (1H, m), 7.02 (1H, s), 6.92 (1H, s), 4.08 (2H, t, J=6.3 Hz), 3.40 (3H, s), 2.62 (2H, t, J=6.3 Hz), 2.30-2.18 (2H, m), 2.57 (3H, s).

The following compounds were similarly prepared to Example 20-1:

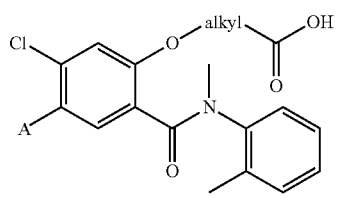

| Ex. | A | alkyl | MS (M + H)$^+$ | $t_R$ (min) | HPLC Method |
|---|---|---|---|---|---|
| 20-1 | 4-cyano-6-trifluoromethyl-pyridin-3-yl | —(CH$_2$)$_3$— | 532.6 | 5.29 | 3 |
| 20-2 | 4,6-dichloro-pyridin-3-yl | —(CH$_2$)$_3$— | 506.8 | 4.95 | 2 |
| 20-3 | 3-cyano-quinolin-2-yl | —(CH$_2$)$_3$— | 513.9 | 4.60 | 2 |

Example 21-1

4-Chloro-5-(4-cyano-6-trifluoromethyl-pyridin-3-yl)-2-(4-hydroxy-butoxy)-N-(2-methoxy-6-methyl-phenyl)-N-methyl-benzamide

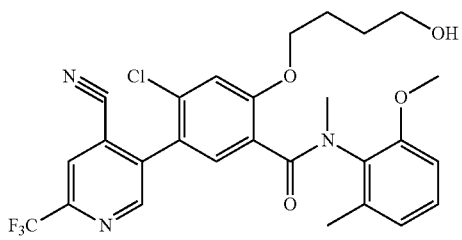 [SMILES: COc1cccc(C)c1N(C)C(=O)c1cc(-c2cnc(C(F)(F)F)cc2C#N)c(Cl)cc1OCCCCO]

Step 21A: 5-Amino-4-chloro-2-fluoro-benzoic acid methyl ester

SOCl$_2$ (10.0 mL, 137.0 mmol) was added slowly to an ice bath cooled mixture of 4-chloro-2-fluoro-3-nitro-benzoic acid (25.0 g, 114.2 mmol) in MeOH (200 mL). The mixture was heated at 70° C. for 16 hrs then concentrated to yield 4-chloro-2-fluoro-5-nitro-benzoic acid methyl ester (24.9 g, 0.11 mmol), which was resuspended in a mixture of THF (200 mL) and water (200 mL). Na$_2$S$_2$O$_4$ (139.4 g, 0.80 mol) was added with vigorous stirring. After stirring for 2 hours, the mixture was extracted with ethyl acetate and the organic layer was washed with water and dried over Na$_2$SO$_4$. The filtrate was concentrated to give 5-amino-4-chloro-2-fluoro-benzoic acid methyl ester (15.1 g). MS: 203.9 (M+H)$^+$; $t_R$=1.67 min (method 1).

Step 21B: 5-Bromo-4-chloro-2-fluoro-benzoic acid methyl ester

Isoamyl nitrite (12.7 mL, 94.8 mmol) was added to 5-amino-4-chloro-2-fluoro-benzoic acid methyl ester (14.8 g, 72.9 mmol) in acetonitrile (280 mL), followed by addition of CuBr$_2$ (21.1 g, 94.8 mmol). Then the mixture was heated at 65° C. with stirring for 2 hrs, followed by partition between ethyl acetate and water. The organic layer was then washed with saturated NaHCO$_3$ and brine and was dried over Na$_2$SO$_4$. The filtrate was concentrated and purified by silica gel chromatography eluting with ethyl acetate/hexane (1/1) to yield 5-bromo-4-chloro-2-fluoro-benzoic acid methyl ester (14.0 g). MS: 268.0 (M$^+$) from GC-MS; $t_R$=2.53 min (method 1);

Step 21C: 5-Bromo-4-chloro-2-fluoro-benzoic acid

5-Bromo-4-chloro-2-fluoro-benzoic acid methyl ester (14.0 g, 52.4 mmol) was stirred vigorously in a mixture of THF (250 ml) and 1N NaOH (200 ml) for 16 hrs. The mixture was acidified to pH 3 with 6N HCl, concentrated partially to remove THF and then extracted with ethyl acetate. The organic phase was washed with water and brine and was dried over Na$_2$SO$_4$. The filtrate was concentrated to yield 5-bromo-4-chloro-2-fluoro-benzoic acid (13.3 g).

Step 21D: 5-Bromo-4-chloro-2-fluoro-benzoyl chloride

5-Bromo-4-chloro-2-fluoro-benzoic acid (13.3 g, 52.6 mmol) was converted to 5-bromo-4-chloro-2-fluoro-benzoyl chloride (14.0 g) using the procedure of Step 2A.

Step 21E: 5-Bromo-4-chloro-2-fluoro-N-(2-methoxy-6-methyl-phenyl)-benzamide

5-Bromo-4-chloro-2-fluoro-N-(2-methoxy-6-methyl-phenyl)-benzamide (9.1 g) as a white solid was obtained from the corresponding 5-bromo-4-chloro-2-fluoro-benzoyl chloride (7.0 g, 25.8 mmol) using the procedure of Step 2B. MS: 373.8 (M+H)$^+$, $t_R$=2.54 min (method 1).

Step 21F: 5-Bromo-4-chloro-2-fluoro-N-(2-methoxy-6-methyl-phenyl)-N-methyl benzamide 5-Bromo-4-chloro-2-fluoro-N-(2-methoxy-6-methyl-phenyl)-N-methyl-benzamide (9.0 g) was obtained from the corresponding 5-bromo-4-chloro-2-fluoro-N-(2-methoxy-6-methyl-phenyl)-benzamide (9.1 g, 24.5 mmol) using the procedure of Step 2C. MS: 387.8 (M+H)$^+$, $t_R$=2.60 min (method 1).

Step 21G: 5-bromo-4-chloro-2-(4-hydroxy-butoxy)-N-(2-methoxy-6-methyl-phenyl)-N-methyl-benzamide NaH (373 mg, 9.3 mmol, 60% in mineral oil) was added to 1,4-butanediol (3.5 g, 38.9 mmol) in dry DMF (50 mL). The mixture was stirred at room temperature for 15 minutes. 5-Bromo-4-chloro-2-fluoro-N-(2-methoxy-6-methyl-phenyl)-benzamide (3.0 g, 7.8 mmol) in DMF (25 mL) was added slowly. The mixture was then heated at 50° C. for 2 hrs, cooled to room temperature and partitioned between DCM and water. The organic layer was separated, washed with 1H HCl, sat NaHCO$_3$ and brine, then dried over Na$_2$SO$_4$. The filtrate was concentrated and the residue purified using column chromatography with a gradient of 50% ethyl acetate in hexanes to 100% ethyl acetate to yield 5-bromo-4-chloro-2-(4-hydroxy-butoxy)-N-(2-methoxy-6-methyl-phenyl)-N-methyl-benzamide (2.3 g). MS: 457.9 (M+H)$^+$, $t_R$=2.38 min (method 1).

Step 21H: 4-Chloro-2-(4-hydroxy-butoxy)-N-(2-meth (4,4,5,5-tetramethyl-[1,3,2]dioxaborolan-2-yl)-benzamide 4-Chloro-2-(4-hydroxy-butoxy)-N-(2-methyl-phenyl)-methyl-5-(4,4,5,5-tetramethyl-[1,3,2]dioxaborolan-2-yl)-benzamide (2.0 g) was obtained from the corresponding 5-bromo-4-chloro-2-(4-hydroxy-butoxy)-N-(2-methoxy-6-methyl-phenyl)-N-methyl-benzamide (2.3 g, 5.0 mmol) using the procedure of Step 2D. MS: 504.1 (M+H)$^+$, $t_R$=2.54 min (method 1).

Step 21I: 4-Chloro-5-(4-cyano-6-trifluoromethyl-pyridin-3-yl)-2-(4-hydroxy-butoxy)-N-(2-methoxy-6-methyl-phenyl)-N-methyl-benzamide 4-Chloro-5-(4-cyano-6-trifluoromethyl-pyridin-3-yl)-2-(4-hydroxy-butoxy)-N-(2-methoxy-6-methyl-phenyl)-N-methyl-benzamide 21-1 was obtained from 4-chloro-2-(4-hydroxy-butoxy)-N-(2-methoxy-6-methyl-phenyl)-N-methyl-5-(4, 4,5,5-tetramethyl-[1,3,2]dioxaborolan-2-yl)-benzamide using the Suzuki procedure of Step 2E1. MS: 548.0 (M+H)$^+$, $t_R$=2.46 min (method 1).

The following examples were prepared according to the above procedure.

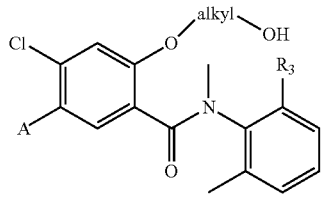

Example 22

4-{5-Chloro-4-(4-cyano-6-trifluoromethyl-pyridin-3-yl)-2-[(2-methoxy-6-methyl-phenyl)-methyl-carbamoyl]-phenoxy}-butyric acid

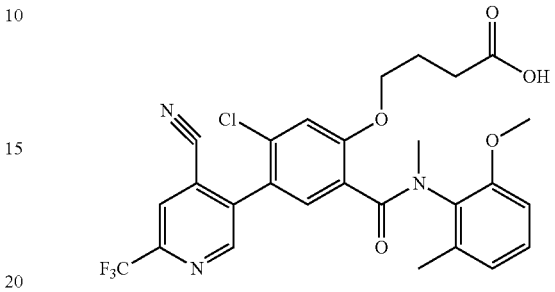

Step 22A: 4-{5-Chloro-4-(4-cyano-6-trifluoromethyl-pyridin-3-yl)-2-[(2-methoxy-6-methyl-phenyl)methyl-carbamoyl]-phenoxy}-butyric acid 4-{5-Chloro-4-(4-cyano-6-trifluoromethyl-pyridin-3-yl)-2-[(2-methoxy-6-methyl-phenyl)methyl-carbamoyl]-phenoxy}-butyric acid (12.6 mg) was obtained from oxidation of 4-chloro-5-(4-cyano-6-trifluoromethyl-pyridin-3-yl)-2-(4-hydroxy-butoxy)-N-(2-methoxy-6-methyl-phenyl)-N-methyl-benzamide 22-1 (40.0 mg, 0.07 mmol) according to the procedure provided in Step 11A. MS: 561.9 (M+H)$^+$, $t_R$=7.84 min (method 2).

The following examples were prepared according to the above procedure.

| Ex. | A | R$_3$ | alkyl | MS (M + H)$^+$ | $t_R$ (min) | HPLC Method |
|---|---|---|---|---|---|---|
| 21-1 | 4-cyano-6-trifluoromethyl-pyridin-3-yl | methoxy | —(CH$_2$)$_4$— | 548.0 | 5.95 | 4 |
| 21-2 | 6-cyano-4-methyl-pyridin-3-yl | methoxy | —(CH$_2$)$_4$— | 493.9 | 7.08 | 2 |
| 21-3 | 3-cyano-quinolin-2-yl | methoxy | —(CH$_2$)$_4$— | 529.9 | 7.33 | 2 |
| 21-4 | 4-cyano-6-trifluoromethyl-pyridin-3-yl | methyl | —(CH$_2$)$_4$— | 532.2 | 5.78 | 4 |
| 21-5 | 6-cyano-4-methyl-pyridin-3-yl | methyl | —(CH$_2$)$_4$— | 478.2 | 5.38 | 4 |
| 21-6 | 3-cyano-quinolin-2-yl | methyl | —(CH$_2$)$_4$— | 514.2 | 5.54 | 4 |
| 21-7 | 4-cyano-6-trifluoromethyl-pyridin-3-yl | methoxy | —(CH$_2$)$_2$— | 520.1 | 4.11 | 4 |
| 21-8 | 4-cyano-6-trifluoromethyl-pyridin-3-yl | methoxy | —(CH$_2$)$_3$— | 534.1 | 7.62 | 2 |

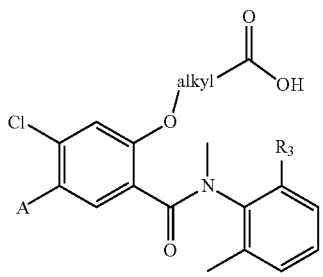

| Ex. | A | R₃ | alkyl | MS (M + H)⁺ | $t_R$ (min) | HPLC Method |
|---|---|---|---|---|---|---|
| 22-1 | 4-cyano-6-trifluoromethyl-pyridin-3-yl | methoxy | —(CH₂)₃— | 561.9 | 7.84 | 2 |
| 22-2 | 6-cyano-4-methyl-pyridin-3-yl | methoxy | —(CH₂)₃— | 507.9 | 7.17 | 2 |
| 22-3 | 3-cyano-quinolin-2-yl | methoxy | —(CH₂)₃— | 543.9 | 7.41 | 2 |
| 22-4 | 4-cyano-6-trifluoromethyl-pyridin-3-yl | methyl | —(CH₂)₃— | 546.1 | 4.73 | 4 |
| 22-5 | 6-cyano-4-methyl-pyridin-3-yl | methyl | —(CH₂)₃— | 492.2 | 3.93 | 4 |
| 22-6 | 3-cyano-quinolin-2-yl | methyl | —(CH₂)₃— | 528.2 | 4.42 | 4 |
| 22-7 | 4-cyano-6-trifluoromethyl-pyridin-3-yl | methyl | —(CH₂)₃— | 546.1 | 4.73 | 4 |
| 22-8 | 6-cyano-4-methyl-pyridin-3-yl | methyl | —(CH₂)₃— | 492.2 | 3.93 | 4 |
| 22-9 | 4-cyano-6-trifluoromethyl-pyridin-3-yl | methoxy | —CH₂— | 533.9 | 4.95 | 4 |
| 22-10 | 4-cyano-6-trifluoromethyl-pyridin-3-yl | methoxy | —(CH₂)₂— | 548.1 | 2.66 | 2 |

4-(4-cyano-6-trifluoromethyl-pyridin-3-yl)-2-[(2-methoxy-6-methyl-phenyl)methyl-carbamoyl]-phenoxy}-butyric acid 22-1 (80 mg, 0.157 mmol) in dioxane (2 mL). The mixture was heated at 100° C. for 16 hrs, then cooled to room temperature and stirred with 6N HCl (1 mL) for 1 hr. The DCM layer was separated, concentrated and the residue was dissolved in MeOH and purified by HPLC-MS to afford 2-(3-amino-propoxy)-4-chloro-5-(4-cyano-6-trifluoromethyl-pyridin-3-yl)-N-(2-methoxy-6-methyl-phenyl)-N-methyl-benzamide 23-1 as a TFA salt (40 mg). MS: 533.0 (M+H)⁺, $t_R$=5.38 min (method 4).

Example 23

2-(3-Amino-propoxy)-4-chloro-5-(4-cyano-6-trifluoromethyl-pyridin-3-yl)-N-(2-methoxy-6-methyl-phenyl)-N-methyl-benzamide

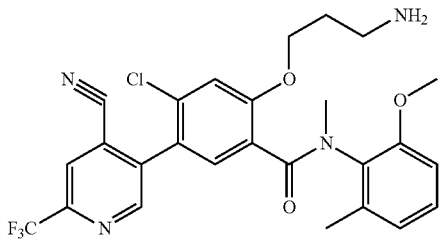 [SMILES: COc1cccc(C)c1N(C)C(=O)c1cc(-c2cnc(C(F)(F)F)cc2C#N)c(Cl)cc1OCCCN]

Step 23A: 2-(3-Amino-propoxy)-4-chloro-5-(4-cyano-6-trifluoromethyl-pyridin-3-yl)-N-(2-methoxy-6-methyl-phenyl)-N-methyl-benzamide Triethylamine (22 μL, 0.157 mmol) and diphosphorylazide (33.90 μL, 0.157 mmol) were added to 4-{5-chloro-

Example 24

5-{2-Chloro-5-[(2-methoxy-phenyl)-methyl-carbamoyl]-phenyl}-pyridine-2-carboxylic acid amide

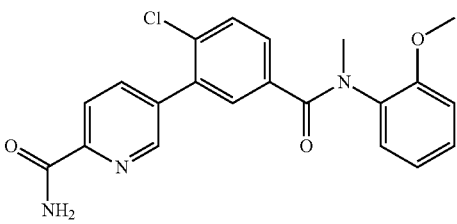 [SMILES: COc1ccccc1N(C)C(=O)c1ccc(Cl)c(-c2ccc(C(N)=O)nc2)c1]

Step 24A: 5-{2-Chloro-5-[(2-methoxy-phenyl)-methyl-carbamoyl]-phenyl}-pyridine-2-carboxylic acid amide To a solution of 4-chloro-3-(6-cyano-pyridin-3-yl)-N-(2-methoxy-phenyl)-N-methyl-benzamide 2-2 (29 mg, 0.077 mmol) in THF (0.5 mL), 1N LiOH (0.5 mL) and K₂CO₃ (10 mg, 0.073 mmol) were added. After stirring for 48 hrs at room temperature, EtOAc and water were added. The aqueous layer was removed and the organic layer was concentrated, dissolved in MeOH and subjected to preparative LCMS to yield 5-{2-chloro-5-[(2-methoxy-phenyl)-methyl-carbamoyl]-phenyl}-pyridine-2-carboxylic acid amide 24-1. MS (M+H)$^+$: 396.0, $t_R$=5.93 min (method 2).

Similarly, 5-{2-chloro-5-[(2-methoxy-phenyl)-methyl-carbamoyl]-phenyl}-4-methyl-pyridine-2-carboxylic acid amide 24-2 was prepared from the corresponding 4-chloro-3-(6-cyano-4-methyl-pyridin-3-yl)-N-(2-methoxy-phenyl)-N-methyl-benzamide 2-10. MS (M+H)$^+$: 410.0, $t_R$=6.12 min (method 2).

Example 25

4-Chloro-N-(2-methoxy-6-methyl-phenyl)-N-methyl-3-(4-methyl-6-pyrazol-1-yl-pyridin 3-yl)-benzamide

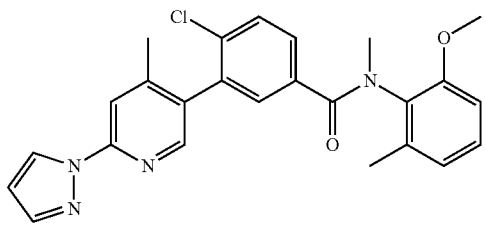 [SMILES: COc1cccc(C)c1N(C)C(=O)c1ccc(Cl)c(-c2cnc(-n3cccn3)cc2C)c1]

Step 25A: 4-Chloro-N-(2-methoxy-6-methyl-phenyl)-N-methyl-3-(4-methyl-6-pyrazol-1-yl-pyridin 3-yl)-benzamide A mixture of 4-chloro-3-(6-chloro-4-methyl-pyridin-3-yl)-N-(2-methoxy-6-methyl-phenyl)-N-methyl-benzamide 2-31 (66.0 mg, 0.16 mmol) and pyrazole (12.9 mg, 0.19 mmol) was added to CuI (6.0 mg, 0.032 mmol), K$_2$CO$_3$ (43.9 mg, 0.32 mmol) and N,N'-dimethylethylenediamine (1.4 mg, 0.016 mmol) in dioxane (1 mL). The reaction vessel was sealed and heated at 130° C. for 24 hrs. The mixture was then filtered and purified by HPLC giving 4-chloro-N-(2-methoxy-6-methyl-phenyl)-N-methyl-3-(4-methyl-6-pyrazol-1-yl-pyridin 3-yl)-benzamide 25-1 (4.5 mg). MS (M+H)$^+$: 446.8, $t_R$=8.60 min (method 2).

Similarly, 4-Chloro-3-(6-imidazol-1-yl-4-methyl-pyridin-3-yl)-N-(2-methoxy-6-methyl-phenyl)-N-methyl-benzamide 25-2 was prepared. MS (M+H)$^+$: 446.8, $t_R$=5.24 min (method 2).

Example 26

4-Chloro-N-(2-methoxy-6-methyl-phenyl)-N-methyl-3-(4-methyl-6-methyl-sulfanylpyridin-3-yl)-benzamide

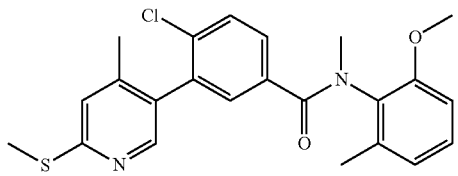

Step 26A: 4-Chloro-N-(2-methoxy-6-methyl-phenyl)-N-methyl-3-(4-methyl-6-methyl-sulfanylpyridin-3-yl)-benzamide A mixture of 4-chloro-3-(6-chloro-4-methyl-pyridin-3-yl)-N-(2-methoxy-6-methyl-phenyl)-N-methyl-benzamide 2-31 (20.0 mg, 0.048 mmol) and sodium thiomethoxide (3.3 mg, 0.048 mmol) in DMSO (1 mL) was heated at 80° C. for 1 hr. The mixture was partitioned between ethyl acetate and water. The organic layer was separated and purified by HPLC yielding 4-chloro-N-(2-methoxy-6-methyl-phenyl)-N-methyl-3-(4-methyl-6-methyl-sulfanylpyridin-3-yl)-benzamide (4.3 mg). MS (M+H)$^+$: 426.9; $t_R$=7.92 min. (method 2).

Example 27

4-Chloro-3-(3,5-dichloro-1-oxy-pyridin-2-yl)-N-(2-methoxy-phenyl)-N-methyl-benzamide

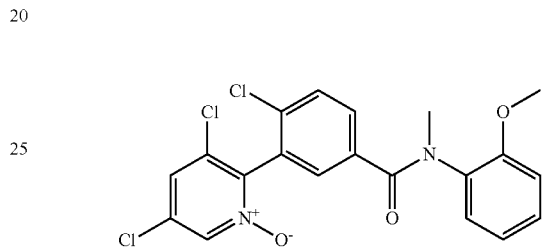

Step 27A: 4-Chloro-3-(3,5-dichloro-1-oxy-pyridin-2-yl)-N-(2-methoxy-phenyl)-N-methyl benzamide A mixture of 4-chloro-3-(3,5-dichloro-pyridin-2-yl)-N-(2-methoxy-phenyl)-N-methyl-benzamide 19-2 (30.0 mg, 0.066 mmol), hydrogen peroxide (10 μL, 33% in water) and acetic acid (0.2 mL) was heated under reflux for 48 hrs followed by addition of more hydrogen peroxide (10 μL, 33% in water). The mixture was then refluxed for another 24 hrs. The mixture was purified by HPLC giving 4-chloro-3-(3,5-dichloro-1-oxy-pyridin-2-yl)-N-(2-methoxy-phenyl)-N-methyl-benzamide (12.3 mg). MS (M+H)$^+$: 436.6; $t_R$=6.52 min. (method 2).

Example 28

4-Chloro-3-(4-cyano-6-trifluoromethyl-pyridin-3-yl)-N-methyl-N-{2-[3-(1H-tetrazol-5-yl)-propoxy]-phenyl}-benzamide

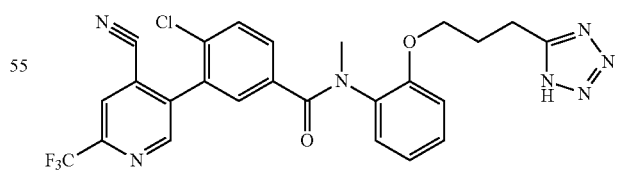

Step 28A: 3-Bromo-4-chloro-N-[2-(3-cyano-propoxy)-phenyl]-N-methyl-benzamide

CsCO$_3$ (5.17 g, 15.87 mmol) was added to a solution of 4-bromo-butyronitrile (0.63 mL, 6.35 mmol) and 3-bromo-4-chloro-N-(2-hydroxy-phenyl)-N-methyl-benzamide (1.80 g, 5.29 mmol, Step 3B) in DMF (20 mL). The mixture was stirred at room temperature for approximately 16 hrs and was partitioned between ethyl acetate and water. The ethyl acetate layer was separated, washed with water and brine, and was dried over MgSO$_4$. The organic filtrate was evaporated to yield 3-bromo-4-chloro-N-[2-(3-cyano-propoxy)-phenyl]-N-methyl-benzamide as a light yellow solid (2.0 g). MS [M+H]$^+$: 408.9; $t_R$=2.39 min. (method 1)

Step 28B: 3-Bromo-4-chloro-N-methyl-N-{2-[3-(1H-tetrazol-5-yl)-propoxy]-phenyl}-benzamide A mixture of 3-bromo-4-chloro-N-[2-(3-cyano-propoxy)-phenyl]-N-methyl-benzamide (2.0 g, 4.9 mmol), azidotributyltin (4.03 mL, 14.7 mmol) and triethylaluminum (7.74 mL, 14.7 mmol, 25% in toluene) in toluene (25 mL) was heated at 80° C. for 5 hrs. The mixture was allowed to cool to room temperature and was acidified with 1N HCl. The mixture was extracted with DCM. The organic layer was washed with water and brine, and was dried. The filtrate was concentrated in vacuo and the residue purified by silica gel column chromatography (eluent: 3% MeOH in DCM) to afford 3-bromo-4-chloro-N-methyl-N-{2-[3-(1H-tetrazol-5-yl)-propoxy]-phenyl}-benzamide (1.93 g). MS [M+H]$^+$: 451.9; $t_R$=2.26 min. (method 1)

Step 28C: 3-Bromo-4-chloro-N-methyl-N-(2-{3-[1-(2-trimethylsilanyl-ethoxymethyl)-1H-tetrazol-5-yl]-propoxy}-phenyl)-benzamide and 3-bromo-4-chloro-N-methyl-N-(2-{3-[2-(2-trimethylsilanyl-ethoxymethyl)-1H-tetrazol-5-yl]-propoxy}-phenyl)-benzamide To 3-bromo-4-chloro-N-methyl-N-{2-[3-(1H-tetrazol-5-yl)-propoxy]-phenyl}-benzamide (1.90 g, 4.2 mmol) in DMF (20 mL) was added 2-(trimethylsilyl)ethoxymethyl chloride (0.89 mL, 5.1 mmol) in one portion, followed by addition of K$_2$CO$_3$ (1.16 g, 8.4 mmol). The mixture was stirred at room temperature for approximately 16 hrs and then was partitioned between ethyl acetate and water. The organic layer was separated, washed with water and brine, and was dried over MgSO$_4$. The filtrate was then concentrated in vacuo and the residue purified by silica gel column chromatography (eluent: 30% ethyl acetate in hexane) to afford 3-bromo-4-chloro-N-methyl-N-(2-{3-[1-(2-trimethylsilanyl-ethoxymethyl)-1H-tetrazol-5-yl]-propoxy}-phenyl)-benzamide and 3-bromo-4-chloro-N-methyl-N-(2-{3-[2-(2-trimethylsilanyl-ethoxymethyl)-1H-tetrazol-5-yl]-propoxy}-phenyl)-benzamide as two regioisomers (upper spot: 736 mg and lower spot: 785 mg). MS [M+H]$^+$: 582.0; $t_R$=2.92 min. (method 1) for upper spot and MS [M+H]$^+$: 582.0; $t_R$=2.75 min. (method 1) for lower spot.

Step 28D: 4-Chloro-N-methyl-3-(4,4,5,5-tetramethyl-[1,3,2]dioxaborolan-2-yl)-N-(2-{3-[1 or 2-(2-trimethylsilanyl-ethoxymethyl)-1H-tetrazol-5-yl]-propoxy}-phenyl)-benzamide The regioisomer corresponding to the upper spot from Step 28C (736 mg, 1.27 mmol) was converted into the corresponding 4-chloro-N-methyl-3-(4,4,5,5-tetramethyl-[1,3,2]dioxaborolan-2-yl)-N-(2-{3-[1 or 2-(2-trimethylsilanyl-ethoxymethyl)-1H-tetrazol-5-yl]-propoxy}-phenyl)-benzamide (800 mg) using the procedure of Step 2D. MS [M+H]$^+$: 628.1; $t_R$=2.98 min. (method 1).

Step 28E: 4-Chloro-3-(4-cyano-6-trifluoromethyl-pyridin-3-yl)-N-methyl-N-(2-{3-[1 or 2-(2-trimethylsilanyl-ethoxymethyl)-2H-tetrazol-5-yl]-propoxy}-phenyl)-benzamide 4-Chloro-N-methyl-3-(4,4,5,5-tetramethyl-[1,3,2]dioxaborolan-2-yl)-N-(2-{3-[1 or 2-(2-trimethylsilanyl-ethoxymethyl)-1H-tetrazol-5-yl]-propoxy}-phenyl)-benzamide (400 mg) was converted into 4-chloro-3-(4-cyano-6-trifluoromethyl-pyridin-3-yl)-N-methyl-N-(2-{3-[1 or 2-(2-trimethylsilanyl-ethoxymethyl)-2H-tetrazol-5-yl]-propoxy}-phenyl)-benzamide (278 mg) using the Suzuki procedure of Step 2E1. MS [M+H]$^+$: 672.0; $t_R$=2.90 min. (method 1).

Step 28F: 4-Chloro-3-(4-cyano-6-trifluoromethyl-pyridin-3-yl)-N-methyl-N-{2-[3-(1H-tetrazol-5-yl)-propoxy]-phenyl}-benzamide 4-Chloro-3-(4-cyano-6-trifluoromethyl-pyridin-3-yl)-N-methyl-N-(2-{3-[1 or 2-(2-trimethylsilanyl-ethoxymethyl)-2H-tetrazol-5-yl]-propoxy}-phenyl)-benzamide (150 mg, 0.22 mmol) was heated to 70° C. in ethanol (1.0 mL) containing concentrated HCl (0.1 mL) for 30 min. Concentration and purification by HPLC afforded 4-chloro-3-(4-cyano-6-trifluoromethyl-pyridin-3-yl)-N-methyl-N-{2-[3-(1H-tetrazol-5-yl)-propoxy]-phenyl}-benzamide (72 mg). MS [M+H]$^+$: 542.0; $t_R$=4.83 min. (method 4).

Example 29

5-{2-Chloro-5-[(2-methoxy-phenyl)-methyl-carbamoyl]-phenyl}-pyridine-2-carboxylic acid amide

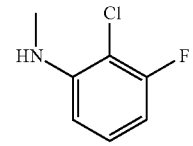

Step 29A: N-(2-Chloro-3-fluoro-phenyl)-formamide

A solution of acetic anhydride (10 mL, 106 mmol) and formic acid (30 mL, 795 mmol) was stirred at room temperature for 10 mins. 2-Chloro-3-fluoroaniline (2.9 g, 20 mmol) was added and the reaction mixture was stirred at 60° C. for 1.5 h. After cooling to room temperature, the solvents were removed in vacuo and the residue was redissolved in DCM (100 mL) and was washed with sat aq. NaHCO$_3$ until the aqueous phase had a measured pH of 8. The organic layer was further washed with water (2×100 mL), separated and dried over MgSO$_4$. Filtration and concentration in vacuo gave N-(2-chloro-3-fluoro-phenyl)-formamide (3.3 g, 95%) as a colorless solid which did not require further purification. MS (M+H)$^+$: 173.9, $t_R$=2.04 min (method 1).

Step 29B: N-Methyl-2-chloro-3-fluoroaniline

To a stirred suspension of 95% lithium aluminum hydride (2.19 g, 58 mmol) in anhydrous THF (10 mL) at 0° C., was added dropwise a solution of N-(2-chloro-3-fluoro phenyl)-formamide (2.3 g, 13.2 mmol) in anhydrous THF (20 mL). The reaction mixture was allowed to slowly warm to room temperature and was stirred for a further 40 mins. The mixture was cooled to 0° C. and was quenched via the sequential addition of water (4 mL), 15% aq. NaOH (2 mL), then water (4 mL). Organics were extracted into a mixture of 3:1 DCM:IPA (100 mL) and washed with water (50 mL). The organic layer was separated and dried over MgSO$_4$. Filtration then concentration in vacuo gave N-methyl-2-chloro-3-fluoroaniline 29-1 (2.07 g, 99%) as a yellow oil. MS (M+H)$^+$: 160.1, $t_R$=2.21 min (method 1).

The following compounds were prepared according to the two step procedure outlined above, using the corresponding commercially available anilines.

| Ex. | | MS (M + H)$^+$ | $t_R$ (min) | HPLC Method |
|---|---|---|---|---|
| 29-1 | (2-Chloro-3-fluoro-phenyl)-methyl-amine | 160.1 | 2.21 | 1 |
| 29-2 | (3-Chloro-5-fluoro-phenyl)-methyl-amine | 159.1 | 2.43 | 1 |
| 29-3 | (4-Fluoro-2-methyl-phenyl)-methyl-amine | 140.1 | 0.98 | 1 |
| 29-4 | (3,4-Difluoro-phenyl)-methyl-amine | 144.0 | 1.59 | 1 |
| 29-5 | (3,5-Difluoro-phenyl)-methyl-amine | 144.0 | 2.29 | 1 |
| 29-6 | (3-Chloro-4-fluoro-phenyl)-methyl-amine | 158.0 | 0.88 | 1 |
| 29-7 | (3-Fluoro-2-methyl-phenyl)-methyl-amine | 140.1 | 1.93 | 1 |
| 29-8 | (3-Fluoro-2-methoxy-phenyl)-methyl-amine | 155.9 | 1.97 | 1 |
| 29-9 | (2-Chloro-5-fluoro-phenyl)-methyl-amine | 159.9 | 2.79 | 1 |
| 29-10 | (2-methoxy-6-methyl-phenyl)-methyl-amine | 152.1 | 1.07 | 1 |
| 29-11 | (2,6-Dimethyl-phenyl)-methyl-amine | 136.1 | 0.65 | 1 |
| 29-12 | (3-Chloro-2-methyl-phenyl)-methyl-amine | 155.9 | 2.45 | 1 |
| 29-13 | (2,3-Difluoro-phenyl)-methyl-amine | 144.0 | 2.53 | 1 |

Example 30

4-Chloro-N-(2-chloro-3-fluoro-phenyl)-N-methyl-3-(6-methyl-2-oxo-4-trifluoromethyl-2H-pyrimidin-1-yl)-benzamide

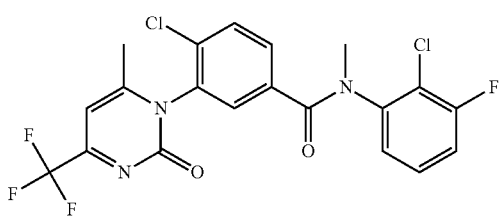 [SMILES: Cc1cc(C(F)(F)F)nc(=O)n1-c1cc(C(=O)N(C)c2cccc(F)c2Cl)ccc1Cl]

Step 30A: 4-Chloro-3-ureido-benzoic acid

A stirred solution of 3-amino-4-chlorobenzoic acid (34.2 g, 200 mmol) and urea (24 g, 400 mmol) in glacial acetic acid (200 mL) was heated at 100° C. for 24 h. The mixture was allowed to cool to room temperature and the resulting precipitate was separated by filtration, washed with water (2×100 mL) and diethyl ether (2×100 mL), then air dried to give 35 g of 4-chloro-3-ureido-benzoic acid as a grey solid that was carried on without further purification.

Step 30B: 4-Chloro-3-(6-methyl-2-oxo-4-trifluoromethyl-2H-pyrimidin-1-yl)-benzoic acid ethyl ester To a stirred suspension of 4-chloro-3-ureido-benzoic acid (26 g, 121 mmol) in ethanol (375 mL) was added 1,1,1-trifluoro-2,4-pentanedione (28 g, 182 mmol) and concentrated (95%) sulfuric acid (50 mL). The reaction mixture was heated at 85° C. for 6 h. After cooling to room temperature, the mixture was partitioned between water (500 mL) and DCM (1 L) and to this was added 6N aq. NaOH, until pH 9-10 attained. The DCM layer was separated and dried over MgSO$_4$ and filtered. Concentration in vacuo gave an orange oil which was purified via silica gel flash chromatography (eluting with a gradient of 10% to 25% EtOAc in hexanes). The resulting orange solid was further triturated with diethyl ether to give 4-chloro-3-(6-methyl-2-oxo-4-trifluoromethyl-2H-pyrimidin-1-yl)-benzoic acid ethyl ester (3.77 g, 9%) as a colorless solid. MS (M+H)$^+$: 360.8, $t_R$=2.670 min (method 1); $^1$H NMR (CDCl$_3$) δ 8.16 (1H, dd, J=8.4, 2.1 Hz), 8.00 (1H, d, J=1.8 Hz), 7.70 (1H, d, J=8.4 Hz), 6.63 (1H, s), 4.39 (2H, q, J=6.9 Hz), 2.15 (3H, s), 1.39 (3H, t, J=6.9 Hz).

Step 30C: 4-Chloro-3-(6-methyl-2-oxo-4-trifluoromethyl-2H-pyrimidin-1-yl)-benzoic acid A stirred suspension of 4-chloro-3-(6-methyl-2-oxo-4-trifluoromethyl-2H-pyrimidin-1-yl)-benzoic acid ethyl ester (3.34 g, 9.26 mmol) in 12N aq. HCl solution (10 mL) was heated at 85° C. for 1 h. After cooling to room temperature the organics were extracted into DCM (3×100 mL). The combined organic layer was dried over MgSO$_4$ and filtered. Concentration in vacuo gave a yellow solid which was purified via silica gel flash chromatography (eluting with a gradient of 5% to 10% MeOH in DCM, followed by 9% MeOH and 1% AcOH in DCM) to give 4-chloro-3-(6-methyl-2-oxo-4-trifluoromethyl-2H-pyrimidin-1-yl)-benzoic acid (1.0 g, 33%) as a cream solid. MS (M+H)$^+$: 332.8, $t_R$=2.364 min (method 1); $^1$H NMR (CDCl$_3$) δ 8.17 (1H, dd, J=8.4, 2.4 Hz), 8.04 (1H, d, J=1.5 Hz), 7.72 (1H, d, J=8.4 Hz), 6.72 (1H, s), 2.17 (3H, s).

Step 30D: 4-Chloro-N-(2-chloro-3-fluoro-phenyl)-N-methyl-3-(6-methyl-2-oxo-4-trifluoromethyl-2H-pyrimidin-1-yl)-benzamide To a stirred solution of 4-chloro-3-(6-methyl-2-oxo-4-trifluoromethyl-2H-pyrimidin-1-yl)-benzoic acid (50 mg, 0.151 mmol) in anhydrous 1,2-dichloroethane (0.5 mL) at room temperature was added oxalyl chloride (23 mg, 0.181 mmol) followed by a catalytic amount of DMF. After stirring for 40 mins, a solution of N-methyl-2-chloro-3-fluoroaniline 29-1 (30 mg, 0.188 mmol) in 1,2-dichloroethane (0.5 mL), followed by 4-(dimethylamino)pyridine (22 mg, 0.179 mmol) were added and the mixture was stirred for 12 h. Direct purification via reverse phase preparative LCMS gave 4-chloro-N-(2-chloro-3-fluoro-phenyl)-N-methyl-3-(6-methyl-2-oxo-4-trifluoromethyl-2H-pyrimidin-1-yl)-benzamide 30-1 (18 mg, 25%) as a colorless solid. MS: 350.5, $t_R$=8.75 min (method 3); $^1$H NMR (CDCl$_3$) δ 7.50 (1H, m), 7.44 (1H, dd, J=8.4, 1.8 Hz), 7.31 (1H, m), 7.26 (1H, s), 6.95 (1H, dd, J=9, 2.1 Hz), 6.79 (1H, m), 6.55 (1H, s), 3.46 (3H, s), 1.93 (3H, s).

The following compounds were prepared according to the procedure described above.

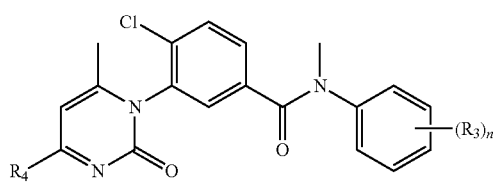

| Ex. | R4 | (R3)n phenyl | Observed mass | tR (min) | HPLC Method |
|---|---|---|---|---|---|
| 30-1 | trifluoromethyl | 2-chloro-3-fluoro-phenyl | 350.5 | 8.75 | 3 |
| 30-2 | trifluoromethyl | 3-chloro-5-fluoro-phenyl | 363.7 | 9.08 | 3 |
| 30-3 | trifluoromethyl | 4-fluoro-2-methyl-phenyl | 452.8 | 6.95 | 2 |
| 30-4 | trifluoromethyl | 3,4-difluoro-phenyl | 343.8 | 7.19 | 3 |
| 30-5 | trifluoromethyl | 3,5-difluoro-phenyl | 330.1 | 6.29 | 3 |
| 30-6 | trifluoromethyl | 3-chloro-4-fluoro-phenyl | 313.7 | 8.53 | 3 |
| 30-7 | trifluoromethyl | 3-fluoro-2-methyl-phenyl | 453.8 | 6.95 | 3 |
| 30-8 | trifluoromethyl | 3-fluoro-2-methoxy-phenyl | 340.2 | 8.06 | 3 |
| 30-9 | trifluoromethyl | 2-chloro-5-fluoro-phenyl | 474.2 | 8.53 | 3 |
| 30-10 | trifluoromethyl | 2-methoxy-6-methyl-phenyl | 465.6 | 8.46 | 3 |
| 30-11 | trifluoromethyl | 2,6-dimethyl-phenyl | 450.2 | 8.63 | 3 |
| 30-12 | trifluoromethyl | 3-chloro-2-methyl-phenyl | 469.8 | 7.28 | 3 |
| 30-13 | trifluoromethyl | 2,3-difluoro-phenyl | 457.9 | 8.15 | 3 |
| 30-14 | trifluoromethyl | 2,3-dimethyl-phenyl | 449.8 | 7.03 | 2 |
| 30-15 | trifluoromethyl | 2-methoxy-phenyl | 451.7 | 6.47 | 2 |
| 30-16 | trifluoromethyl | 2-fluoro-phenyl | 439.7 | 6.48 | 2 |
| 30-17 | trifluoromethyl | 3-fluoro-phenyl | 439.7 | 6.57 | 2 |
| 30-18 | methyl | 2,3-dimethyl-phenyl | 395.8 | 5.25 | 2 |

Example 31

4-Chloro-3-(4-cyano-6-trifluoromethyl-pyridin-3-yl)-N-methyl-N-{2-[2-(5-oxo-4,5-dihydro-[1,3,4]oxadiazol-2-yl)-ethoxy]-phenyl}-benzamide

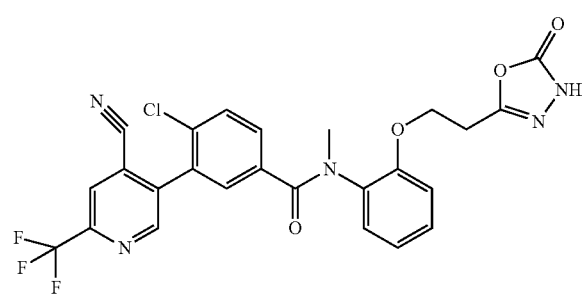 [SMILES: CN(C(=O)c1ccc(Cl)c(-c2cnc(C(F)(F)F)cc2C#N)c1)c1ccccc1OCCc1n[nH]c(=O)o1]

Step 31A: N'-[3-(2-{[4-Chloro-3-(4-cyano-6-trifluoromethyl-pyridin-3-yl)-benzoyl]-methyl-amino}-phenoxy)-propionyl]-hydrazinecarboxylic acid tert-butyl ester EDCI (19.9 mg, 0.104 mmol) was added to a solution of 3-(2-{[4-chloro-3-(4-cyano-6-trifluoromethyl-pyridin-3-yl)-benzoyl]-methyl-amino}-phenoxy)-propionic acid 11-4 (36.3 mg, 0.069 mmol), t-butyl carbazate (13.7 mg, 0.104 mmol), HOBt (14.0 mg, 0.104 mmol) and $Na_2CO_3$ (8.7 mg, 0.104 mmol) in a mixture of DMF (1 mL) and dichloromethane (4 mL). The mixture was stirred at room temperature for approximately 16 hrs and was partitioned between ethyl acetate and water. The ethyl acetate layer was separated, washed with water and brine, and was dried over $MgSO_4$. The organic filtrate was evaporated and purified by prep. TLC plate eluted with hexane and ethyl acetate (1/1) to yield N'-[3-(2-{[4-chloro-3-(4-cyano-6-trifluoromethyl-pyridin-3-yl)-benzoyl]-methyl-amino}-phenoxy)-propionyl]-hydrazinecarboxylic acid tert-butyl ester (40.1 mg, 94%). MS $[M+H]^+$: 619.0; $t_R$=2.40 min. (method 1)

Step 31B: 4-Chloro-3-(4-cyano-6-trifluoromethyl-pyridin-3-yl)-N-methyl-N-{2-[2-(5-oxo-4,5-dihydro-[1,3,4]oxadiazol-2-yl)-ethoxy]-phenyl}-benzamide N'-[3-(2-{[4-chloro-3-(4-cyano-6-trifluoromethyl-pyridin-3-yl)-benzoyl]-methyl-amino}-phenoxy)-propionyl]-hydrazinecarboxylic acid tert-butyl ester (40.1 mg, 0.065 mmol) was stirred in 4N HCl in dioxane (5 mL) for 2 hrs and was concentrated. The residue was suspended in toluene (5 mL) containing DIPEA (25.2 mg, 0.19 mmol). Phosgene (20% in toluene, 8.2 µL, 0.077 mmol) was added and the mixture was stirred at rt for 24 hrs. The mixture was concentrated and purified via reverse phase preparative LCMS to give 4-chloro-3-(4-cyano-6-trifluoromethyl-pyridin-3-yl)-N-methyl-N-{2-[2-(5-oxo-4,5-dihydro-[1,3,4]oxadiazol-2-yl)-ethoxy]-phenyl}-benzamide 31-1 (17 mg). MS $[M+H]^+$: 544.1; $t_R$=5.11 min. (method 3)

Example 32

2-Chloro-5-fluoro-quinoline-3-carbonitrile

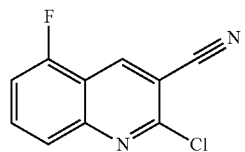 [SMILES: N#Cc1cc2c(F)cccc2nc1Cl]

Step 32A: (2-Amino-6-fluoro-phenyl)-methanol

LAH (987 mg, 26 mmol) was added slowly to a solution of 2-amino-6-fluoro-benzoic acid (2.69 g, 17.3 mmol) in dry THF (20 mL) at 0° C. The mixture was stirred at room temperature for approximately 1 hr and cooled to 0° C. again. $Na_2SO_4 \cdot 10H_2O$ (10 g) was added slowly with stirring for 20 minutes. The mixture was filtered, the solid was washed with THF. The solution was concentrated to yield a yellow solid as (2-amino-6-fluoro-phenyl)-methanol (2.49 g). MS $[M-OH]^+$: 124.1; $t_R$=0.57 min. (method 1)

Step 32B: 2-Amino-6-fluoro-benzaldehyde

To (2-amino-6-fluoro-phenyl)-methanol (2.49 g, 17.3 mmol) in dichloromethane (30 mL) was added $MnO_2$ (3.01 g, 34.7 mmol, activated). The mixture was refluxed for 3 hrs and then filtered over celite. The mixture was concentrated and purified via silica gel flash chromatography (eluting with 30% ethyl acetate in hexane) to give 2-amino-6-fluoro-benzaldehyde as a yellow solid (1.23 g). $t_R$=2.20 min. (method 1)

Step 32C: 5-Fluoro-2-oxo-1,2-dihydro-quinoline-3-carbonitrile

To a solution of MeOH (60 mL) containing 2-amino-6-fluoro-benzaldehyde (1.19 g, 8.6 mmol) and methyl cyanoacetate (0.91 mL, 10.3 mmol) was added sodium methoxide (2.93 mL, 12.8 mmol, 25% in MeOH). The mixture was stirred at rt for 16 hrs. The resulting yellow precipitates were filtered, washed with MeOH and then stirred in 1N HCl (75 mL) for 2 hrs at rt. The solid was filtered, washed with water and dried in vacuo to yield 5-fluoro-2-oxo-1,2-dihydro-quinoline-3-carbonitrile (1.2 g) as a white solid. MS [M+H]$^+$: 189.1; $t_R$=2.00 min. (method 1)

Step 32D: 2-Chloro-5-fluoro-quinoline-3-carbonitrile

5-Fluoro-2-oxo-1,2-dihydro-quinoline-3-carbonitrile (0.80 g, 4.3 mmol) was heated in POCl$_3$ (10 mL) for 3 hrs. The mixture was concentrated and partitioned in ethyl acetate and water. The organic layer was separated, washed with NaHCO$_3$, dried and concentrated. The residue was crystallized from a mixture of hexane and ethyl acetate to give 2-chloro-5-fluoro-quinoline-3-carbonitrile 32-1 as a white solid (0.83 g). $^1$HNMR (CDCl$_3$), δ, 8.82 (1H, s), 7.83-7.92 (2H, m), 7.33-7.41 (1H, m).

The following compounds were prepared according to the procedure described above.

| Ex. | | MS (M + H)$^+$ | $t_R$ (min) | HPLC Method |
|---|---|---|---|---|
| 32-1 | 2-Chloro-5-fluoro-quinoline-3-carbonitrile | 207.0 | 2.40 | 1 |
| 32-2 | 2-Chloro-8-fluoro-quinoline-3-carbonitrile | 207.2 | 2.38 | 1 |
| 32-3 | 2-Chloro-5,6,7,8-tetrafluoro-quinoline-3-carbonitrile | — | 2.56 | 1 |

Example 33

4-(2-{[4-Chloro-3-(3-cyano-5-fluoro-quinolin-2-yl)-benzoyl]-methyl-amino}-phenoxy)-butyric acid

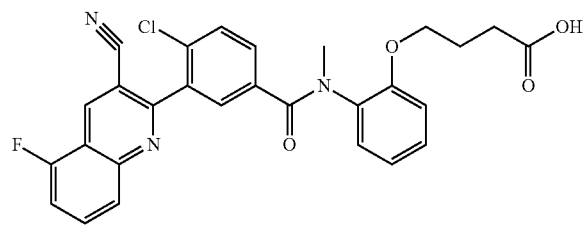 [SMILES: CN(C(=O)c1ccc(Cl)c(-c2nc3cccc(F)c3cc2C#N)c1)c1ccccc1OCCCC(=O)O]

Step 33A: 3-Bromo-4-chloro-N(2-hydroxy-phenyl)-N-methyl-benzamide (alternative synthesis to Step 3B)

3-Bromo-4-chloro-benzoyl chloride (Step 2A, 106.9 mmol) in acetonitrile (300 mL) was added dropwise over 30 minutes to a vigorously stirring solution of 2-methylamino-phenol (15.1 g, 122.9 mmol) and NaHCO$_3$ (18.0 g, 213.7 mmol) in acetonitrile (200 mL) and water (200 mL). The mixture was stirred for additional 1 h and then concentrated to remove acetonitrile. The solid was filtered, washed with HCl (1N, 600 mL) and water (500 mL), and dried. The solid was dissolved in dichloromethane (500 mL) and n-butylamine (20 mL) was added. The mixture was stirred at rt for 16 hrs and concentrated. The residue was partially purified via silica gel flash chromatography (eluting with 20% to 35% ethyl acetate in hexane) and then crystallized from hexane/ethyl acetate (75/25) to give 3-bromo-4-chloro-N-(2-hydroxy-phenyl)-N-methyl-benzamide (20.5 g) as a white solid. MS [M+H]$^+$: 339.7/341.8; $t_R$=2.19 min. (method 1)

Step 33B: 4-{2-[(3-Bromo-4-chloro-benzoyl)-methyl-amino]-phenoxy}-butyric acid tert-butyl ester 4-{2-[(3-Bromo-4-chloro-benzoyl)-methyl-amino]-phenoxy}-butyric acid tert-butyl ester (6.24 g) was similarly prepared according to Step 3C as a light yellow solid from 3-bromo-4-chloro-N-(2-hydroxy-phenyl)-N-methyl-benzamide (7.9 g, 23.2 mmol). MS [M-tert-but]$^+$: 426.0/428.0; $t_R$=2.69 min. (method 1)

Step 33C: 4-(2-{[4-Chloro-3-(4,4,5,5-tetramethyl-[1,3,2]dioxaborolan-2-yl)-benzoyl]-methyl-amino}-phenoxy)-butyric acid tert-butyl ester 4-(2-{[4-Chloro-3-(4,4,5,5-tetramethyl-[1,3,2]dioxaborolan-2-yl)-benzoyl]-methyl-amino}-phenoxy)-butyric acid tert-butyl ester (5.36 g) was similarly prepared according to Step 2D from 4-{2-[(3-bromo-4-chloro-benzoyl)-methyl-amino]-phenoxy}-butyric acid tert-butyl ester (6.23 g, 12.9 mmol). MS [M+H]$^+$: 530.2; $t_R$=2.72 min. (method 1)

Step 33D: 4-(2-{[4-Chloro-3-(3-cyano-5-fluoro-quinolin-2-yl)-benzoyl]-methyl-amino}-phenoxy)-butyric acid tert-butyl ester 4-(2-{[4-Chloro-3-(3-cyano-5-fluoro-quinolin-2-yl)-benzoyl]-methyl-amino}-phenoxy)-butyric acid tert-butyl ester (80.2 mg) was similarly prepared according to Step 15D from 4-{2-[(3-bromo-4-chloro-benzoyl)-methyl-amino]-phenoxy}-butyric acid tert-butyl ester (106.4 mg, 0.2 mmol) and 2-chloro-5-fluoro-quinoline-3-carbonitrile 32-1 (41.5 mg, 0.2 mmol). MS [M+H]$^+$: 574.3; $t_R$=2.97 min. (method 1)

Step 33E: 4-(2-{[4-Chloro-3-(3-cyano-5-fluoro-quinolin-2-yl)-benzoyl]-methyl-amino}-phenoxy)-butyric acid 4-(2-{[4-Chloro-3-(3-cyano-5-fluoro-quinolin-2-yl)-benzoyl]-methyl-amino}-phenoxy)-butyric acid tert-butyl ester (80.2 mg) was stirred in 50% trifluoroacetic acid in dichloromethane (2 mL) for 2 hrs and purified via reverse phase preparative LCMS to afford 4-(2-{[4-chloro-3-(3-cyano-5- fluoro-quinolin-2-yl)-benzoyl]-methyl-amino}-phenoxy)-butyric acid 33-1 (22.9 mg). MS [M+H]$^+$: 518.4; $t_R$=3.47 min. (method 3)

The following compounds were prepared according to the procedure described above

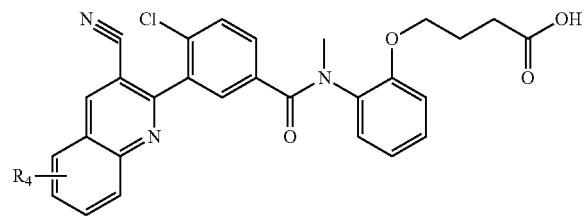

| Ex. | R$_4$ | MS (M + H)$^+$ | $t_R$ (min) | HPLC Method |
|---|---|---|---|---|
| 33-1 | 5-fluoro | 518.4 | 3.47 | 3 |
| 33-2 | 8-fluoro | 518.3 | 3.41 | 3 |
| 33-3 | 5,6,7,8-tetrafluoro | 572.4 | 3.72 | 3 |

Example 34

4-{5-Chloro-4-(4-cyano-6-trifluoromethyl-pyridin-3-yl)-2-[(2-methoxy-phenyl)-methyl-carbamoyl]phenoxy}-butyric acid

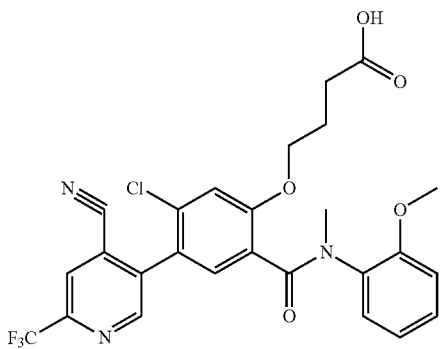 [SMILES: COc1ccccc1N(C)C(=O)c1cc(-c2cnc(C(F)(F)F)cc2C#N)c(Cl)cc1OCCCC(=O)O]

Step 34A: 5-Bromo-2-(3-tert-butoxycarbonyl-propoxy)-4-chloro-benzoic acid 3-tert-butoxycarbonyl-propyl ester A mixture of 5-bromo-4-chloro-2-hydroxy-benzoic acid (5 g, 19.9 mmol), 4-bromo-butyric acid tert-butyl ester (13.2 g, 59.7 mmol) and K$_2$CO$_3$ (11.1 g, 79.6 mmol) in DMF (100 mL) was heated at 80° C. for 2 days. The solid was filtered off. The solution was concentrated and purified via silica gel flash chromatography (eluting with 20% ethyl acetate in hexane) to give 5-bromo-2-(3-tert-butoxycarbonyl-propoxy)-4-chloro-benzoic acid 3-tert-butoxycarbonyl-propyl ester (8.2 g). MS [M-iso-butene+H]$^+$: 480.9; $t_R$=3.32 min. (method 1)

Step 34B: 5-Bromo-2-(3-tert-butoxycarbonyl-propoxy)-4-chloro-benzoic acid

A mixture of 5-bromo-2-(3-tert-butoxycarbonyl-propoxy)-4-chloro-benzoic acid 3-tert-butoxycarbonyl-propyl ester (8.2 g, 15.3 mmol) and LiOH (19.1 mL, 4 N, 76.6 mmol) in THF (150 mL) was stirred at rt for 16 hrs. The mixture was acidified by saturated NaHSO$_4$ (50 mL) and extracted with ethyl acetate. The ethyl acetate layer was dried over Na$_2$SO$_4$, filtered and concentrated. The residue was purified via silica gel flash chromatography (eluting with 50% ethyl acetate in hexane), followed by crystallization in hexane/ethyl acetate (10/1) to afford 5-bromo-2-(3-tert-butoxycarbonyl-propoxy)-4-chloro-benzoic acid as white crystals (2.5 g). MS [M-(iso-butene+OH)]$^+$: 320.8; $t_R$=2.38 min. (method 1)

Step 34C: 5-Bromo-2-(3-tert-butoxycarbonyl-propoxy)-4-chloro-benzoic acid 2-trimethylsilanyl-ethyl ester To a stirring dichloromethane solution (40 mL) containing 5-bromo-2-(3-tert-butoxycarbonyl-propoxy)-4-chloro-benzoic acid (2.3 g, 5.9 mmol) and 2-(trimethylsilyl)-ethanol (1.8 g, 8.9 mmol), dicyclohexyl-carbodiimide (1.83 g, 8.9 mmol) and DMAP (108 mg, 0.9 mmol) were added. The mixture was stirred at rt for 16 hrs and was concentrated. The residue was purified via silica gel flash chromatography (eluting with 20% ethyl acetate in hexane) to afford 5-bromo-2-(3-tert-butoxycarbonyl-propoxy)-4-chloro-benzoic acid 2-trimethylsilanyl-ethyl ester (3.2 g). MS ion (APCl): 482.0, 441.0, 410.9. $t_R$=3.61 min (method 1)

Step 34D: 2-(3-tert-Butoxycarbonyl-propoxy)-4-chloro-5-(4,4,5,5-tetramethyl-[1,3,2]dioxaborolan-2-yl)-benzoic acid-2-trimethylsilanyl-ethyl ester 2-(3-tert-Butoxycarbonyl-propoxy)-4-chloro-5-(4,4,5,5-tetramethyl-[1,3,2]dioxaborolan-2-yl-benzoic acid-2-trimethylsilanyl-ethyl ester (2.7 g) was similarly prepared according to Step 2D from 5-bromo-2-(3-tert-butoxycarbonyl-propoxy)-4-chloro-benzoic acid 2-trimethylsilanyl-ethyl ester (3.2 g). MS ion (APCl): 513.2, 459.1; $t_R$=3.62 min. (method 1)

Step 34E: 2-(3-tert-Butoxycarbonyl-propoxy)-4-chloro-5-(4-cyano-6-trifluoromethyl-pyridin-3-yl)-benzoic acid 2-trimethylsilanyl-ethyl ester 2-(3-tert-Butoxycarbonyl-propoxy)-4-chloro-5-(4-cyano-6-trifluoromethyl-pyridin-3-yl)-benzoic acid 2-trimethylsilanyl-ethyl ester (1.3 g) was similarly prepared according to Step 2E.1 or Step 3E from 5-bromo-2-(3-tert-butoxycarbonyl-propoxy)-4-chloro-benzoic acid 2-trimethylsilanyl-ethyl ester (2.2 g). MS ion (APCl): 501.1; $t_R$=3.59 min (method 1)

Step 34F: 2-(3-tert-Butoxycarbonyl-propoxy)-4-chloro-5-(4-cyano-6-trifluoromethyl-pyridin-3-yl)-benzoic acid A mixture of 2-(3-tert-butoxycarbonyl-propoxy)-4-chloro-5-(4-cyano-6-trifluoromethyl-pyridin-3-yl)-benzoic acid 2-trimethylsilanyl-ethyl ester (1.3 g, 2.2 mmol) and tetrabutyl-ammonium fluoride (6.6 mL, 6.6 mmol, 1 M in THF) in THF (20 mL) was stirred at rt for 30 minutes. The mixture was then concentrated and diluted with ether. The ether layer was washed with water, dried and concentrated to yield 2-(3-tert-butoxycarbonyl-propoxy)-4-chloro-5-(4-cyano-6-trifluoromethyl-pyridin-3-yl)-benzoic acid (0.8 g). MS [M+H]$^+$: 485.1; $t_R$=2.96 min (method 1)

Step 34G: 4-{5-Chloro-4-(4-cyano-6-trifluoromethyl-pyridin-3-yl)-2-[(2-methoxy-phen-methyl-carbamoyl]-phenoxy}-butyric acid A mixture of 2-(3-tert-butoxycarbonyl-propoxy)-4-chloro-5-(4-cyano-6-trifluoromethyl-pyridin-3-yl)-benzoic acid (30 mg, 0.06 mmol), 2-methoxy-N-methylaniline (9.4 mg, 0.07 mmol), triethylamine (12.5 mg, 0.12 mmol) and 2-(7-aza-1H-benzotriazole-1-yl)-1,1,3,3-tetramethyluronium hexafluorophosphate (HATU, 35 mg, 0.09 mL) in dichloromethane (1 mL) containing DMF (0.1 mL) was stirred at rt for 16 hrs. The mixture was then partitioned in water and dichloromethane. The organic layer was washed with water, dried and concentrated to yield a crude 4-{5-chloro-4-(4-cyano-6-trifluoromethyl-pyridin-3-yl)-2-[(2-methoxy-phenyl)-methyl-carbamoyl]-phenoxy}-butyric acid t-butyl ester.

Alternatively, 2-methoxyaniline was used for amide formation, followed by performing N-methylation according to Step 2C to afford the same intermediate.

The above crude material was stirred in 50% trifluoroacetic acid in dichloromethane (1 mL) for 2 hrs and then purified via reverse phase preparative LCMS to afford 4-{5-chloro-4-(4-cyano-6-trifluoromethyl-pyridin-3-yl)-2-[(2-methoxy-phenyl)-methyl-carbamoyl]-phenoxy}-butyric acid 34-1 (4.5 mg).

The following compounds were prepared according to the procedure described above:

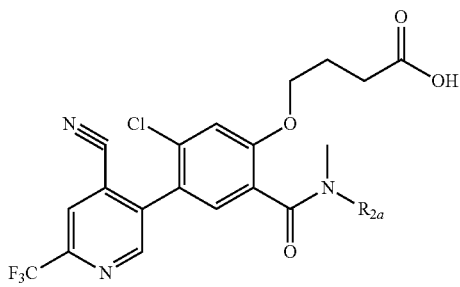

| Ex. | $R_{2a}$ | MS (M + H)$^+$ | $t_R$ (min) | HPLC Method |
|---|---|---|---|---|
| 34-1 | 2-methoxy-phenyl | 548.3 | 3.91 | 3 |
| 34-2 | 4-chloro-2-methoxy-phenyl | 582.3 | 4.06 | 3 |
| 34-3 | 2-trifluoromethoxy-phenyl | 602.3 | 4.08 | 3 |
| 34-4 | 4-fluoro-2-methoxy-phenyl | 566.3 | 3.70 | 3 |
| 34-5 | 2-methoxymethyl-phenyl | 562.2 | 3.49 | 3 |
| 34-6 | 3-chloro-2-methoxy-phenyl | 582.0 | 8.20 | 2 |
| 34-7 | 5-chloro-2-methoxy-phenyl | 582.0 | 8.10 | 2 |
| 34-8 | phenyl | 518.3 | 3.81 | 3 |
| 34-9 | 4-chloro-2-methoxymethyl-phenyl | 596.1 | 3.82 | 3 |
| 34-10 | 2-methoxycarbonyl-phenyl | 576.2 | 3.35 | 3 |
| 34-11 | 3-fluoro-2-methoxy-phenyl | 566.8 | 3.70 | 3 |
| 34-12 | 5-methyl-2-methoxy-phenyl | 562.4 | 3.74 | 3 |
| 34-13 | 2,5-dimethoxy-phenyl | 577.6 | 3.53 | 3 |
| 34-14 | 2,4-dimethoxy-phenyl | 577.6 | 3.67 | 3 |
| 34-15 | 2-oxazol-5-yl-phenyl | 585.7 | 3.37 | 3 |
| 34-16 | 2-furan-2-yl-phenyl | 584.4 | 3.83 | 3 |
| 34-17 | benzyl | 523.3 | 3.90 | 3 |
| 34-18 | 2-pyridyl | 519.3 | 3.51 | 3 |
| 34-19 | 6-methoxy-pyridin-2-yl | 549.2 | 3.43 | 3 |
| 34-20 | 3-methyl-pyridin-2-yl | 532.8 | 3.39 | 3 |
| 34-21 | 6-methyl-pyridin-2-yl | 532.8 | 3.12 | 3 |
| 34-22 | methyl | 455.7 | 2.95 | 3 |
| 34-23 | 3-methyl-butyl | 512.0 | 3.69 | 3 |
| 34-24 | 2-methoxy-ethyl | 500.1 | 3.09 | 3 |
| 34-25 | cyclopropylmethyl | 496.0 | 3.47 | 3 |
| 34-26 | 6-fluoro-2-methoxy-phenyl | 566.1 | 3.73 | 3 |

Example 35

4-Chloro-5-(4-cyano-6-trifluoromethyl-pyridin-3-yl)-N-(2-methoxy-phenyl)-N-methyl-2-[3-(1H-tetrazol-5-yl)-propoxy]-benzamide

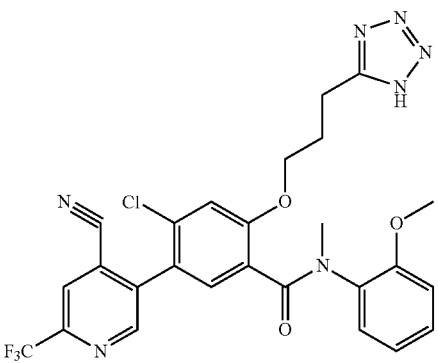 [SMILES: COc1ccccc1N(C)C(=O)c1cc(-c2cnc(C(F)(F)F)cc2C#N)c(Cl)cc1OCCCc1nnn[nH]1]

Step 35A: 5-Bromo-4-chloro-2-hydroxy-N-(2-methoxy-phenyl)-N-methyl-benzamide To a stirring dichloromethane (40 mL) solution containing 5-bromo-4-chloro-2-hydroxybenzoic acid (2.0 g, 8.0 mmol), were added triethylamine (2.2 mL, 16.0 mmol), HATU (4.5 g, 12 mmol) and 2-methoxyl-N-methylaniline (1.19 g, 8.7 mmol). The mixture was stirred at rt for 16 hrs and water was added. The organic layer was separated, washed with NaHCO$_3$, dried over Na$_2$SO$_4$, filtered and concentrated. The residue was purified via silica gel flash column chromatography eluting with 20% ethyl acetate in hexane to afford 5-bromo-4-chloro-2-hydroxy-N-(2-methoxy-phenyl)-N-methyl-benzamide (300 mg). MS [M+H]$^+$: 371.9; $t_R$=2.60 min (method 1)

Alternatively, a mixture of 5-bromo-4-chloro-2-hydroxybenzoic acid (5 g, 19.9 mmol), 2-methoxy-N-methylaniline (3.13 g, 22.9 mmol) and P$_2$O$_5$ (5.36 g, 37.8 mmol) in anhydrous xylene was heated at 60° C. for 2 hrs and then refluxed for 17 hrs. The mixture was concentrated and purified via silica gel flash column chromatography eluted with ethyl acetate in hexane (20%) to give 5-bromo-4-chloro-2-hydroxy-N-(2-methoxy-phenyl)-N-methyl-benzamide (3.3 g).

Step 35B: 5-Bromo-4-chloro-2-(3-cyano-propoxy)-N-(2-methoxy-phenyl)-N-methyl-benzamide To a stirring DMF solution (6 mL) containing 5-bromo-4-chloro-2-hydroxy-N-(2-methoxy-phenyl)-N-methyl-benzamide (300 mg, 0.81 mmol) was added 4-bromo-butyronitrile (0.096 mL, 0.97 mmol) and K$_2$CO$_3$ (223 mg, 1.62 mmol). The mixture was heated at 50° C. for 8 hrs. Additional 0.5 eq. of 4-bromobutyronitrile and 0.5 eq of K$_2$CO$_3$ were added and the mixture was heated for another 8 hrs.

The mixture was diluted with dichloromethane, washed with brine, dried over Na₂SO₄, filtered and concentrated. The residue was purified via silica gel flash column chromatography to afford 5-bromo-4-chloro-2-(3-cyano-propoxy)-N-(2-methoxy-phenyl)-N-methyl-benzamide (241 mg). MS [M+H]⁺: 439.1; $t_R$=2.62 min (method 1)

Step 35C: 5-Bromo-4-chloro-N-(2-methoxy-phenyl)-N-methyl-2-[3-(1H-tetrazol-5-yl)-propoxy]-benzamide 5-Bromo-4-chloro-N-(2-methoxy-phenyl)-N-methyl-2-[3-(1H-tetrazol-5-yl)-propoxy]-benzamide (226 mg) was similarly prepared according to Step 28B from the corresponding 5-bromo-4-chloro-2-(3-cyano-propoxy)-N-(2-methoxy-phenyl)-N-methyl-benzamide (241 mg). MS [M+H]⁺: 482.1; $t_R$=2.48 min (method 1)

Steps 35D: 4-Chloro-5-(4-cyano-6-trifluoromethyl-pyridin-3-yl)-N-(2-methoxy-phenyl)-N-methyl-2-[3-(1H-tetrazol-5-yl)-propoxy]-benzamide 4-Chloro-5-(4-cyano-6-trifluoromethyl-pyridin-3-yl)-N-(2-methoxy-phenyl)-N-methyl-2-[3-(1H-tetrazol-5-yl)-propoxy]-benzamide 35-1 was prepared from 5-bromo-4-chloro-N-(2-methoxy-phenyl)-N-methyl-2-[3-(1H-tetrazol-5-yl)-propoxy]-benzamide via stepwise reactions of Steps 28C, D, E and F. MS [M+H]⁺: 572.2; $t_R$=7.48 min (method 2)

Example 36

2,2-Dimethyl-propionic acid 3-(2-{[4-chloro-3-(4-cyano-6-trifluoromethyl-pyridin-3-yl)-benzoyl]-methyl-amino}-phenoxy)-propionyloxymethyl ester

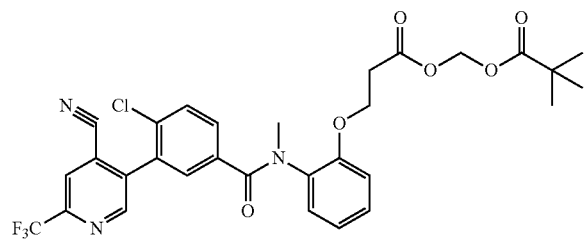 [SMILES: CN(C(=O)c1ccc(Cl)c(-c2cnc(C(F)(F)F)cc2C#N)c1)c1ccccc1OCCC(=O)OCOC(=O)C(C)(C)C]

Step 36A: 2,2-Dimethyl-propionic acid 3-(2-{[4-chloro-3-(4-cyano-6-trifluoromethyl-pyridin-3-yl)-benzoyl]-methyl-amino}-phenoxy)-propionyloxymethyl ester A mixture of 3-(2-{[4-chloro-3-(4-cyano-6-trifluoromethyl-pyridin-3-yl)-benzoyl]-methyl-amino}-phenoxy)-propionic acid 11-4 (500 mg, 0.95 mmol), chloromethyl pivalate (276.4 µL, 1.9 mmol), triethylamine (399 µL, 2.85 mmol), NaI (142.5 mg, 0.95 mmol) in DMF (5 mL) was stirred at rt for 2 days. Ethyl acetate was added and the mixture was washed with water and brine, dried over MgSO₄, filtered and concentrated. The residue was purified via silica gel flash column chromatography eluting with 20% ethyl acetate in hexane to afford 2,2-dimethyl-propionic acid 3-(2-{[4-chloro-3-(4-cyano-6-trifluorometethyl-pyridin-3-yl)-benzoyl]-methyl-amino}-phenoxy)-propionyloxymethyl ester 36-1 as a white foam. MS [M+H]⁺: 618.2; $t_R$=32.7 min (method 5).

Similarly, 4-{5-chloro-4-(4-cyano-6-trifluoromethyl-pyridin-3-yl)-2-[(2-methoxy-phenyl)-methyl-carbamoyl]-phenoxy}-butyric acid 2,2-dimethyl-propionyloxymethyl ester 36-2 was prepared from 34-1. MS [M+H]⁺: 662.2; $t_R$=6.87 min (method 3)

Example 37

3-(2-{[4-Chloro-3-(4-cyano-6-trifluoromethyl-pyridin-3-yl)-benzoyl]-methyl-amino}-phenoxy)-propionic acid 1-cyclohexyloxycarbonyloxy-ethyl ester

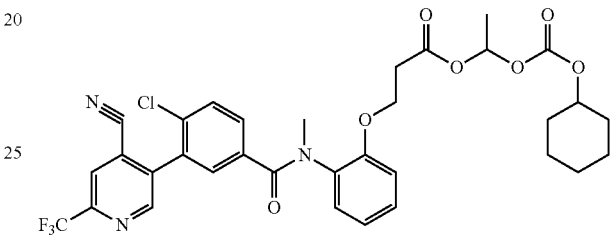

Step 37A: 3-(2-{[4-Chloro-3-(4-cyano-6-trifluoromethyl-pyridin-3-yl)-benzoyl]-methyl-amino}-phenoxy)-propionic acid 1-cyclohexyloxycarbonyloxy-ethyl ester A mixture of 3-(2-{[4-chloro-3-(4-cyano-6-trifluoromethyl-pyridin-3-yl)-benzoyl]-methyl-amino}-phenoxy)-propionic acid 11-4 (500 mg, 0.95 mmol), carbonic acid 1-chloroethyl cyclohexyl ester (393 mg, 1.9 mmol), triethylamine (399 µL, 2.85 mmol), and NaI (142.5 mg, 0.95 mmol) in DMF (5 mL) were stirred at 60° C. for 1 day. Ethyl acetate was added and the mixture was washed with water and brine, dried over MgSO₄, filtered and concentrated. The residue was purified via silica gel flash column chromatography eluting with 20% ethyl acetate in hexane to afford 3-(2-{[4-Chloro-3-(4-cyano-6-trifluoromethyl-pyridin-3-yl)-benzoyl]-methyl-amino}-phenoxy)-propionic acid 1-cyclohexyloxycarbonyloxy-ethyl ester 37-1. MS [M+H]⁺: 674.2; $t_R$=35.7 min (method 5).

Similarly, 3-(2-{[4-Chloro-3-(4-cyano-6-trifluoromethyl-pyridin-3-yl)-benzoyl]-methyl-amino}-phenoxy)-propionic acid 1-isopropoxycarbonyloxy-ethyl ester 37-2 was prepared from 11-4 and carbonic acid 1-chloroethyl isopropyl ester. MS [M+H]⁺: 634.2; $t_R$=32.5 min (method 5).

Similarly, 4-{5-chloro-4-(4-cyano-6-trifluoromethyl-pyridin-3-yl)-2-[(2-methoxy-phenyl)-methyl-carbamoyl]-phenoxy}-butyric acid 1-cyclohexyloxycarbonyloxy-ethyl ester 37-3 was prepared from 34-1. MS [M+H]⁺: 718.3; $t_R$=7.23 min (method 3).

Similarly, 4-{5-chloro-4-(4-cyano-6-trifluoromethyl-pyridin-3-yl)-2-[(2-methoxy-phenyl)-methyl-carbamoyl]-phenoxy}-butyric acid 1-isopropoxycarbonyloxy-ethyl ester 37-4 was prepared from 34-1. MS [M+H]⁺: 678.3; $t_R$=6.73 min (method 3).

Example 38

4-Chloro-5-(4-cyano-6-trifluoromethyl-pyridin-3-yl)-2-methoxy-N-(2-methoxy-phenyl)-N-methyl-benzamide

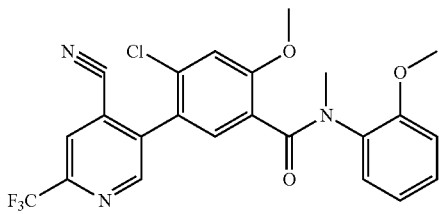 [SMILES: COc1cc(Cl)c(-c2cnc(C(F)(F)F)cc2C#N)cc1C(=O)N(C)c1ccccc1OC]

Step 38A: 4-Chloro-2-methoxy-5-(4,4,5,5-tetramethyl-[1,3,2]dioxaborolan-2-yl)-benzoic acid methyl ester 4-Chloro-2-methoxy-5-(4,4,5,5-tetramethyl-[1,3,2]dioxaborolan-2-yl)-benzoic acid methyl ester (9.8 g) was prepared from 5-bromo-4-chloro-2-methoxybenzoic acid methyl ester (10.0 g) according to the procedure of Step 20. MS [M+H]$^+$: 327.1; $t_R$=2.96 min (method 1)

Step 38B: 4-Chloro-5-(4-cyano-6-trifluoromethyl-pyridin-3-yl)-2-methoxy-benzoic acid methyl ester 4-Chloro-5-(4-cyano-6-trifluoromethyl-pyridin-3-yl)-2-methoxy-benzoic acid methyl ester (5.5 g) was prepared according to Step 2E.1 from 4-chloro-2-methoxy-5-(4,4,5,5-tetramethyl-[1,3,2]dioxaborolan-2-yl)-benzoic acid methyl ester (9.8 g) and 5-bromo-2-trifluoromethyl-isonicotinonitrile 1-1 (7.6 g). MS [M+H]$^+$: 371.0; $t_R$=2.83 min (method 1)

Steps 38C: 4-Chloro-5-(4-cyano-6-trifluoromethyl-pyridin-3-yl)-2-methoxy-benzoic acid A mixture of 4-chloro-5-(4-cyano-6-trifluoromethyl-pyridin-3-yl)-2-methoxy-benzoic acid methyl ester (1.2 g, 3.2 mmol) and trimethyltin hydroxide (1.75 g, 9.7 mmol) in 1,2-dichloroethane (50 mL) was heated to 80° C. in a sealed tube for 4 hrs. Additional 5.0 eq. of trimethyltin hydroxide was added and the mixture was heated for total of 48 hrs. The mixture was then cooled to rt, quenched with HCl (2N, 40 mL) and diluted with 1,2-dichloroethane. The organic layer was separated, dried over Na$_2$SO$_4$, filtered and concentrated. The residue was purified via silica gel flash column chromatography eluting with dichloromethane:methanol (9:1) to afford 4-chloro-5-(4-cyano-6-trifluoromethyl-pyridin-3-yl)-2-methoxy-benzoic acid (723 mg). NMR (CDCl$_3$), δ, 8.82 (1H, s), 7.94 (1H, s), 7.81 (1H, s), 7.20 (1H, s), 3.90 (3H, s).

Step 38C.1: 4-Chloro-5-(4-cyano-6-trifluoromethyl-pyridin-3-yl)-2-methoxy-benzoic acid (Alternative Synthesis)

N$_2$ was bubbled through a solution of THF (8 mL) and water (2 mL) containing 5-carboxy-2-chloro-4-methoxyphenylboronic acid (460.8 mg, 2.0 mmol) and 5-bromo-2-trifluoromethyl-isonicotinonitrile 1-1 (478 mg, 1.9 mmol) for 10 minutes. K$_3$PO$_4$ (1.2 g, 5.7 mmol), t-Bu$_3$P.HBF$_4$ (82.7 mg, 0.28 mmol), and Pd$_2$dba$_3$ (91.0 mg, 0.1 mmol) were added under N$_2$ atmosphere. The mixture was sealed, stirred at rt for 3 hrs, and diluted with ethyl acetate. The organic layer was separated, washed with brine, dried over MgSO$_4$, filtered and concentrated. The residue was purified via silica gel flash column chromatography eluting with 10% MeOH in dichloromethane to give 4-chloro-5-(4-cyano-6-trifluoromethyl-pyridin-3-yl)-2-methoxy-benzoic acid (301 mg).

Similarly, 4-chloro-5-(4-cyano-6-trifluoromethyl-pyridin-3-yl)-benzoic acid was prepared according to the above procedure from 5-carboxy-2-chloro-phenylboronic acid and 5-bromo-2-trifluoromethyl-isonicotinonitrile 1-1.

Step 38D: 4-Chloro-5-(4-cyano-6-trifluoromethyl-pyridin-3-yl)-2-methoxy-N-(2-methoxy-phenyl)-N-methyl-benzamide To a mixture of 2-methoxyl-N-methylaniline (27.7 mg, 0.2 mmol) and Et$_3$Al (196 μL, 1.9 M in toluene, 0.2 mmol) in 1,2-dichloroethane (1 mL) which was preheated at 50° C. for 10 min under N$_2$ atmosphere, was added 4-chloro-5-(4-cyano-6-trifluoromethyl-pyridin-3-yl)-2-methoxy-benzoic acid methyl ester (50 mg, 0.14 mmol). The mixture was sealed in N$_2$ atmosphere and heated at 80° C. for 16 hrs. Upon cooling to rt, the mixture was quenched with 2 N HCl (5 mL) and diluted with 1,2-dichloroethane. The organic layer was separated and concentrated. The residue was purified via reverse phase preparative LCMS to yield 4-chloro-5-(4-cyano-6-trifluoromethyl-pyridin-3-yl)-2-methoxy-N-(2-methoxy-phenyl)-N-methyl-benzamide 38-1 (4.9 mg). MS [M+H]$^+$ 475.9; $t_R$=5.91 min (method 3)

Example 39

4-Chloro-5-(4-cyano-6-trifluoromethyl-pyridin-3-yl)-N-(2-methyl-phenyl)-2-methoxy-N-methyl-benzamide

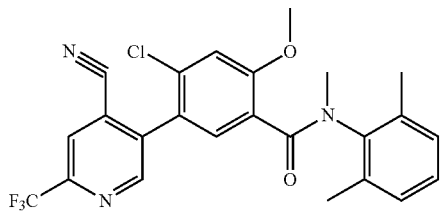 [SMILES: COc1cc(Cl)c(-c2cnc(C(F)(F)F)cc2C#N)cc1C(=O)N(C)c1c(C)cccc1C]

Step 39A: 4-Chloro-2-methoxy-5-(6-trifluoromethyl-pyridin-3-yl)-benzoyl chloride To a stirring dichloromethane solution (5 mL) containing 4-chloro-5-(4-cyano-6-trifluoromethyl-pyridin-3-yl)-2-methoxy-benzoic acid (Step 38C or 38C.1, 436 mg, 1.2 mmol), was added 2 drops of DMF and then oxalyl chloride (128 μL, 1.5 mmol) under N$_2$. The mixture was stirred at rt for 2 hrs and concentrated to yield 4-chloro-2-methoxy-5-(6-trifluoromethyl-pyridin-3-yl)-benzoyl chloride as a solid, which was used in the next step without further purification.

Similarly, 4-chloro-5-(4-cyano-6-trifluoromethyl-pyridin-3-yl)-benzoyl chloride was prepared from 4-chloro-5-(4-cyano-6-trifluoromethyl-pyridin-3-yl)-benzoic acid (Step 38C.1).

Step 39B: 4-Chloro-5-(4-cyano-6-trifluoromethyl-pyridin-3-yl)-N-(2,6-dimethyl-phenyl)-2-methoxy-benzamide To 4-chloro-2-methoxy-5-(4-cyano-6-trifluoromethyl-pyridin-3-yl)-benzoyl chloride (70 mg, 0.19 mmol) in DCM (0.5 mL) were added triethylamine (39 μL, 0.28 mmol) and 2,6-dimethylaniline (28 μL, 0.22 mmol). The mixture was stirred at rt for 12 hrs and was purified via a prep TLC plate eluting with ethyl acetate in hexane (30%) to give 4-chloro-5-(4-cyano-6-trifluoromethyl-pyridin-3-yl)-N-(2,6-dimethyl-phenyl)-2-methoxy-benzamide (55.0 mg). MS [M+H]$^+$ 460.2; $t_R$=2.85 min (method 1)

Step 39C: 4-Chloro-5-(4-cyano-6-trifluoromethyl-pyridin-3-yl)-N-(2,6-dimethyl-phenyl)-2-methoxy-N-methyl-benzamide To 4-chloro-5-(4-cyano-6-trifluoromethyl-pyridin-3-yl)-N-(2,6-dimethyl-phenyl)-2-methoxy-benzamide (55.0 mg, 0.12 mmol) in dry DMF (0.5 mL) was added NaH (9.6 mg, 0.32 mmol) and iodomethane (0.15 mL, 0.24 mmol). The mixture was stirred at rt overnight, quenched with 0.5 mL of MeOH and 2 drops of trifluoroacetic acid, and purified via reverse phase preparative LCMS to yield 4-chloro-5-(4-cyano-6-trifluoromethyl-pyridin-3-yl)-N-(2,6-dimethyl-phenyl)-2-methoxy-N-methyl-benzamide 39-1 (8.3 mg). MS [M+H]$^+$ 471.1; $t_R$=6.25 min (method 3)

The following compounds were prepared according to the procedure described above, where in some cases, Step 39C was not necessary due to availability of the N-methyl amine.

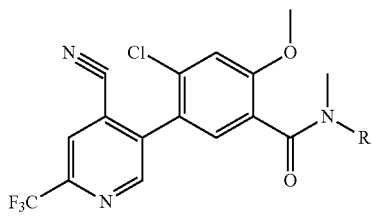

| Ex. | R | MS (M + H)$^+$ | $t_R$ (min) | HPLC Method |
|---|---|---|---|---|
| 39-1 | 2,6-dimethyl-phenyl | 474.1 | 6.25 | 3 |
| 39-2 | 2-methoxycarbonyl-phenyl | 504.2 | 5.82 | 3 |
| 39-3 | 2,6-dimethoxy-phenyl | 506.1 | 5.81 | 3 |
| 39-4 | 2-fluoro-6-methoxy-phenyl | 494.2 | 6.03 | 3 |
| 39-5 | 5-fluoro-2-methoxy-phenyl | 494.2 | 6.02 | 3 |
| 39-6 | 2,6-difluoro-phenyl | 482.2 | 6.10 | 3 |
| 39-7 | phenyl | 446.1 | 5.91 | 3 |
| 39-8 | 5-chloro-2-methoxycarbonyl-phenyl- | 538.1 | 6.24 | 3 |
| 39-9 | 2-(2,2,2-trifluoro-ethoxy)-phenyl | 544.2 | 6.18 | 3 |
| 39-10 | 2-methoxy-6-methyl-phenyl | 490.2 | 6.10 | 3 |
| 39-11 | 5-fluoro-2-methyl-phenyl | 478.1 | 6.17 | 3 |
| 39-12 | 2-oxazol-5-yl-phenyl | 513.1 | 5.53 | 3 |
| 39-13 | 3-methoxy-pyridin-2-yl | 477.1 | 6.85 | 2 |
| 39-14 | Pyridin-2-yl | 447.2 | 5.33 | 3 |
| 39-15 | benzyl | 460.3 | 6.11 | 3 |
| 39-16 | 2-fluoro-benzyl | 478.3 | 6.17 | 3 |
| 39-17 | 2-methoxy-benzyl | 490.3 | 6.20 | 3 |
| 39-18 | 3-methoxy-benzyl | 490.3 | 6.11 | 3 |
| 39-19 | 2-(2-dimethylamino-ethoxy)-benzyl | 547.3 | 6.02 | 3 |
| 39-20 | 4-methoxy-pyridin-3-yl | 477.3 | 5.01 | 3 |
| 39-21 | 3-methyl-pyridin-2-yl | 461.2 | 5.29 | 3 |
| 39-22 | benzothiazol-2-yl | 503.1 | 6.39 | 3 |
| 39-23 | 6-methoxy-pyridin-2-yl | 477.1 | 5.98 | 3 |

Example 40

4-Chloro-3-(4-cyano-6-trifluoromethyl-pyridin-3-yl)-N-methyl-N-{2-[2-(5-oxo-4,5-dihydro-1H-[1,2,4]triazol-3-yl)-ethoxy]-phenyl}-benzamide

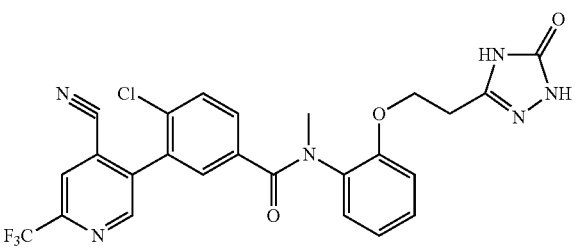 [SMILES: CN(C(=O)c1ccc(Cl)c(-c2cnc(C(F)(F)F)cc2C#N)c1)c1ccccc1OCCc1n[nH]c(=O)[nH]1]

Step 40A: 4-Chloro-3-(4-cyano-6-trifluoromethyl-pyridin-3-yl)-N-methyl-N-{2-[2-(5-oxo-4,5-dihydro-1H-[1,2,4]triazol-3-yl)-ethoxy]-phenyl}-benzamide To a stirring solution of dichloromethane (5.0 mL) containing 4-chloro-3-(4-cyano-6-trifluoromethylpyridin3-yl)-N-[2-(3-hydroxy-propoxy)-phenyl]-N-methyl-benzamide 9-4 (304.0 mg, 0.62 mmol), was added Dess-Martin periodinane (263.2 mg, 0.62 mmol). The mixture was stirred at rt for 2 hrs. The solid was filtered off and resulting solution was concentrated to give the aldehyde intermediate which was redissolved in t-BuOH (9.0 mL), followed by addition of water (3 mL) and NH$_2$NH$_2$ (20.5 μL, 0.65 mmol) at 0°-5° C. After additional stirring at rt for 30 min, the mixture was treated with NaOCN (64.5 mg, 0.99 mmol) and acetic acid (71.7 μL, 1.24 mmol) at 10° C. and stirred for another 2 hrs at the same temperature. A 10% bleach solution (0.37 mL, 0.62 mmol) was added and the mixture was stirred at rt for 2 days. The mixture was diluted with water, extracted with ethyl acetate and purified by prep. TLC plate eluting with 5% MeOH in dichloromethane to yield 4-chloro-3-(4-cyano-6-trifluoromethyl-pyridin-3-yl)-N-methyl-N-{2-[2-(5-oxo-4,5-dihydro-1H-[1,2,4]triazol-3-yl)-ethoxy]-phenyl}-benzamide 40-1 (63.4 mg). MS [M+H]$^+$ 543.2; $t_R$=6.46 min (method 2).

Example 41

4-Chloro-3-(4-cyano-6-trifluoromethyl-pyridin-3-yl)-N-{2-[2-(3-methylsulfonyl-ureido)-ethoxy]-phenyl}-N-methyl-benzamide

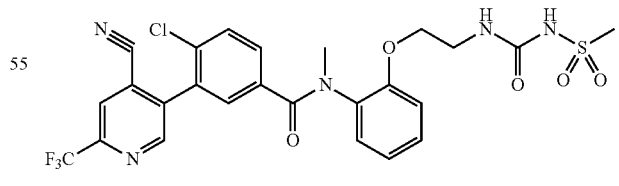

Step 41A: 4-Chloro-3-(4-cyano-6-trifluoromethyl-pyridin-3-yl)-N-{2-[2-(3-methylsulfonyl-ureido)-ethoxy]-phenyl}-N-methyl-benzamide To a mixture of 3-(2-{[4-chloro-3-(4-cyano-6-trifluoromethyl-pyridin-3-yl)-benzoyl]-methyl-amino}-phenoxy)-propionic acid 11-4 (272.9 mg, 0.54 mmol), CH$_3$SO$_2$NH$_2$ (51.5 mg, 0.54 mmol) and K$_2$CO$_3$ (224.4 mg, 1.63 mmol) in dioxane (4.0 mL), was added diphenylphosphoryl azide (141 µL, 0.65 mmol). The mixture was heated at 85° C. for 3 hrs, diluted with water, acidified to pH 3 by NaHSO$_4$ aqueous solution, then extracted with ethyl acetate. The organic solution was then dried, concentrated and purified by prep. TLC plate eluting with 4% MeOH in dichloromethane to afford 4-chloro-3-(4-cyano-6-trifluoromethyl-pyridin-3-yl)-N-{2-[2-(3-methylsulfonyl-ureido)-ethoxy]-phenyl}-N-methyl-benzamide 41-1 (20.5 mg). MS [M+H]$^+$ 596.3; $t_R$=7.29 min (method 2).

Example 42

4-Chloro-5-(4-cyano-6-trifluoromethyl-pyridin-3-yl)-N-(2-methoxy-phenyl)-N-methyl-2-[2-(2-oxo-pyrrolidin-1-yl)-ethoxy]-benzamide Step 42A: 4-Chloro-5-(4-cyano-6-trifluoromethyl-pyridin-3-yl)-N-(2-methoxy-phenyl)-N-methyl-methyl-2-[2-(2-oxo-pyrrolidin-1-yl)-ethoxy]-benzamide 4-Chloro-5-(4-cyano-6-trifluoromethyl-pyridin-3-yl)-N-(2-methoxy-phenyl)-N-methyl-methyl-2-[2-(2-oxo-pyrrolidin-1-yl)-ethoxy]-benzamide 42-1 was prepared according to Step 21A to Step 21G of Example 21. MS: 573.3 (M+H)$^+$, $t_R$=5.36 min (method 3).

The follow compounds were prepared similarly:

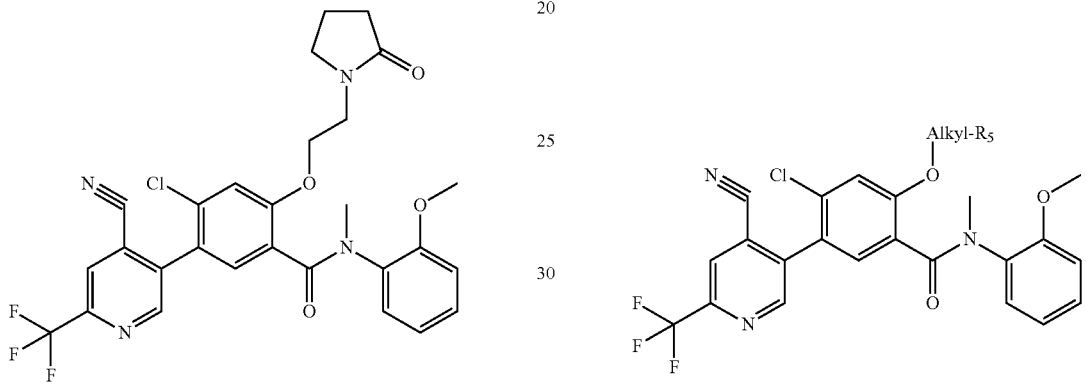

| Ex. | -Alkyl- | —R$_5$ | MS (M + H)$^+$ | $t_R$ (min) | HPLC Method |
|---|---|---|---|---|---|
| 42-1 | —CH$_2$CH$_2$— | 2-oxo-pyrrolidin-1-yl | 573.3 | 5.36 | 3 |
| 42-2 | —CH$_2$CH$_2$— | Morpholin-4-yl | 575.1 | 9.00 | 3 |
| 42-3 | —CH$_2$CH$_2$— | Imidazol-1-yl | 556.0 | 5.25 | 3 |
| 42-4 | —CH$_2$CH$_2$— | Pyridin-2-yl | 568.7 | 5.84 | 3 |
| 42-5 | —CH$_2$CH$_2$— | 4-Methyl-4,5-dihydrothiazol-5-yl | 587.4 | 5.94 | 3 |
| 42-6 | —CH$_2$CH$_2$CH$_2$— | Pyridin-2-yl | 581.6 | 8.38 | 3 |
| 42-7 | —CH$_2$CH$_2$CH$_2$— | 1H-pyrazol-4-yl | 570.2 | 5.56 | 3 |
| 42-8 | —CH$_2$CH$_2$O— | Pyridin-2-yl | 583.2 | 6.32 | 3 |
| 42-9 | —CH$_2$CH$_2$CH$_2$— | Pyridin-4-yl | 581.5 | 5.96 | 3 |
| 42-10 | —CH$_2$CH$_2$CH$_2$— | Pyrrol-1-yl | 569.4 | 6.92 | 3 |
| 42-11 | —CH$_2$CH$_2$CH$_2$— | Imidazol-1-yl | 570.2 | 5.61 | 3 |
| 42-12 | —CH$_2$CH$_2$CH$_2$— | pyrazol-1-yl | 570.2 | 6.08 | 3 |
| 42-13 | —CH$_2$CH$_2$CH$_2$— | 1,2,4-triazol-1-yl | 571.2 | 5.65 | 3 |
| 42-14 | —CH$_2$CH$_2$CH$_2$— | 1-methyl-1H-pyrazol-3-yl | 584.3 | 5.99 | 3 |
| 42-15 | —CH$_2$CH$_2$CH$_2$O— | Pyrdin-2-yl | 5971 | 8.67 | 2 |
| 42-16 | —CH$_2$CH$_2$— | NH$_2$ | 505.3 | 5.77 | 3 |
| 42-17 | —CH$_2$CH$_2$— | NHMe | 519.3 | 5.58 | 3 |
| 42-18 | —CH$_2$CH$_2$(NH$_2$)CH$_2$— | OH | 535.3 | 5.38 | 3 |

Example 43

4-{5-Chloro-4-(4-cyano-6-trifluoromethyl-pyridin-3-yl)-2-[(2-methoxy-phenyl)-methyl-carbamoyl]-phenoxy}-butyric acid ethyl ester

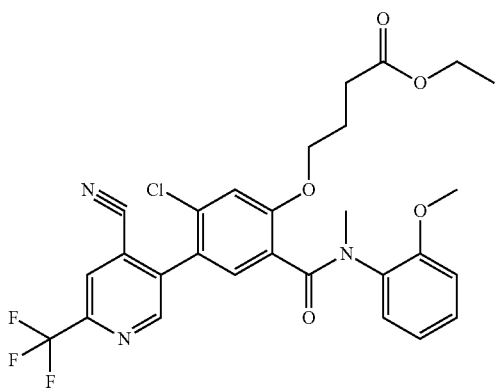 [SMILES: CCOC(=O)CCCOc1cc(Cl)c(-c2cnc(C(F)(F)F)cc2C#N)cc1C(=O)N(C)c1ccccc1OC]

Step 43A: 4-{5-Chloro-4-(4-cyano-6-trifluoromethyl-pyridin-3-yl)-2-[(2-methoxy-phenyl)-methyl-carbamoyl]-phenoxy}-butyric acid ethyl ester To 4-{5-Chloro-4-(4-cyano-6-trifluoromethyl-pyridin-3-yl)-2-[(2-methoxy-phenyl)-methyl-carbamoyl]-phenoxy}-butyric acid in ethanol (1 mL), 10 drops of $SOCl_2$ were added. The mixture was stirred at rt for 24 hrs. The crude was purified via reverse phase preparative LCMS to afford 4-{5-chloro-4-(4-cyano-6-trifluoromethyl-pyridin-3-yl)-2-[(2-methoxy-phenyl)-methyl-carbamoyl]-phenoxy}-butyric acid ethyl ester 43-1 (12.2 mg). MS: $[M+H]^+$ 576.3; $t_R$=6.33 min (method 3).

Example 44

{5-Chloro-4-(4-cyano-6-trifluoromethyl-pyridin-3-yl)-2-[(2-methoxy-phenyl)-methyl-carbamoyl]-phenyl}-acetic acid

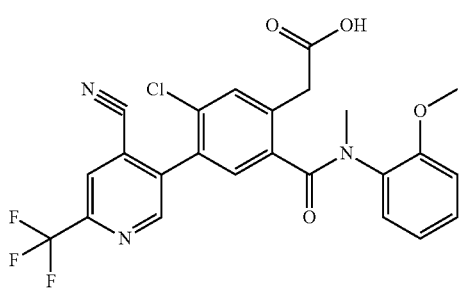 [SMILES: COc1ccccc1N(C)C(=O)c1cc(-c2cnc(C(F)(F)F)cc2C#N)c(Cl)cc1CC(=O)O]

Step 44A: 5-Bromo-4-chloro-2-fluoro-N-(2-methoxy-phenyl)-N-methyl-benzamide

2-Methoxy-N-methylaniline (7.4 g, 53.8 mmol) and triethylamine (10.9 g, 107.7 mmol) were added to 5-bromo-4-chloro-2-fluoro-benzoyl chloride (Step 21D, 11.7 g, 43.1 mmol) in DCM (200 mL) at 0° C. The mixture was then allowed to warm to rt and concentrated. The mixture was partitioned in water and ethyl acetate. The organic layer was separated, washed with $NaHSO_4$ solution, water and brine, and was dried. After filtration and concentration, the residue was purified via silica gel flash column chromatography eluting with ethyl acetate in hexane (50%) to give 5-bromo-4-chloro-2-fluoro-N-(2-methoxy-phenyl)-N-methyl-benzamide (12.5 g). MS: $[M+H]^+$ 374.0/372.0; $t_R$=2.70 min (method 1)

Step 44B: 2-{4-Bromo-5-chloro-2-[(2-methoxy-phenyl)methyl-carbamoyl]-phenyl}-malonic acid dimethyl ester t-BuOK (7.23 g, 64.5 mmol) was added to dimethyl malonate (8.52 g, 7.3 mL, 64.5 mmol) in dry DMF (60 mL). The mixture was heated at 90° C. for 10 min to form the corresponding sodium salt which was added to a DMF (40 mL) solution containing 5-bromo-4-chloro-2-fluoro-N-(2-methoxy-phenyl)-N-methyl-benzamide (3.0 g, 8.1 mmol) under $N_2$. The mixture was heated with stirring at 80° C. for 16 hrs, diluted with ethyl acetate, washed with water and brine, and dried over $MgSO_4$. The filtrate was concentrated and subject to silica gel column chromatography eluting with ethyl acetate in hexane (20%) to yield 2-{4-bromo-5-chloro-2-[(2-methoxy-phenyl)-methyl-carbamoyl]-phenyl}-malonic acid dimethyl ester (1.4 g) as a light yellow oil. MS: $[M+H]^+$ 487.9/486.0; $t_R$=2.82 min (method 1)

Step 44C: 2-{4-Bromo-5-chloro-2-[(2-methoxy-phenyl)-methyl-carbamoyl]-phenyl}-acetic acid A mixture of 2-{4-bromo-5-chloro-2-[(2-methoxy-phenyl)-methyl-carbamoyl]-phenyl}-malonic acid dimethyl ester (1.4 g, 2.8 mmol) and $LiOH \cdot H_2O$ (0.7 g, 16.7 mmol) was stirred at 60° C. in a mixture of THF (20 mL) and water (2 mL) for 24 hrs, then acidified by 1N HCl to pH 4. The mixture was extracted with ethyl acetate. The ethyl acetate layer was then washed with water and brine, and was dried over $MgSO_4$. The filtrate was then concentrated and purified by silica gel flash column chromatography eluting with 10% MeOH in DCM to yield 2-{4-bromo-5-chloro-2-[(2-methoxy-phenyl)-methyl-carbamoyl]-phenyl}-acetic acid (427 mg). MS: $[M+H]^+$ 413.9/412.0; $t_R$=2.60 min (method 1)

Step 44D: {4-Bromo-5-chloro-2-[(2-methoxy-phenyl)-methyl-carbamoyl]-phenyl}-acetic acid 2-trimethylsilanyl-ethyl ester To a solution of DCM (10 mL) containing 2-{4-bromo-5-chloro-2-[(2-methoxy-phenyl)-methyl-carbamoyl]-phenyl}-acetic acid (427 mg, 1.0 mmol) and 2-trimethylsilylethanol (183 mg, 1.5 mmol), were added DMAP (18.9 mg, 0.15 mmol) and DCC (320 mg, 1.5 mmol). The mixture was stirred at rt for 24 hrs, concentrated, and then directly purified via silica gel column chromatography eluting with ethyl acetate in hexane (20%) to yield {4-bromo-5-chloro-2-[(2-methoxy-phenyl)-methyl-carbamoyl]-phenyl}-acetic acid 2-trimethylsilanyl-ethyl ester (520 mg). MS: $(M-CH_2CH_2)^+$ 487.9/486.0; $t_R$=3.34 min (method 1).

Step 44E: [5-Chloro-2-[(2-methoxy-phenyl)-methyl-carbamoyl]-4-(4,4,5,5-tetramethyl[1,3,2]dioxaborolan-2-yl)-phenyl]-acetic acid 2-trimethylsilanyl-ethyl ester

[5-Chloro-2-[(2-methoxy-phenyl)-methyl-carbamoyl]-4-(4,4,5,5-tetramethyl[1,3,2]dioxaborolan-2-yl)-phenyl]-acetic acid 2-trimethylsilanyl-ethyl ester (570 mg) was obtained from the corresponding {4-bromo-5-chloro-2-[(2-methoxy-phenyl)-methyl-carbamoyl]-phenyl}-acetic acid 2-trimethylsilanyl-ethyl ester (520 mg) according to Step 2D of Example 2. MS: [M+H]$^+$ 560.2; $t_R$=3.45 min (method 1).

Step 44F: {5-Chloro-4-(4-cyano-6-trifluoromethyl-pyridin-3-yl)-2-[(2-methoxy-phenyl)-methyl-carbamoyl]-phenyl}-acetic acid {5-Chloro-4-(4-cyano-6-trifluoromethyl-pyridin-3-yl)-2-[(2-methoxy-phenyl)-methyl-carbamoyl]-phenyl}-acetic acid 2-trimethylsilanyl-ethyl ester (615 mg) was obtained from [5-chloro-2-[(2-methoxy-phenyl)-methyl-carbamoyl]-4-(4,4,5,5-tetramethyl[1,3,2]dioxaborolan-2-yl)-phenyl]-acetic acid 2-trimethylsilanyl-ethyl ester (570 mg) and 5-bromo-2-trifluoromethyl-isonicotinonitrile 1-1 (305 mg) according to Step 38C.1 of Example 38. The crude was redissolved in THF (10 mL) and tetrabutylammonium fluoride (1M in THF, 3 mL) was added. The mixture was stirred at rt for 1 hr, acidified by 1N HCl (2 mL) and extracted with ether. The ether layer was then washed with water, brine and dried over MgSO$_4$. The filtrate was concentrated and purified via silica gel flash column chromatography eluting with 10% MeOH in DCM to yield {5-chloro-4-(4-cyano-6-trifluoromethyl-pyridin-3-yl)-2-[(2-methoxy-phenyl)-methyl-carbamoyl]-phenyl}-acetic acid 44-1 (246 mg). MS: [M+H]$^+$ 504.0; $t_R$=7.54 min (method 2).

Example 45

4-Chloro-3-(4-cyano-6-trifluoromethyl-pyridin-3-yl)-N-methyl-N-{2-[2-(1H-tetrazol-5-yl)-ethoxy]-phenyl}-benzamide

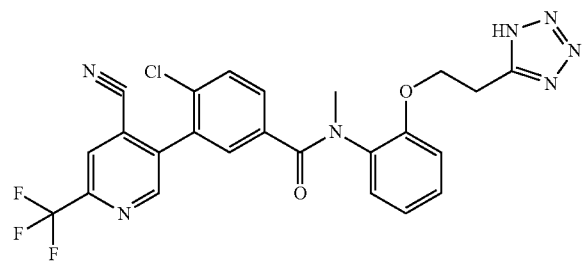 [SMILES: CN(C(=O)c1ccc(Cl)c(-c2cnc(C(F)(F)F)cc2C#N)c1)c1ccccc1OCCc1nnn[nH]1]

Steps 45A: 3-(2-Methylamino-phenoxy)-propionitrile

A solution of 2-methylaminophenol (0.74 g, 6.0 mmol), Triton B (60 μL, 40% in water) and acrylonitrile (4.0 mL, 60 mmol) was refluxed for 16 hrs. The mixture was diluted with ethyl acetate. The organic layer was then washed with water and brine, and was dried over MgSO$_4$. After filtration and concentration, the residue was purified via silica gel flash column chromatography eluting with 20% ethyl acetate in hexane to give 3-(2-methylamino-phenoxy)-propionitrile (4.0 g) as a brown oil. [M+H]$^+$ 177.1; $t_R$=0.715 min (method 1).

Steps 45B: Methyl-{2-[2-(1H-tetrazol-5-yl)-ethoxy]-phenyl}-amine

To a solution of 3-(2-methylamino-phenoxy)-propionitrile (1.55 g, 8.8 mmol) and azidotributyltin (3.6 mL, 13.2 mmol) in toluene (30 mL) was added triethylaluminum (9.3 mL, 17.6 mmol, 1.9 M in toluene). The mixture was heated at 80° C. for 16 hrs. The mixture was diluted with water (100 mL) and ethyl acetate (200 mL). The ethyl acetate layer was separated and removed. The resulting methyl-{2-[2-(1H-tetrazol-5-yl)-ethoxy]-phenyl}-amine stayed in the aqueous solution and was used in the next step without purification. [M+H]$^+$ 220.1; $t_R$=0.388 min (method 1).

Steps 45C: 4-Chloro-3-(4-cyano-6-trifluoromethyl-pyridin-3-yl)-N-methyl-N-{2-[2-(1H-tetrazol-5-yl)-ethoxy]-phenyl}-benzamide The stirring aqueous solution of methyl-{2-[2-(1H-tetrazol-5-yl)-ethoxy]-phenyl}-amine was basified with sat. NaHCO$_3$ and diluted with acetonitrile (40 mL). 4-Chloro-5-(6-trifluoromethyl-pyridin-3-yl)-benzoyl chloride (Step 39A, 2.9 g, 8.8 mmol) in acetonitrile (20 mL) was added dropwise. The mixture was stirred for 2 hrs, acidified, and concentrated to remove acetonitrile. The concentrated mixture was extracted with ethyl acetate. The organic layer was then washed with water and brine, and was dried over MgSO$_4$. After filtration and concentration, the residue was purified via silica gel flash column chromatography eluting with 2% MeOH in DCM and then further purified via silica gel flash column chromatography eluting with 50% ethyl acetate in hexane to produce 4-chloro-3-(4-cyano-6-trifluoromethyl-pyridin-3-yl)-N-methyl-N-{2-[2-(1H-tetrazol-5-yl)-ethoxy]-phenyl}-benzamide 45-1 (3.2 g). [M+H]$^+$ 528.2; $t_R$=3.43 min (method 3).

Similarly, 4-chloro-5-(4-cyano-6-trifluoromethyl-pyridin-3-yl)-2-methoxy-N-methyl-N-{2-[2-(1H-tetrazol-5-yl)-ethoxy]-phenyl}-benzamide 45-2 was prepared. [M+H]$^+$ 558.1; $t_R$=7.82 min (method 2).

Example 46

4-Chloro-5-(4-cyano-6-trifluoromethyl-pyridin-3-yl)-2-(3-isoxazol-4-ylpropoxy)-N-(2 methoxy phenyl)-N-methyl-benzamide

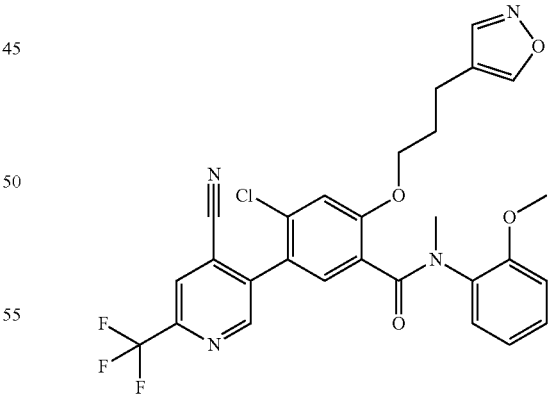

Step 46A: 4-Chloro-5-(4-cyano-6-trifluoromethyl-pyridin-3-yl)-2-(3-isoxazol-4-yl-propoxy)-N-(2-methoxyphenyl)-N-methyl-benzamide To a solution of 4-chloro-5-(4-cyano-6-trifluoromethyl-pyridin-3-yl)-2-hydroxy-N-(2-methoxy-phenyl)-N-methyl-benzamide (30 mg, 0.065 mmol) in THF (700 μL), 3-isoxazol-4-yl-propan-1-ol (9 mg, 0.071 mmol), triphenylphosphine (26 mg, 0.089 mmol) and DIAD (20 μL, 0.098 mmol) were added. The mixture was stirred at rt overnight, concentrated, diluted with 1 mL MeOH and purified by prep HPLC to give 4-chloro-5-(4-cyano-6-trifluoromethyl-pyridin-3-yl)-2-(3-isoxazol-4-yl-propoxy)-N-(2-methoxyphenyl)-N-methyl-benzamide 46-1. MS: 571.2 (M+H)$^+$, $t_R$=6.12 min (method 3).

The following compounds were prepared similarly.

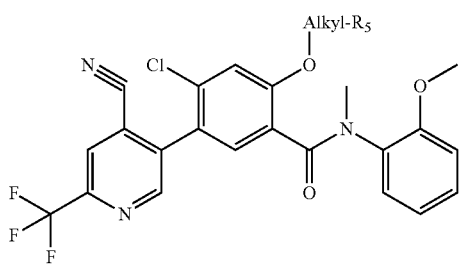

| Ex. | -Alkyl- | —R$_5$ | MS (M + H)$^+$ | $t_R$ (min) | HPLC Method |
|---|---|---|---|---|---|
| 46-1 | —CH$_2$CH$_2$CH$_2$— | isoxazol-4-yl | 571.2 | 6.12 | 3 |
| 46-2 | —CH$_2$CH$_2$— | 2-methoxyphenyl | 596.5 | 6.97 | 3 |
| 46-3 | —CH$_2$CH$_2$— | Pyrazin-2-yl | 568.4 | 5.71 | 3 |
| 46-4 | —CH$_2$CH$_2$CH$_2$— | 1,3-dioxo-1,3-dihydro-isoindol-2-yl | 649.3 | 6.39 | 3 |

Example 47

2-(2-Acetylamino-ethoxy)-4-chloro-5-(4-cyano-6-trifluoromethyl-pyridin-3-yl)-N-(2-methoxy-phenyl)-N-methyl-benzamide

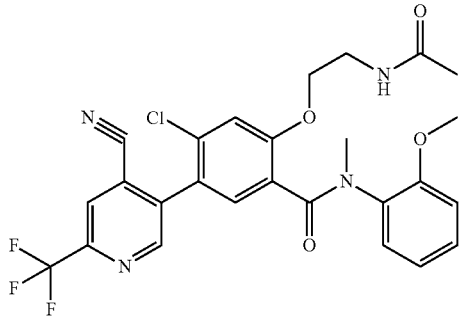 [SMILES: COc1ccccc1N(C)C(=O)c1cc(-c2cnc(C(F)(F)F)cc2C#N)c(Cl)cc1OCCNC(C)=O]

Step 47A: 2-(2-Acetylamino-ethoxy)-4-chloro-5-(4-cyano-6-trifluoromethyl-pyridin-3-yl)-N-(2-methoxy-phenyl)-N-methyl-benzamide To a solution of 2-(2-amino-ethoxy)-4-chloro-5-(4-cyano-6-trifluoromethyl-pyridin-3-yl)-N-(2-methoxy-phenyl)-N-methyl-benzamide (30 mg, 0.06 mmol) in DCM (1 mL) acetic anhydride (11 μL, 0.12 mmol) and DIPEA (16 μL, 0.09 mmol) were added. The mixture was stirred at rt overnight, concentrated, diluted with 1 mL MeOH and purified by preparative HPLC yielding 2-(2-acetylamino-ethoxy)-4-chloro-5-(4-cyano-6-trifluoromethyl-pyridin-3-yl)-N-(2-methoxy-phenyl)-N-methyl-benzamide. MS: 547.1 (M+H)$^+$, $t_R$=7.48 min (method 2).

The following compounds were prepared similarly.

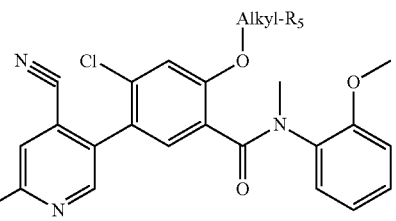

| Ex. | -Alkyl- | —R$_5$ | MS (M + H)$^+$ | $t_R$ (min) | HPLC Method |
|---|---|---|---|---|---|
| 47-1 | —CH$_2$CH$_2$— | —NHC(═O)CH$_3$ | 547.1 | 7.48 | 2 |
| 47-2 | —CH$_2$CH$_2$— | —N(CH$_3$)C(═O)CH$_3$ | 561.0 | 7.19 | 2 |
| 47-3 | —CH$_2$CH$_2$CH$_2$— | —NHC(═O)CH$_3$ | 561.1 | 7.28 | 2 |
| 47-4 | —CH$_2$CH$_2$— | —NHC(═O)CF$_3$ | 601.1 | 8.54 | 2 |
| 47-5 | —CH$_2$CH$_2$— | —N(CH$_3$)C(═O)CF$_3$ | 615.0 | 8.78 | 2 |

Example 48

4-Chloro-5-(4-cyano-6-trifluoromethyl-pyridin-3-yl)-2-(2-methanesulfonylamino-ethoxy)-N-(2-methoxy-phenyl)-N-methyl-benzamide

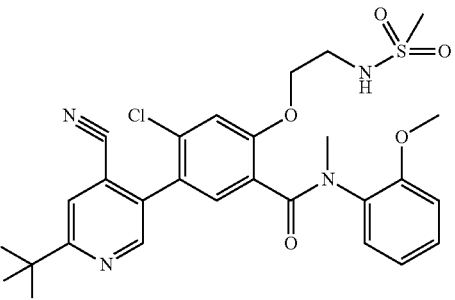

Step 48A: 4-Chloro-5-(4-cyano-6-trifluoromethyl-pyridin-3-yl)-2-(2-methanesulfonylamino-ethoxy)-N-(2-methoxy-phenyl)-N-methyl-benzamide To a solution of 2-(2-amino-ethoxy)-4-chloro-5-(4-cyano-6-trifluoromethyl-pyridin-3-yl)-N-(2-methoxy-phenyl)-N-methyl-benzamide (30 mg, 0.06 mmol) in DCM (1 mL), methanesulfonylchloride (7 μL, 0.09 mmol) and DIPEA (16 μL, 0.09 mmol) were added. The mixture was stirred at rt overnight, concentrated, diluted with 1 mL MeOH and purified by prep HPLC yielding 4-chloro-5-(4-cyano-6-trifluoromethyl-pyridin-3-yl)-2-(2-methanesulfonylamino-ethoxy)-N-(2-methoxy-phenyl)-N-methyl-benzamide 48-1. MS: 583.0 (M+H)$^+$, $t_R$=7.61 min (method 2).

4-Chloro-5-(4-cyano-6-trifluoromethyl-pyridin-3-yl)-2-[2-(methanesulfonyl-methyl-amino)-ethoxy]-N-(2- methoxy-phenyl)-N-methyl-benzamide 48-2 was prepared similarly. MS: 597.1 (M+H)$^+$, $t_R$=7.91 min (method 2).

Example 49

(S)-1-(3-{5-Chloro-4-(4-cyano-6-trifluoromethyl-pyridin-3-yl)-2-[(2-methoxy-phenyl)-methyl-carbamoyl]-phenoxy}-propyl)-pyrrolidine-2-carboxylic acid

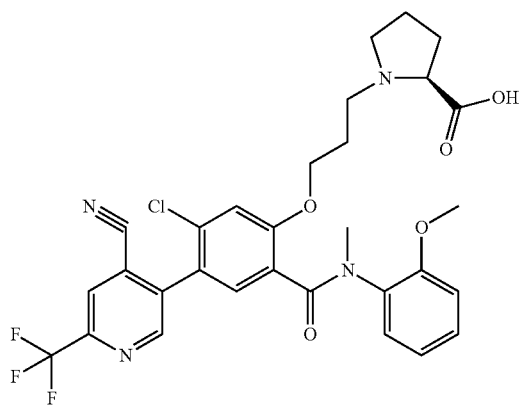 [SMILES: COc1ccccc1N(C)C(=O)c1cc(-c2cnc(C(F)(F)F)cc2C#N)c(Cl)cc1OCCCN1CCC[C@H]1C(=O)O]

(26 mg, 0.1 mmol) and DIAD (20 µL, 0.1 mmol) were added. The mixture was stirred at rt overnight, concentrated, diluted with 1 mL MeOH and purified by prep HPLC. The resulting (S)-1-(2-{5-chloro-4-(4-cyano-6-trifluoromethyl-pyridin-3-yl)-2-[(2-methoxy-phenyl)-methyl-carbamoyl]-phenoxy}-ethyl)-pyrrolidine-2-carboxylic acid tert-butyl ester was treated with 50% TFA in DCM (2 mL), stirred at rt for 4 hrs and concentrated yielding (S)-1-(3-{5-chloro-4-(4-cyano-6-trifluoromethyl-pyridin-3-yl)-2-[(2-methoxy-phenyl)-methyl-carbamoyl]-phenoxy}-propyl)-pyrrolidine-2-carboxylic acid 48-1. MS: 617.4 (M+H)$^+$, $t_R$=4.44 min (method 3).

The following compounds were prepared similarly

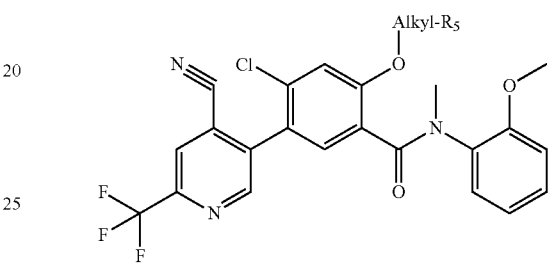

| Ex. | -Alkyl- | —R$_5$ | MS (M + H)$^+$ | $t_R$ (min) | HPLC Method |
|---|---|---|---|---|---|
| 49-1 | —CH$_2$CH$_2$CH$_2$— | (S)-pyrrolidin1-yl-2-carboxylic acid | 617.4 | 4.44 | 3 |
| 49-2 | —CH$_2$CH$_2$— | (R)-pyrrolidin1-yl-2-carboxylic acid | 603.4 | 3.85 | 3 |
| 49-3 | —CH$_2$CH$_2$— | (S)-pyrrolidin1-yl-2-carboxylic acid | 603.3 | 3.81 | 3 |
| 49-4 | —CH$_2$CH$_2$CH$_2$— | (R)-pyrrolidin1-yl-2-carboxylic acid | 617.4 | 4.39 | 3 |

Step 49A: (S)-1-(3-Hydroxy-propyl)-pyrrolidine-2-carboxylic acid tert-butyl ester To a solution of (S)-pyrrolidine-2-carboxylic acid tert-butyl ester (350 mg, 2.04 mmol) in CH$_3$CN (5 mL), 3-bromo-propan-1-ol (268 µL, 3.06 mmol) and K$_2$CO$_3$ (844 mg, 6.12 mmol) were added. The mixture was heated at 85° C. overnight, concentrated and purified by silica gel column chromatography (DCM/MeOH=95/5) to afford 444 mg (S)-1-(3-hydroxy-propyl)-pyrrolidine-2-carboxylic acid tert-butyl ester. MS: 230.2 (M+H)$^+$, $t_R$=0.99 min (method 1).

Step 49B: (S)-1-(3-{5-Chloro-4-(4-cyano-6-trifluoromethyl-pyridin-3-yl)-2-[(2-methoxy-phenyl)-methyl-carbamoyl]-phenoxyl}-propyl)-pyrrolidine-2-carboxylic acid To 4-chloro-5-(4-cyano-6-trifluoromethyl-pyridin-3-yl)-2-hydroxy-N-(2-methoxy-phenyl)-N-methyl-benzamide alcohol (30 mg, 0.065 mmol) dissolved in THF (700 µL), (S)-1-(3-hydroxy-propyl)-pyrrolidine-2-carboxylic acid tert-butyl ester (18 mg, 0.078 mmol), triphenylphosphine

Example 50

(S)-1-[3-(2-{[4-Chloro-3-(4-cyano-6-trifluoromethyl-pyridin-3-yl)-benzoyl]-methyl-amino}-phenoxy)-propyl]-pyrrolidine-2-carboxylic acid Step 50A: (S)-1-[3-(2-{[4-Chloro-3-(4-cyano-6-trifluoromethyl-pyridin-3-yl)-benzoyl]-methyl-amino}-phenoxy)-propyl]-pyrrolidine-2-carboxylic acid To 4-chloro-3-(4-cyano-6-trifluoromethyl-pyridin-3-yl)-N-(2-hydroxy-phenyl)-N-methyl-benzamide (30 mg, 0.069 mmol) dissolved in THF (700 µL), (S)-1-(3-hydroxy-propyl)-pyrrolidine-2-carboxylic acid tert-butyl ester (18 mg, 0.078 mmol), triphenylphosphine (26 mg, 0.1 mmol) and DIAD (20 µL, 0.1 mmol) were added. The mixture was stirred at rt overnight, concentrated, diluted with 1 mL MeOH and purified by prep HPLC. The resulting (S)-1-[3-(2-{[4-chloro-3-(4-cyano-6-trifluoromethyl-pyridin-3-yl)-benzoyl]-methyl-amino}-phenoxy)-propyl]-pyrrolidine-2-carboxylic acid tert-butyl ester was treated with 50% TFA in DCM (2 mL), stirred at rt for 4 hrs and concentrated yielding (S)-1-[3-(2-{[4-chloro-3-(4-cyano-6-trifluoromethyl-pyridin-3-yl)-benzoyl]-methyl-amino}-phenoxy)-propyl]-pyrrolidine-2-carboxylic acid 50-1. MS: 587.4 (M+H)$^+$, $t_R$=4.34 min (method 3).

The following compounds were prepared similarly

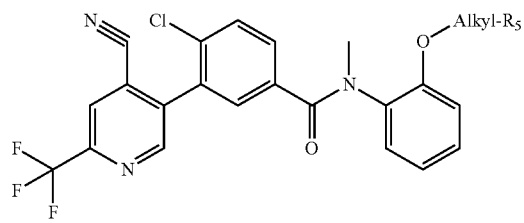

| Ex. | -Alkyl- | —R$_5$ | MS (M + H)$^+$ | $t_R$ (min) | HPLC Method |
|---|---|---|---|---|---|
| 50-1 | —CH$_2$CH$_2$CH$_2$— | (S)-pyrrolidin1-yl-2-carboxylic acid | 587.4 | 4.34 | 3 |
| 50-2 | —CH$_2$CH$_2$— | (R)-pyrrolidin1-yl-2-carboxylic acid | 573.1 | 5.92 | 2 |
| 50-3 | —CH$_2$CH$_2$— | (S)-pyrrolidin1-yl-2-carboxylic acid | 573.1 | 5.93 | 2 |
| 50-4 | —CH$_2$CH$_2$CH$_2$— | (R)-pyrrolidin1-yl-2-carboxylic acid | 587.4 | 4.33 | 3 |

Step 51A: Methanesulfonic acid 2-(pyridin-2-yloxy)-ethyl ester 2-(Pyridin-2-yloxy)-ethanol (100 mg, 0.72 mmol) was dissolved in DCM (2 mL) and MsCl (72 µL, 0.94 mmol) and DIPEA (192 µL, 1.08 mmol) were added. The mixture was stirred at rt overnight, diluted with EtOAc, washed with water, sat. NaHCO$_3$ and brine, dried (Na$_2$SO$_4$), filtered and concentrated in vacuo to afford 114 mg methanesulfonic acid 2-(pyridin-2-yloxy)-ethyl ester which was used without further purification for the next step.

Step 51B: 4-Chloro-3-(4-cyano-6-trifluoromethyl-pyridin-3-yl)-N-methyl-N-{2-[2-(pyridin-2-yloxy)-ethoxy]-phenyl}-benzamide To 4-chloro-3-(4-cyano-6-trifluoromethyl-pyridin-3-yl)-N-(2-hydroxy-phenyl)-N-methyl-benzamide (50 mg, 0.12 mmol) dissolved in DMF (500 µL), methanesulfonic acid 2-(pyridin-2-yloxy)-ethyl ester (30 mg, 0.14 mmol) and K$_2$CO$_3$ (50 mg, 0.36 mmol) were added. The mixture was stirred at rt overnight then heated at 40° C. for 1 h. After filtration and dilution with MeOH the mixture was purified by prep HPLC yielding 4-chloro-3-(4-cyano-6-trifluoromethyl-pyridin-3-yl)-N-methyl-N-{2-[2-(pyridin-2-yloxy)-ethoxy]-phenyl}-benzamide 51-1. MS: 553.2 (M+H)$^+$, $t_R$=5.2 min (method 3).

Example 51

4-Chloro-3-(4-cyano-6-trifluoromethyl-pyridin-3-yl)-N-methyl-N-{2-[2-(pyridin-2-yloxy)-ethoxy]-phenyl}-benzamide Example 52

3-(2-{[4-Chloro-3-(4-cyano-6-trifluoromethyl-pyridin-3-yl)-benzoyl]-methyl-amino}-phenoxy)-2,2-dimethyl-propionic acid

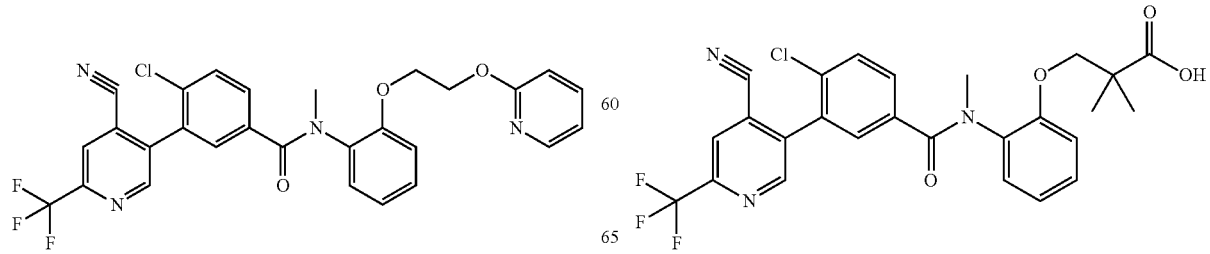

Step 52A: 4-Chloro-3-(4-cyano-6-trifluoromethyl-pyridin-3-yl)-N-[2-(3-hydroxy-2,2-dimethyl-propoxy)-phenyl]-N-methyl-benzamide 4-Chloro-3-(4-cyano-6-trifluoromethyl-pyridin-3-yl)-N-(2-hydroxy-phenyl)-N-methyl-benzamide (200 mg, 0.46 mmol) was dissolved in DMF (2 mL) and 3-bromo-2,2-dimethyl-propan-1-ol (72 µL, 0.94 mmol) and $K_2CO_3$ (192 µL, 1.08 mmol) were added. The mixture was stirred at 65° C. for 24 hrs, cooled to rt, diluted with EtOAc, washed with water and brine, dried ($Na_2SO_4$), filtered and concentrated. Silica gel column chromatography (1% MeOH in DCM with gradient up to 5% MeOH in DCM) followed by prep HPLC afforded 4-chloro-3-(4-cyano-6-trifluoromethyl-pyridin-3-yl)-N-[2-(3-hydroxy-2,2-dimethyl-propoxy)-phenyl]-N-methyl-benzamide. MS: 518.3 $(M+H)^+$, $t_R$=6.16 min (method 3).

Step 52B. 3-(2-{[4-Chloro-3-(4-cyano-6-trifluoromethyl-pyridin-3-yl)-benzoyl]-methyl-amino}-phenoxy)-2,2-dimethyl-propionic acid To periodic acid (68 mg, 0.30 mmol) in $CH_3CN$ (200 µL) at 0° C., Cr(VI)oxide (0.7 mg, 0.0073 mmol) was added and the mixture was stirred for 15 min at 0° C. A solution of 4-chloro-3-(4-cyano-6-trifluoromethyl-pyridin-3-yl)-N-[2-(3-hydroxy-2,2-dimethyl-propoxy)-phenyl]-N-methyl-benzamide (29 mg, 0.056 mmol) dissolved in $CH_3CN$ (200 µL) was added and the mixture was warmed to rt. After 2 hr at rt, the mixture was filtered, rinsed with $CH_3CN$, concentrated, dissolved in MeOH and purified by prep HPLC yielding 3-(2-{[4-chloro-3-(4-cyano-6-trifluoromethyl-pyridin-3-yl)-benzoyl]-methyl-amino}-phenoxy)-2,2-dimethyl-propionic acid 52-1. MS: 532.3 $(M+H)^+$, $t_R$=3.65 min (method 3).

Example 53

N-{2-[2-(2-Amino-ethylcarbamoyl)-ethoxy]-phenyl}-4-chloro-3-(4-cyano-6-trifluoromethyl-pyridin-3-yl)-N-methylbenzamide

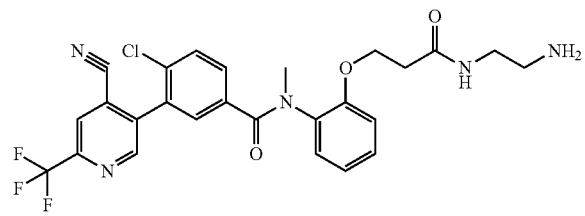 [SMILES: CN(C(=O)c1ccc(Cl)c(-c2cnc(C(F)(F)F)cc2C#N)c1)c1ccccc1OCCC(=O)NCCN]

Step 52A: N-{2-[2-(2-Amino-ethylcarbamoyl)-ethoxyl]-phenyl}-4-chloro-3-(4-cyano-6-trifluoromethyl-pyridin-3-yl)-N-methylbenzamide To a mixture of 3-(2-{[4-chloro-3-(4-cyano-6-trifluoromethyl-pyridin-3-yl)-benzoyl]-methyl-amino}-phenoxy)-propionic acid 11-4 (50 mg, 0.10 mmol) and (2-amino-ethyl)-carbamic acid tert-butyl ester (51.5 mg, 0.54 mmol) in DMF (500 µL), EDCI (22 mg, 0.12 mmol), HOBt (16 mg, 0.12 mmol) and DIPEA (34 µl, 0.19 mmol) were added. The mixture was stirred for 48 hrs at rt, diluted with MeOH (500 µL) and purified by prep HPLC to afford {2-[3-(2-{[4-chloro-3-(4-cyano-6-trifluoromethyl-pyridin-3-yl)-benzoyl]-methyl-amino}-phenoxy)-propionylamino]-ethyl}-carbamic acid tert-butyl ester. After treatment with 50% TFA in DCM (1 mL) for 2 hrs, followed by concentration in vacuo, N-{2-[2-(2-amino-ethylcarbamoyl)-ethoxy]-phenyl}-4-chloro-3-(4-cyano-trifluoromethyl-pyridin-3-yl)-N methyl-benzamide 53-1 was obtained. MS $[M+H]^+$ 546.1; $t_R$=5.66 min (method 2).

Similarly 4-Chloro-3-(4-cyano-6-trifluoromethyl-pyridin-3-yl)-N-methyl-N-[2-(3-oxo-3-piperazin-1-yl-propoxy)-phenyl]-benzamide 53-2 was prepared. MS $[M+H]^+$ 572.1; $t_R$=5.89 min (method 2).

It will be appreciated that, although specific embodiments of the invention have been described herein for purposes of illustration, various modifications may be made without departing from the spirit and scope of the invention. Accordingly, the invention is not limited except as by the appended claims.

We claim:
1. A method for treating a sex-hormone related condition of a subject in need thereof, comprising administering to the subject an effective amount of a compound having the following structure (I):

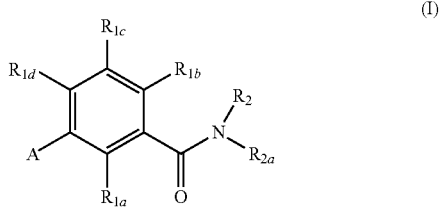

or a stereoisomeror pharmaceutically acceptable salt thereof, wherein:
A is pyridyl, phenyl, quinolinyl, naphthyridinyl, thienopyrimidinyl, or 2-oxo-pyrimidinyl, wherein the pyridyl, phenyl, quinolinyl, thienopyrimidinyl or 2-oxo-pyrimidinyl is substituted with 0-5 $R_4$;
$R_{1a}$ is H, halogen, $C_{1-4}$alkyl, alkoxy or trifluoromethyl;
$R_{1b}$ and $R_{1c}$ are the same or different and are independently H, halogen, hydroxy, halo$C_{1-4}$alkyl, —$C_{1-6}$alkyl-$(R_5)_p$, —O—$C_{1-6}$alkyl-$(R_5)_p$, —$C_{1-6}$alkyl-O—$C_{1-6}$alkyl-$(R_5)_p$, —$NR_7$—$C_{1-6}$alkyl-$(R_5)_p$, or —$S(O)_m$—$C_{1-6}$alkyl-$(R_5)_p$;
$R_{1d}$ is Cl, F, methyl, $CF_3$ or cyano;
$R_2$ is —$C_{1-4}$alkyl-$(R)_p$;
$R_{2a}$ is phenyl substituted with 0-4 $R_3$, heteroaryl substituted with 0-4 $R_3$, $C_{1-6}$alkyl substituted with 0-4 $R_3$, aryl-$C_{1-4}$alkyl substituted with 0-4 $R_3$, or heteroaryl-$C_{1-4}$alkyl substituted with 0-4 $R_3$;
$R_3$ at each occurrence is independently halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$;
$R_4$ at each occurrence is independently halogen, $C_{1-6}$alkyl, halo$C_{1-4}$alkyl, $C_{1-6}$alkoxy, hydroxy, cyano, thio$C_{1-6}$alkyl, —$C(O)NR_7R_8$ or 5 member heteroaryl;
$R_5$ at each occurrence is independently H, hydroxy, —OC(O)—$C_{1-6}$alkyl, —OC(O)O—$C_{1-6}$alkyl, —OC(O)—$C_{1-6}$alkyl-$NR_7R_8$, —$COOR_6$, —$C(O)NR_7R_8$, —$NR_7C(O)NR_7R_8$, —$S(O)_2NR_9R_9$, —$S(O)_m$—$C_{1-4}$alkyl, —$NR_7R_8$, $C_{1-6}$alkoxy, —O-heterocycle, or heterocycle wherein said heterocycle and said —O-heterocycle are substituted with 0-4 groups selected from halogen, $C_{1-6}$alkyl, $C_{1-4}$haloalkyl, hydroxy, oxo, thio, —$NH_2$, —$S(O)_2C_{1-4}$alkyl and —COOH;

$R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ at each occurrence is independently H, $C_{1-4}$alkyl, hydroxy, or heterocycle where said heterocycle is substituted with 0-4 groups selected from halogen, $C_{1-6}$alkyl, hydroxy, keto, —$NH_2$ and —COOH;

$R_8$ at each occurrence is independently H, $C_{1-4}$alkyl, halo$C_{1-4}$alkyl, —C(O)—$C_{1-4}$alkyl, —C(O)-halo-$C_{1-4}$alkyl, —$S(O)_m$-halo$C_{1-4}$alkyl or —$S(O)_m$—$C_{1-4}$alkyl;

$R_9$ at each occurrence is independently H, $C_{1-4}$alkyl, or —$C(O)C_{1-4}$alkyl;

m is 0-2; and p at each occurrence is independently 1-3.

2. The method of claim 1 wherein the compound has the following structure (Ia):

(Ia)

or a stereoisomer or pharmaceutically acceptable salt thereof, wherein:

A is pyridyl, phenyl, quinolinyl, thienopyrimidinyl, or 2-oxo-pyrimidinyl, wherein the pyridyl, phenyl, quinolinyl, thienopyrimidinyl or 2-oxo-pyrimidinyl is substituted with 0-4 $R_4$;

$R_{1a}$ is H, halogen, alkyl, alkoxy or trifluoromethyl;

$R_{1b}$ and $R_{1c}$ are the same or different and are independently H, halogen, hydroxy, halo$C_{1-4}$alkyl, —$C_{1-6}$alkyl-$(R_5)_p$, —O—$C_{1-6}$alkyl-$(R_5)_p$, —$C_{1-6}$alkyl-O—$C_{1-6}$alkyl-$(R_5)_p$, —$NR_7$—$C_{1-6}$alkyl-$(R_5)_p$, or —$S(O)_m$—$C_{1-6}$alkyl-$(R_5)_p$;

$R_{1d}$ is Cl, methyl, $CF_3$ or cyano;

$R_2$ is $C_{1-4}$alkyl-$(R_5)_p$;

$R_3$ at each occurrence is independently halogen, halo$C_{1-4}$alkyl, hydroxy, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —$CO_2R_6$, —$C(O)NR_7R_8$;

$R_4$ at each occurrence is independently alkyl, halo$C_{1-4}$alkyl, $C_{1-4}$alkoxy, hydroxy, cyano, thio-$C_{1-4}$alkyl, —$C(O)NR_7R_8$ or 5 member heteroaryl;

$R_5$ at each occurrence is independently H, hydroxy, —OC(O)—$C_{1-6}$alkyl, —OC(O)O—$C_{1-6}$alkyl, —OC(O)—$C_{1-6}$alkyl-$NR_7R_8$, —$COOR_6$, —$C(O)NR_7R_8$, —$S(O)_2NR_9R_9$, —$S(O)_mC_{1-4}$alkyl, —$NR_7R_8$, $C_{1-6}$alkoxy, or a heterocycle selected from the group consisting of $R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ is H, $C_{1-4}$alkyl or hydroxy;

$R_8$ is H, $C_{1-4}$alkyl, —C(O)—$C_{1-4}$alkyl, or —$S(O)_m$—$C_{1-4}$alkyl;

$R_9$ at each occurrence is independently H, $C_{1-4}$alkyl, or —$C(O)C_{1-4}$alkyl;

m is 0-2;

n is 0-4; and p at each occurrence is independently 1-3.

3. The method of claim 1 wherein A is pyridyl substituted with 0-4 $R_4$.

4. The method of claim 3 wherein A is 2-pyridyl substituted with 0-4$R_4$.

5. The method of claim 3 wherein A is 3-pyridyl substituted with 0-4$R_4$.

6. The method of claim 1 wherein A is phenyl substituted with 0-4 $R_4$.

7. The method of claim 1 wherein A is quinolinyl substituted with 0-4 $R_4$.

8. The method of claim 1 wherein A is thienopyrimidinyl substituted with 0-4 $R_4$.

9. The method of claim 1 wherein A is 2-oxo-pyrimidinyl substituted with 0-4 $R_4$.

10. The method of claim 1 wherein $R_{1a}$ and $R_{1c}$ are H.

11. The method of claim 1 wherein $R_{1b}$ is —$C_{1-6}$alkyl-$(R_5)_p$ or —O—$C_{1-6}$alkyl-$(R_5)_p$, p is 1, and $R_5$ is H, hydroxy, or —$COOR_6$.

12. The method of claim 1 wherein $R_{2a}$ is phenyl substituted with 1 or 2 $R_3$, wherein one of $R_3$ is —O—$C_{1-6}$alkyl-$(R_5)_p$, p is 1, and $R_5$ is H, hydroxy, or —$COOR_6$.

13. The method of claim 1 wherein $R_3$ is —$C_{1-6}$alkyl-$(R_5)_p$, —$C_{1-6}$alkyl-O—$C_{1-6}$alkyl-$(R_5)_p$ or —O—$C_{1-6}$alkyl-$(R_5)_p$.

14. The method of claim 1 wherein the compound is 3-(2-{[4-Chloro-3-(6-chloro-4-methyl-pyridin-3-yl)-benzoyl]-methyl-amino}-phenoxy)-propionic acid, 3-(2-{[4-Chloro-3-(4-methyl-6-trifluoromethyl-pyridin-3-yl)-benzoyl]-methyl-amino}-phenoxy)-propionic acid, 3-(2-{[4-Chloro-3-(4-cyano-6-trifluoromethyl-pyridin-3-yl)-benzoyl]-methyl-amino}-phenoxy)-propionic acid, 3-(2-{[4-Chloro-3-(4-methyl-6-trifluoromethyl-pyridin-3-yl)-benzoyl]-methyl-amino}-3-methyl-phenoxy)-propionic acid, 3-(2-{[4-Chloro-3-(6-cyano-4-methyl-pyridin-3-yl)-benzoyl]-methyl-amino}-3-methyl-phenoxy)-propionic acid, 3-(2-{[4-Chloro-3-(4-cyano-6-trifluoromethyl-pyridin-3-yl)-benzoyl]-methyl-amino}-3-methyl-phenoxy)-propionic acid, 4-(2-{[4-Chloro-3-(4-cyano-6-trifluoromethyl-pyridin-3-yl)-benzoyl]-methyl-amino}-phenyl)-butyric acid, 2-{[4-Chloro-5-(4-cyano-6-trifluoromethyl-pyridin-3-yl)-2-methoxy-benzoyl]-methyl-amino}-benzoic acid methyl ester, 4-Chloro-5-(4-cyano-6-trifluoromethyl-pyridin-3-yl)-N-(2-fluoro-6-methoxy-phenyl)-2-methoxy-N-methyl-benzamide, or a pharmaceutically acceptable salt thereof.

15. The method of claim 1 wherein the compound is 4-{5-Chloro-4-(4-cyano-6-trifluoromethyl-pyridin-3-yl)-2-[(2-methoxy-6-methyl-phenyl)-methyl-carbamoyl]-phenoxy}-butyric acid, 3-{5-Chloro-4-(4-cyano-6-trifluoromethyl-pyridin-3-yl)-2-[(2-methoxy-6-methyl-phenyl)-methyl-carbamoyl]-phenoxy}-propionic acid, 4-{5-Chloro-4-(4-cyano-6-trifluoromethyl-pyridin-3-yl)-2-[(2-methoxy-phenyl)-methyl-carbamoyl]-phenoxy}-butyric acid, 4-[5-Chloro-2-[(5-chloro-2-methoxy-phenyl)-methyl-carbamoyl]-4-(4-cyano-6-trifluoromethyl-pyridin-3-yl)-phenoxy]-butyric acid, 2-{[2-(3-Carboxy-propoxy)-4-chloro-5-(4-cyano-6-trifluoromethyl-pyridin-3-yl)-benzoyl]-methyl-amino}-benzoic acid methyl ester, 4-{5-Chloro-4-(4-cyano-6-trifluoromethyl-pyridin-3-yl)-2-[methyl-(2-oxazol-5-yl-phenyl)-carbamoyl]-phenoxy}-butyric acid, 4-{5-Chloro-4-(4-cyano-6-trifluoromethyl-pyridin-3-yl)-2-[(2-fluoro-6-methoxy-phenyl)-methyl-carbamoyl]-phenoxy}-butyric acid, 4-Chloro-5-(4-cyano-6-trifluoromethyl-pyridin-3-yl)-N-(2-methoxy-phenyl)-N-methyl-2-[3-(2H-tetrazol-5-yl)-propoxy]-benzamide, 4-Chloro-3-(4-cyano-6-trifluoromethyl-pyridin-3-yl)-N-methyl-N-{2-[2-(1H-tetrazol-5-yl)-ethoxy]-phenyl}-benzamide, or a pharmaceutically acceptable salt thereof.

16. The method of claim 1, wherein the compound is administered to the subject in the form of a pharmaceutical composition comprising the compound, or a pharmaceutically acceptable salt thereof, and a pharmaceutically acceptable carrier or diluent.

17. The method of claim 1, wherein the condition is endometriosis, uterine fibroids, polycystic ovarian disease, dysmenorrhea, dyspareunia, menorrhagia, nonmenstrual pelvic pain, pelvic tenderness, induration, general disorders of the menstrual cycle, premature ovarian failure due to chemotherapy or early menopause, hirsutism, precocious puberty, gonadal steroid-dependent neoplasia such as cancers of the prostate, breast and ovary, gonadotroph pituitary adenomas, adenomyosis, sleep apnea, irritable bowel syndrome, premenstrual syndrome, benign prostatic hypertrophy, lower urinary tract symptoms, or contraception or infertility.

18. The method of claim 17 wherein the condition is endometriosis, dysmenorrhea, polycystic ovarian disease or uterine fibroids.

19. The method of claim 17 wherein the condition is benign prostatic hypertrophy, lower urinary tract symptoms, myoma of the uterus, prostatic cancer, uterine cancer, breast cancer or pituitary gonadotroph adenomas.

* * * * *